US011137163B2

(12) United States Patent
Nasis

(10) Patent No.: US 11,137,163 B2
(45) Date of Patent: Oct. 5, 2021

(54) ENVIRONMENT MONITORING AND MANAGEMENT SYSTEMS AND METHODS

(71) Applicant: AIRTHINX, INC, Philadelphia, PA (US)

(72) Inventor: Vasileios Nasis, Philadelphia, PA (US)

(73) Assignee: AIRTHINX, INC, Philadelphia, PA (US)

(*) Notice: Subject to any disclaimer, the term of this patent is extended or adjusted under 35 U.S.C. 154(b) by 0 days.

(21) Appl. No.: 16/931,300

(22) Filed: Jul. 16, 2020

(65) Prior Publication Data
US 2021/0018210 A1 Jan. 21, 2021

Related U.S. Application Data

(60) Provisional application No. 62/874,750, filed on Jul. 16, 2019.

(51) Int. Cl.
*G05B 21/00* (2006.01)
*G01M 1/38* (2006.01)
(Continued)

(52) U.S. Cl.
CPC ............ *F24F 11/65* (2018.01); *G01N 33/004* (2013.01); *G01N 33/0047* (2013.01);
(Continued)

(58) Field of Classification Search
CPC .... F24F 11/65; F24F 2110/10; F24F 2110/65; F24F 2110/72; F24F 2110/40;
(Continued)

(56) References Cited

U.S. PATENT DOCUMENTS

2006/0173580 A1* 8/2006 Desrochers ........ G01N 33/0075
700/276
2015/0032264 A1* 1/2015 Emmons ................. F24F 11/62
700/276
(Continued)

FOREIGN PATENT DOCUMENTS

GB 2 563 008 A 12/2018
WO WO-2018/091340 A1 5/2018

OTHER PUBLICATIONS

International Search Report dated Nov. 3, 2020, for PCT Application No. PCT/US2020/042413, filed on Jul. 16, 2020, 5 pages.
(Continued)

*Primary Examiner* — Zhipeng Wang
(74) *Attorney, Agent, or Firm* — Cooley LLP

(57) ABSTRACT

A method for managing air quality may include, at one or more processors, receiving sensor data comprising a plurality of air quality parameters for an environment, wherein the sensor data is generated by one or more environment quality monitoring devices located in the environment, predicting an adverse air quality event based on the sensor data, and automatically controlling one or more devices to mitigate the adverse air quality event. An environment quality monitoring device may include a housing, a plurality of sensors in the housing and configured to generate sensor data comprising a plurality of environment quality parameters, a network communication device configured to communicate the sensor data over a network, and an alert configured to indicate an environment quality score of the ambient environment, where the environment quality score is based on at least a portion of the sensor data.

16 Claims, 35 Drawing Sheets

(51) Int. Cl.
*G05B 13/00* (2006.01)
*G05B 15/00* (2006.01)
*G05D 23/00* (2006.01)
*F24F 11/65* (2018.01)
*G01N 33/00* (2006.01)
*G05B 13/02* (2006.01)
*G05B 13/04* (2006.01)
*F24F 110/20* (2018.01)
*F24F 110/70* (2018.01)
*F24F 110/72* (2018.01)
*F24F 110/40* (2018.01)
*F24F 110/66* (2018.01)
*F24F 110/10* (2018.01)
*F24F 110/65* (2018.01)
*H04W 84/18* (2009.01)

(52) U.S. Cl.
CPC ....... *G05B 13/0265* (2013.01); *G05B 13/048* (2013.01); *F24F 2110/10* (2018.01); *F24F 2110/20* (2018.01); *F24F 2110/40* (2018.01); *F24F 2110/65* (2018.01); *F24F 2110/66* (2018.01); *F24F 2110/70* (2018.01); *F24F 2110/72* (2018.01); *H04W 84/18* (2013.01)

(58) Field of Classification Search
CPC ............... F24F 2110/20; F24F 2110/70; F24F 2110/66; G01N 33/004; G01N 33/0047; G05B 13/0265; G05B 13/048; H04W 84/18

See application file for complete search history.

(56) References Cited

U.S. PATENT DOCUMENTS

| | | | |
|---|---|---|---|
| 2015/0194039 A1* | 7/2015 | Martin | H04W 72/0453 |
| | | | 340/632 |
| 2016/0066067 A1* | 3/2016 | Schultz | H04Q 9/00 |
| | | | 340/870.07 |
| 2016/0066068 A1* | 3/2016 | Schultz | F24F 11/00 |
| | | | 340/870.07 |
| 2016/0116181 A1* | 4/2016 | Aultman | F24F 11/70 |
| | | | 700/276 |
| 2017/0130981 A1 | 5/2017 | Willette et al. | |
| 2018/0073759 A1 | 3/2018 | Zhang et al. | |
| 2018/0299151 A1* | 10/2018 | Ajax | F24F 11/0001 |
| 2019/0346417 A1* | 11/2019 | Benefield | G01N 33/0034 |
| 2020/0117940 A1* | 4/2020 | Wang | G06K 9/036 |
| 2020/0141604 A1* | 5/2020 | Chen | F24F 11/39 |
| 2020/0186626 A1* | 6/2020 | Martin | H04L 69/08 |

OTHER PUBLICATIONS

Written Opinion of the International Searching Authority dated Nov. 3, 2020, for PCT Application No. PCT/US2020/042413, filed on Jul. 16, 2020, 7 pages.

* cited by examiner

ENVIRONMENT MONITORING AND MANAGEMENT SYSTEMS AND METHODS

CROSS-REFERENCE TO RELATED APPLICATIONS

This application claims priority to U.S. Patent Application Ser. No. 62/874,750 filed Jul. 16, 2020, which is incorporated herein in its entirety by this reference.

TECHNICAL FIELD

Devices, systems, and methods herein relate to environment monitoring and/or management.

BACKGROUND

Environmental conditions may have significant effects on population health. For example, air pollution is known to have adverse effects on overall health. For example, exposure to air pollutants can trigger respiratory and inflammatory responses, such as asthma, allergies, and respiratory diseases. In some instances, long-term exposure to air pollutants can lead to more serious conditions such as heart disease and cancer. Certain populations, such as people with lung or heart conditions, may be particularly susceptible to the effects of air pollution. When outdoor air pollution exceeds certain levels, people often seek refuge indoors. However, indoor air pollution may also be a health concern, such as in residential, business, and/or healthcare settings. Furthermore, excessively noisy environments may lead to adverse health effects. For example, long-term exposure to noise can result in permanent degradation or complete loss of hearing. Thus, there is a need for improved environment monitoring systems and methods.

SUMMARY

Generally, in some variations, an environment quality monitoring system includes one or more environment quality monitoring devices that may be connected to a communication network. An environment quality monitoring device may include a housing, a plurality of sensors in the housing and configured to generate sensor data including a plurality of environment quality parameters characterizing ambient environment, a network communication device configured to communicate the sensor data over a network, and an alert configured to indicate an environment quality score of the ambient environment, where the environment quality score is based on at least a portion of the sensor data. The plurality of environment quality parameters may include, for example, amount of particulate matter, an amount of a gas, temperature, humidity, pressure, sound intensity, and/or light intensity in an ambient environment. In some variations, the environment quality monitoring system may further include one or more power source, such as a rechargeable battery (e.g., coupled to the housing).

In some variations, the plurality of sensors may include multiple sensors for measuring particulate matter of different sizes. For example, the plurality of sensors may include a first particulate sensor configured to measure an amount of particulate matter below about 10 µm in diameter, a second particulate sensor configured to measure an amount of particulate matter below about 2.5 µm in diameter, and/or a third particulate sensor configured to measure an amount of particulate matter below about 1 µm in diameter in diameter. Furthermore, the sensors may include sensors configured to detect carbon dioxide, carbon monoxide, formaldehyde and/or volatile organic compounds or other chemicals.

As described above, multiple environment quality monitoring devices may be connected to a network. In some variations, the network may be a wireless network, and each environment quality monitoring device may include a cellular modem for connecting to the network.

Furthermore, an environment quality monitoring device may further include at least one processor configured to generate an environment quality score based on at least a portion of the plurality of environment quality parameters. One exemplary manner of generating the environment quality score is applying a set of weighted factors to the sensor data associated with the environment quality parameters. In some variations, the environment quality score may be communicated to a user through an alert. For example, the alert may include a visual alert on the housing, such as a light waveguide. The light waveguide may be configured to display a visual alert that is color-coded based on a comparison between the environment quality score and one or more predetermined thresholds to categorize the environment quality score in one of multiple predetermined categories of environment quality type. The displayed color may correspond to the environment quality type (e.g., red for poor environment quality, yellow for moderate environment quality, blue for good environment quality, etc.) such that with continuous monitoring of ambient environment, the quality of the ambient environment surrounding the housing may be continuously visually apparent. Similarly, at least one processor may be configured to generate an environment quality parameter score based on at least a portion of the plurality of environment quality parameters, where the environment quality parameter score characterizes a severity of risk associated with at least one environment quality parameter value (e.g., temperature is "high" risk or "low" risk).

In some variations, the environment quality monitoring device (e.g., housing) may include a suitable mount, such as a wall or other surface mount, for securing the environment quality monitoring device to a structure. The mount may, for example, be configured to interface and be retrofit onto an existing HVAC unit. In some variations, the device may further include a locking mechanism releasably coupling the housing to the mount.

The system may further include a user interface configured to display at least one of the sensor data and the environment quality score. In some variations, the user interface is displayable in a web portal application on a remote computing device, and/or in a mobile application on a remote computing device. The user interface may be configured to communicate to the network to access sensor data, sensor data analysis, environment quality score, etc., through an application programming interface (API). Such a user interface may communicate sensor and environment quality information to a user, as well as permit management of connected environment quality monitoring devices.

Generally, in some variations, a method for managing air quality may include, at one or more processors, receiving sensor data comprising a plurality of air quality parameters for an environment, wherein the sensor data is generated by one or more environment quality monitoring devices located in the environment, predicting an adverse air quality event based on the sensor data, and automatically controlling one or more devices to mitigate the adverse air quality event. At least one of the environment quality monitoring devices may be located indoors and/or at least one of the environment quality monitoring devices may be located outdoors.

For example, in some variations the plurality of air quality parameters may include an amount of particulate matter in the environment. In these variations, the adverse air quality event may include an amount of particulate matter above a predetermined threshold level, and automatically controlling one or more devices to mitigate the adverse air quality event may include automatically activating one or more air filtering devices.

As another example, in some variations the plurality of air quality parameters may include an amount of a gas (e.g., carbon dioxide, carbon monoxide, formaldehyde, and/or volatile organic compound (VOC), etc.) in the environment. In these variations, the adverse air quality event may include an amount of the gas above a predetermined threshold level, and wherein automatically controlling one or more devices to mitigate the adverse air quality event comprises automatically activating one or more air purification devices.

As another example, in some variations the plurality of air quality parameters may include one or more of temperature, humidity, and pressure in the environment. In these variations, the adverse air quality event may include at least one of temperature, humidity, and pressure outside a predetermined range, and wherein automatically controlling one or more devices to mitigate the adverse air quality event comprises automatically activating at least one of an HVAC system, a humidifier, and a dehumidifier.

In some variations, the method may include generating an air quality score based on at least a portion of the air quality parameters. Generating the air quality score may, for example, be based on a plurality of weighted factors applied to at least a portion of the air quality parameters. Furthermore, the adverse air quality event may, in some variations, be based at least in part on the air quality score.

The sensor data may be received in various suitable manners. For example, in some variations receiving sensor data may include receiving sensor data from the one or more environment quality monitoring devices over a wireless communication network (e.g., cellular network). Additionally or alternatively, one or more environment quality monitoring devices and one or more devices to mitigate the adverse air quality event are communicatively coupled to a common cloud network. Furthermore, in some variations one or more devices to mitigate the adverse air quality event may be configured to communicate to the cloud network via an application programming interface (API).

In some variations, the method may include providing an alert regarding the predicted adverse air quality event. The alert may, for example, include a visual or audible alert on the one or more environment quality monitoring devices. Additionally or alternatively, the alert may include a notification on a remote computing device.

BRIEF DESCRIPTION OF THE DRAWINGS

FIGS. 3A and 3B are illustrative schematics of a method of using a surface mount in an exemplary variation of an environment quality monitoring device.

DETAILED DESCRIPTION

Non-limiting examples of various aspects and variations of the invention are described herein and illustrated in the accompanying drawings.

Generally, described herein are variations of environment quality monitoring systems for monitoring environmental conditions such as one or more parameters characterizing ambient environment quality. An environment quality monitoring system can include one or more environment quality monitoring devices with one or more sensors configured to measure environment quality parameters, thereby allowing for continuous (or intermittent) environment quality monitoring. Multiple environment quality monitoring devices may, for example, be distributed in various locations to enable simultaneous monitoring of environment quality at the various locations. As further described below, an environment quality score indicating overall quality of ambient environment may be generated based on the sensor data from an environment quality monitoring device. Furthermore, the sensor data may be communicated over a network to one or more memory storage devices and/or one or more processors for tracking and/or further analysis. For example, sensor data for one or more multiple environment quality monitoring devices may be displayed on a user interface (e.g., a web portal application, mobile application, etc.) on a computing device for enabling real-time, continuous monitoring of environment quality conditions. In some variations, as further described below, such user interfaces may enable a user to create and manage alerts that notify designated persons (e.g., via email, SMS text message, notification in the user interface, etc.) when environment quality parameters satisfy one or more predetermined conditions. Furthermore, in some variations, the environment quality monitoring system may be configured to interface with third-party applications through an application program interface (API) to thereby enable integration of environment quality sensor data with third-party software environments.

Variations of the environment quality monitoring device described herein can be installed or otherwise placed in any indoor environments such as residential environments (e.g., homes), healthcare environments (e.g., hospitals, medical clinics, etc.), vehicles (e.g., automobiles, RVs, etc.), other buildings (e.g., offices, warehouses, restaurants, hotels, schools, etc.), and/or other spaces in which environment quality may be monitored. By monitoring environment quality in an indoor environment, users may gain peace of mind that safe conditions exist for occupants of the indoor environment, and take remedial action to improve environment quality if needed.

Monitoring Device and System

Figure 1A:
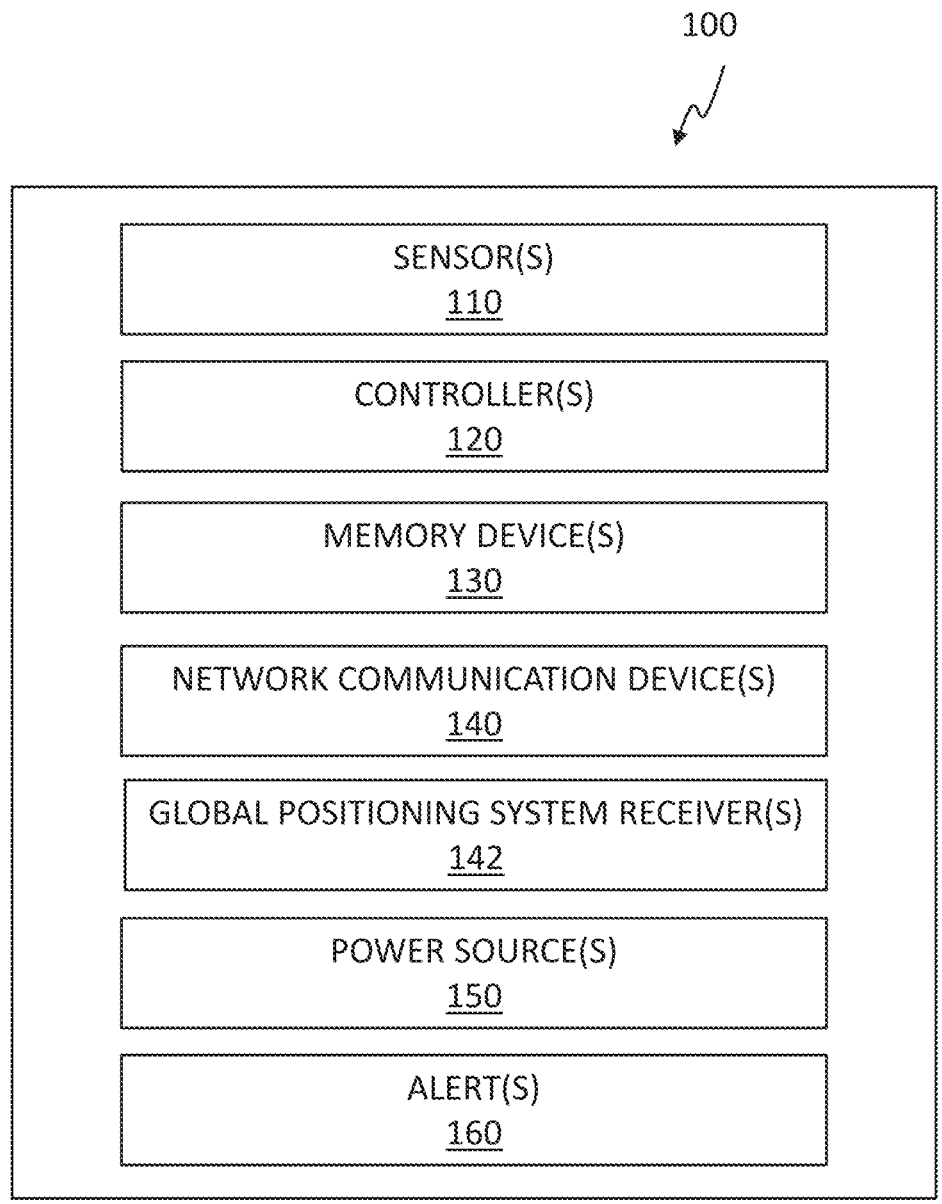
FIG. 1A is an illustrative schematic of an exemplary variation of an environment monitoring device.

As shown in the schematic of FIG. 1A, an environment quality monitoring device 100 may include a plurality of sensors 110 configured to generate sensor data comprising a plurality of environment quality parameters characterizing ambient environment. In some variations, the environment quality monitoring device 100 may further include one or more controllers 120 receiving and analyzing sensor data, one or more memory devices 130 configured to store sensor data and/or results of sensor data analysis, one or more network communication devices 140 configured to communicate the sensor data over a network, and/or one or more power sources 150 configured provide power for the other electronics components within the environment quality monitoring device 100. Some or all of these components may be enclosed in a housing or other suitable enclosure. Additionally or alternatively, in some variations, the environment quality monitoring device 100 may include at least one alert 160 configured to provide an indication of measured ambient environment quality. For example, the alert 160 may be a visual alert (e.g., color-coded light source, text or graphical display, etc.) configured to indicate an environment quality score, wherein the environment quality score is based at least in part on the sensor data.

Figure 1B:
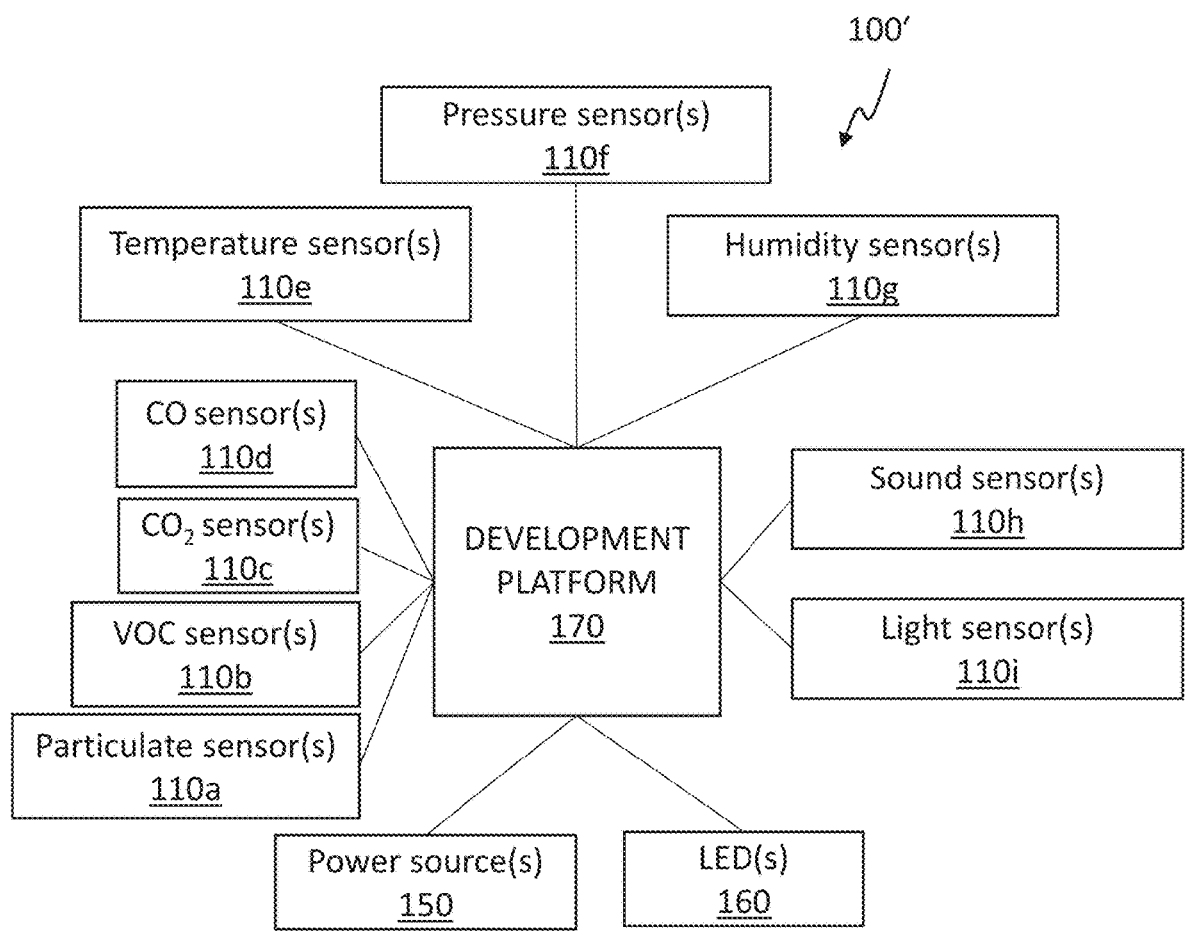
FIG. 1B is another illustrative schematic of an exemplary variation of an environment quality monitoring device.

FIG. 1B illustrates a schematic of an exemplary architecture of an environment quality monitoring device 100'. In some variations, an environment quality monitoring device 100' may include a development platform 170 coupled to one or more sensors (e.g., 110a-110g) configured to generate sensor data comprising a plurality of environment quality parameters characterizing ambient environment. The development platform 170 may include one or more system components for providing a programmable interface for receiving, processing, and/or communicating sensor data to a network system (e.g., as described in further detail below with respect to FIG. 1C). For example, the development platform 170 may include a controller such as a microcontroller unit (MCU), one or more memory devices, one or more processing devices (e.g., for performing EDGE computing), and one or more wireless or wired network communication devices (e.g., 3G/4G/5G, NB-IoT, LoRA, WiFi, Bluetooth, GPS, mesh communication, etc.). In some variations, the development platform 170 may be (or include) a Thiamis X™ device available from Netronix, Inc. (Philadelphia, Pa., USA).

Furthermore, as shown in FIG. 1B, the development platform 170 may be coupled to one or more sensors such as at least one particulate sensor 110a, at least one VOC sensor 110b, at least one carbon dioxide sensor 110c, at least one carbon monoxide sensor 110d, at least one temperature sensor 11e, at least one pressure sensor 110f, at least one humidity sensor 110g, at least one sound intensity sensor 110h, and/or at least one light intensity sensor 110i. The development platform may also be coupled to one or power sources 150 for providing power to the development platform and/or sensor devices, and an alert device such as one or more LEDs 160. Exemplary details of these sensors, power sources, and LEDs or other alert devices are described in further detail below.

Figure 1C:
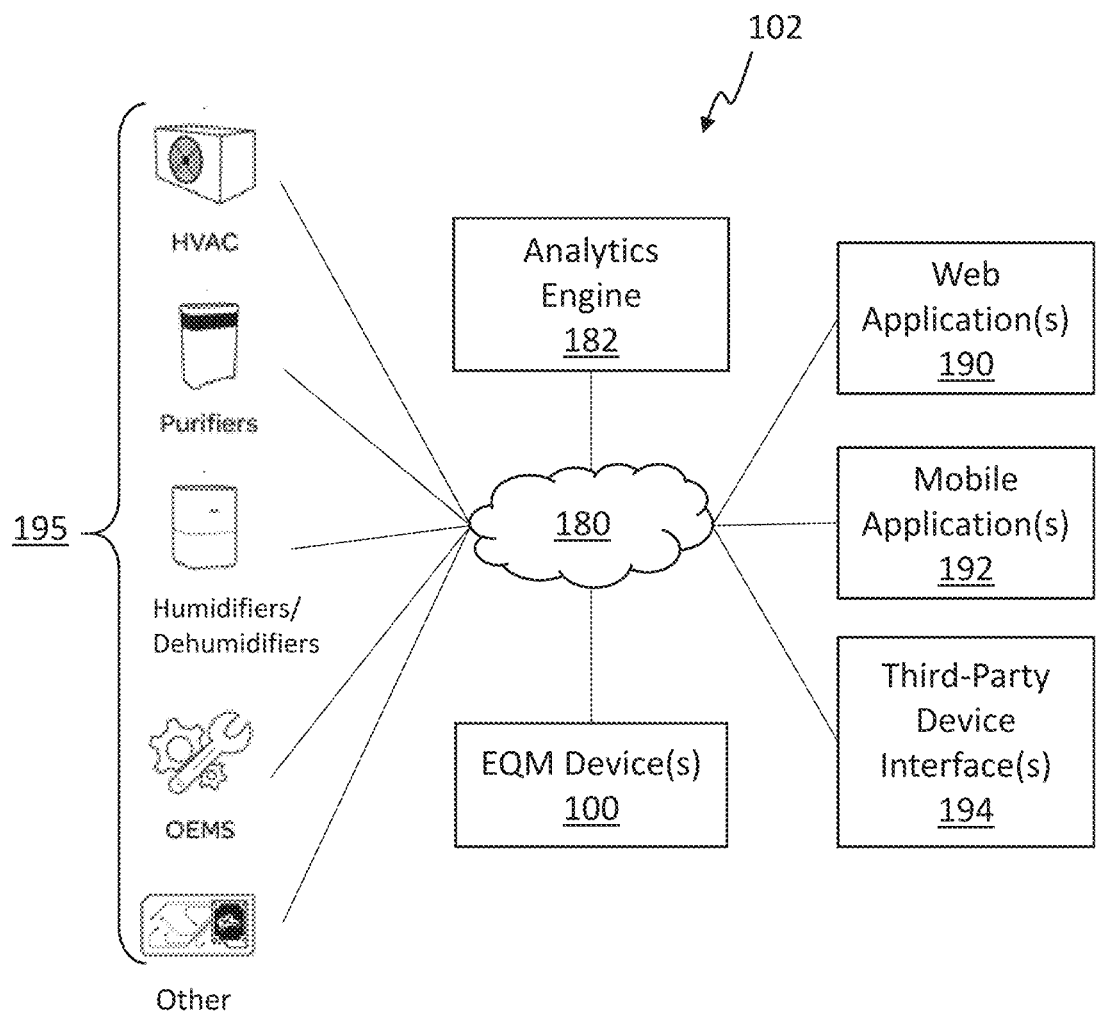
FIG. 1C is an illustrative schematic of an exemplary variation of an environment quality monitoring system including an environment quality monitoring device.

The environment quality monitoring device may, in some variations, be integrated within a monitoring network 102 as shown in FIG. 1C. As shown in FIG. 1C, an environment quality monitoring device 100 may communicate sensor data to a cloud network 180. The cloud network 180, alone or in combination with analytics engine 182, may provide or perform suitable computing functionalities such as hosting, device management, alerts, security, etc. such as through the use of one or more application programming interfaces (as further described below). The monitoring network 102 may further include one or more user-interfacing elements, such as one or more web applications 190, one or more mobile applications 192 (e.g., executable on a mobile computing device such as a smartphone or tablet), and/or one or more third-party integrations or interfaces 194 for other smart devices (e.g., virtual home assistant devices such as Amazon Echo® or Google Home™ devices), etc. Additionally or alternatively, one or more associated devices 195 (e.g., HVAC, air purifier, air humidifier, air dehumidifier, other devices such as from an original equipment manufacturer (OEM), other suitable environment-modulating devices, etc.) may be communicatively coupled to the network 180, for example to remedy environmental conditions based on sensor data obtained from the environment quality monitoring device 100, as further described below.

Housing and Mount

Figure 2A:
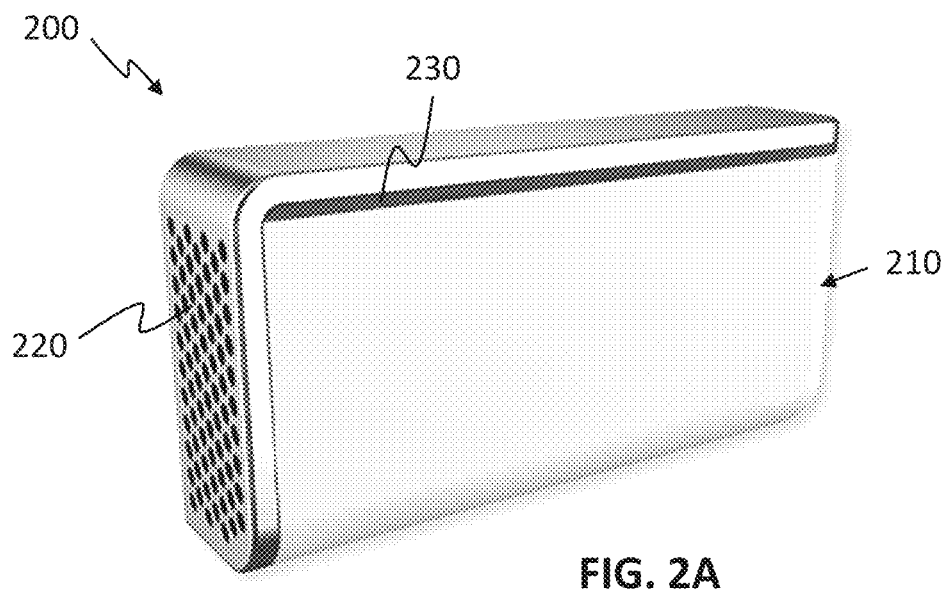
FIGS. 2A and 2B are left and right perspective views, respectively, of an exemplary variation of an environment quality monitoring device.
Figure 2B:
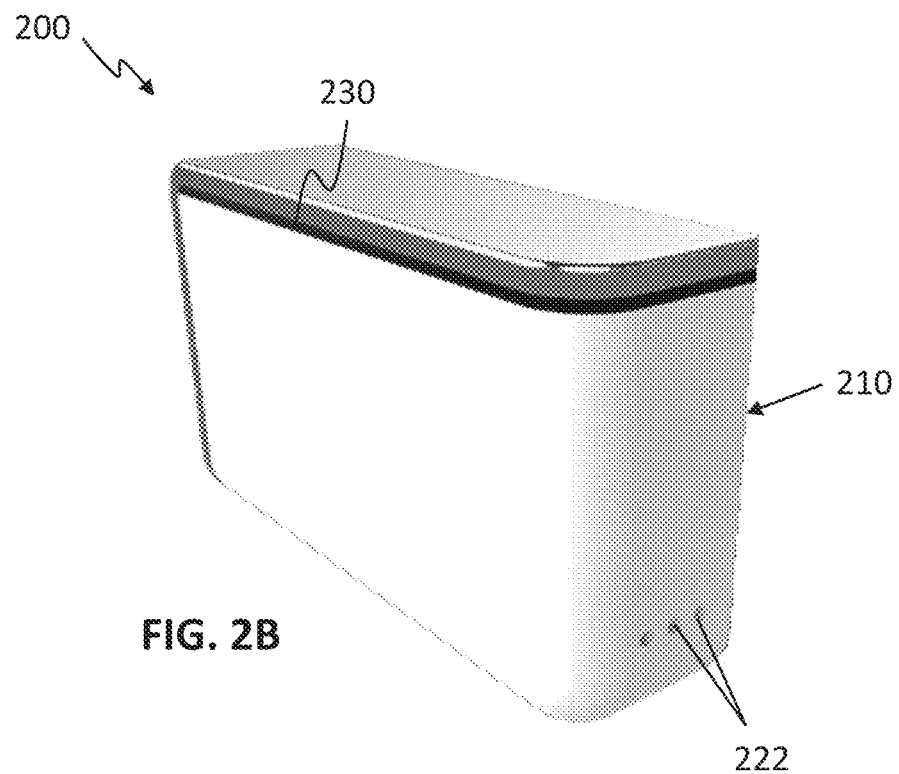

FIGS. 2A-2D illustrate one exemplary variation of an environment quality monitoring device 200. The environment quality monitoring device 200 includes a housing 210 for enclosing a plurality of sensors, including circulation vents 220 and 222 for allowing surrounding environment to enter and exit the housing. For example, environment may flow in and/or out of the housing through at least some of the vents 220 located on one end of the housing as shown in FIG. 2A, and additionally or alternatively environment may flow in and/or out of the housing through at least some of the vents 222. In some variations, circulation vents 220 and circulation vents 222 may be located generally at opposite ends of the device. Although vents 220 and 220 are depicted in FIGS. 2A and 2B as being generally circular, it should be understood that in other variations, the vents may have any suitable shape (e.g., elongated and slot-like). In some variations, at least some of the circulation vents 220 and 222 may further function to vent heat from electronic components to avoid overheating of the device 200.

Figure 2C:
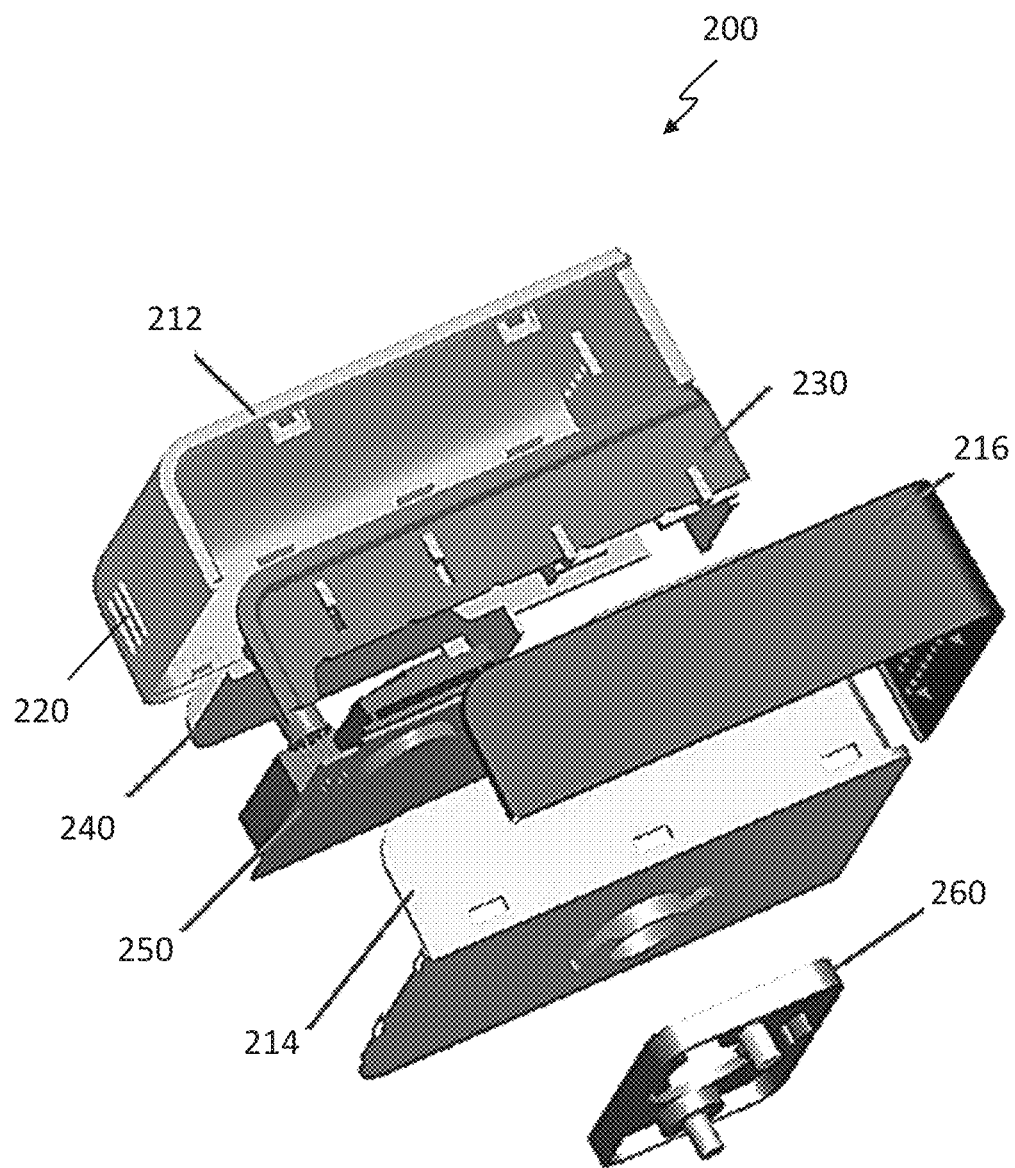
FIG. 2C is an exploded view of the environment quality monitoring device depicted in FIGS. 2A and 2B.

As shown in the exploded view of FIG. 2C, the housing 210 may include multiple components that coupled together, such as with interlocking mating features, fasteners (e.g., mechanical fasteners, epoxy), and/or other suitable coupling elements. For example, the housing may include a housing shell 212, a housing plate 214 coupled to the housing shell 212, and a lateral frame 216 configured to couple to the housing shell 212 and/or housing plate 214. The housing components may be manufactured in any suitable manner (e.g., injection molding, machine techniques, etc.).

Figure 2D:
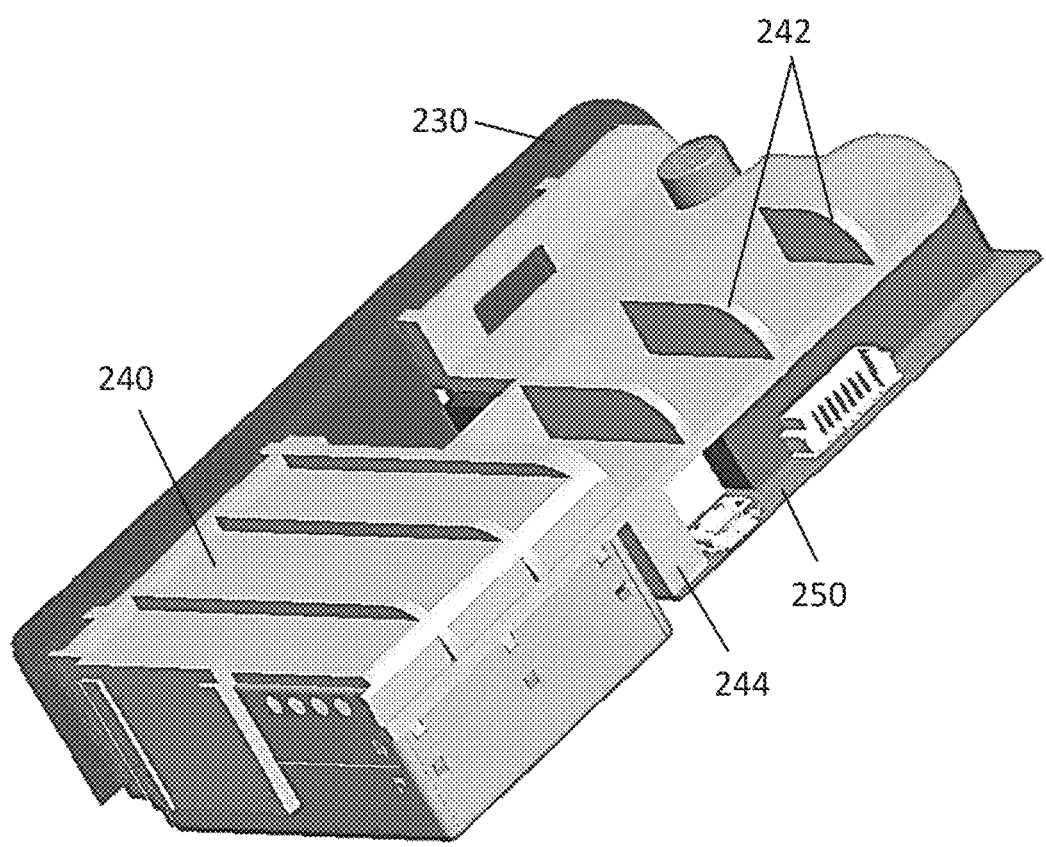
FIG. 2D is a perspective view of a partially assembled subassembly of the environment quality monitoring device depicted in FIGS. 2A and 2B.

Within the housing, sensors and other electronic components may be arranged on an electronics subsystem 250 (e.g., including one or more PCBAs) supported by a framework 240. The framework 240 may, for example, help stabilize the position of the sensors relative to the housing so as to reduce any effects that inconsistent sensor position may have on the sensor measurements (e.g., such that changes in sensor measurements are primarily due to changes in environment quality parameters, rather than shift in sensor position and how the sensor encounters environment). In some variations, the framework 240 may further isolate or segment the electronics subsystem 250 into at least two sections, including a sensor section and an additional electronics section (e.g., with a network communication device, processor, memory, etc.). For example, as shown in FIG. 2D, the framework 240 may include a dividing wall 244 to physically separate sensors from an additional electronics section. Such a dividing wall 244 may, for example, thermally isolate the sensors from the rest of the electronics (e.g., such that heat from the other electronics on one side of the dividing wall 244 does not significantly interfere with temperature measurements by sensors on the other side of the dividing wall 244.

In some variations, the housing may further include one or more features for indicating an alert related to environment quality. For example, the alert may be a visual alert configured to change appearance depending on the value of an environment quality score (e.g., calculated as described below) that is based at least in part on sensor data. As shown in the exemplary variation of FIGS. 2A and 2B, the housing may include a lighted indicator 230. The lighted indicator 230 may include a waveguide coupled to one or more light sources (e.g., one or more LEDs) and configured to propagate light from the one or more light sources. For example, the lighted indicator 230 may be coupled to light sources of multiple colors (e.g., red, yellow or orange, green, blue, etc.) that are selectively powered based on the value of the environment quality score, as described in further detail below. The color of light that is propagated in the waveguide (and therefore the visual appearance of the waveguide) depends on which colored light source is powered. Alternatively, the housing may include discrete light sources to communicate an environment quality score. In some variations, brightness of the displayed visual alert (e.g., color light intensity) may vary based on ambient light intensity. For example, a light sensor included in the environment quality monitoring device may detect intensity ambient light in the environment, and this information may be used to adjust intensity of the visual alert (e.g., the visual alert may be displayed brighter if ambient light conditions are dimmer, or displayed dimmer if ambient light conditions are brighter). Other visual indicators, such as a text or graphical display, may additionally or alternatively be used to indicate an environment quality score. Such indicators may additionally or alternatively be used to indicate other environment quality information, such as numerical environment quality parameter values or graphical representations thereof. Furthermore, as described below, other alerts may be communicated via other mediums, such as auditory alerts from a speaker (e.g., in the environment quality monitoring device, through a virtual home assistant device such as Amazon Echo® or Google Home™ devices), email or SMS text messages communicating alert information, etc.

Figure 3C:
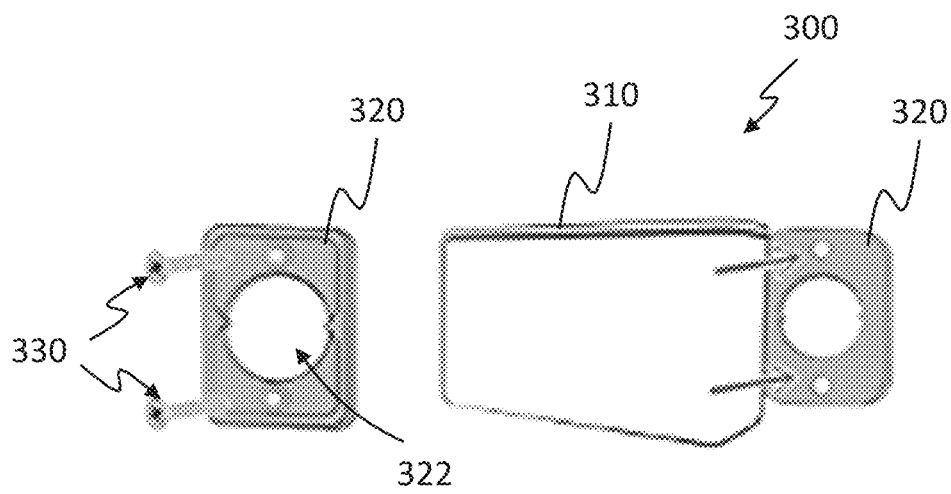
FIG. 3C is a rear perspective view of a coupling interface to the surface mount depicted in FIGS. 3A and 3B.
Figure 3C:
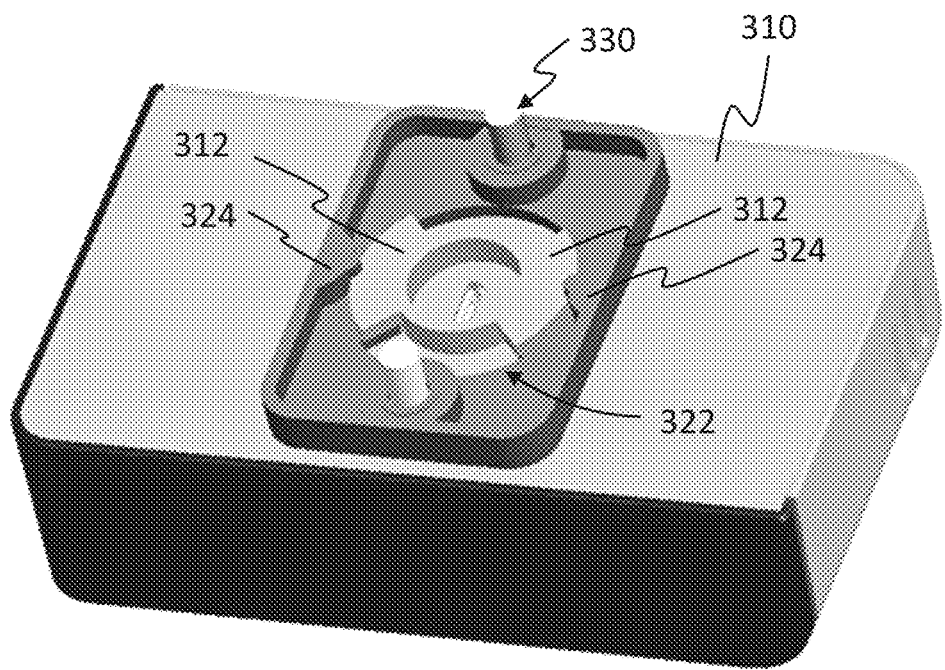

As shown in FIGS. 3A-3C, in some variations an environment quality monitoring device 300 may include a mount 320. In some variations, the mount 320 may be a surface mount such as a plate or other suitable intermediary structure for coupling the housing of the device 300 to a surface. For example, as shown in FIG. 3A, the mount 320 may include fastener holes for receiving fasteners 330, which may couple the mount 320 to a surface (e.g., vertical surface such as a wall). In some variations, the mount 320 may include one or more level devices (e.g., bubble level) to help a user position the mount 320 in a horizontally level orientation. As shown in FIG. 3B, the housing 310 may couple to the mount 320, such that the housing 310 is fixed relative to the surface. For example, as shown in FIG. 3C, the housing 310 may include a mount engagement feature 312 configured to mate within a receiving holes 322 in the mount 320 in interlocking or interference fashion. In some variations, the housing 310 may be removably coupled to the mount 320. For example, the housing 310 and the mount 320 may have respective engagement features such as mount engagement features 312 on the housing and tabs 324 on the mount that are selectively operable in an engaged state and a disengaged state. As an illustrative example, the mount 320 may be coupled to a mounting surface (e.g., wall), and the housing 310 may be placed over the mount 320, then rotated (e.g., 90 degrees) such that the mount engagement features 312 slide under and engage tabs 324. However, other suitable engagement features (e.g., threads, other interference features, etc.) may provide coupling between the housing 310 and the mount 320.

Figure 3D:
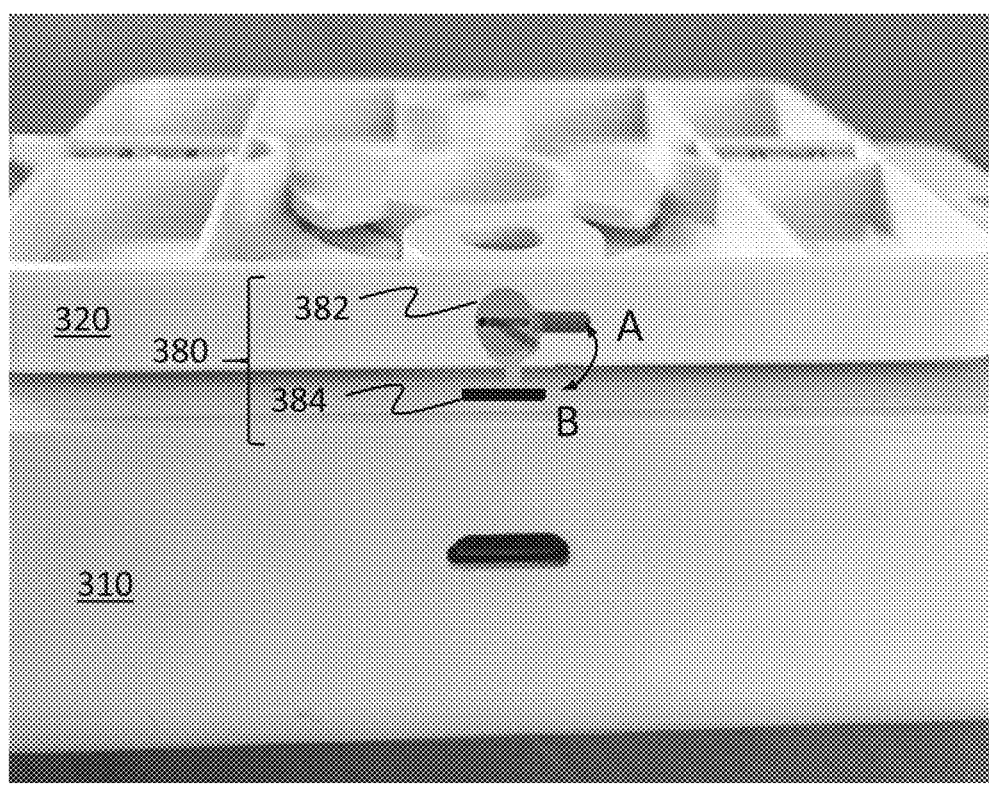
FIG. 3D is a lower perspective view of an exemplary variation of an environment quality monitoring device and surface mount with a schematic of a locking mechanism.

In some variations, as shown in FIG. 3D, the environment quality monitoring device may include one or more locking mechanisms 380 to further secure the connection between the housing 310 and the mount 320. A locking mechanism 380 may include an unlocked configuration (which more easily permits decoupling of the housing 310 from the mount 320), and a locked configuration (which helps prevent decoupling of the housing 310 from the mount 320). For example, a locking mechanism 380 may include a rotatable latch 382 engageable with a notch 384 or other recess. As shown in FIG. 3D, the rotatable latch 382 may movable between a Position (A) in which the latch 382 is disengaged from the notch 384, and a Position (B) in which the latch 382 may be engaged with the notch 384. When the latch 382 is in Position (B), the housing 310 may be further secured to the mount 320 to, for example, help prevent tampering or inadvertent removal. For example, as described above, the housing 310 may couple to the mount 320 by rotating relative to the mount 320 until the mount features 312 slide under the tabs 324. After the rotatable latch 382 is moved to engage the notch 384 (Position (B)), the locking mechanism 380 may substantially prevent reverse rotation of the housing 310 relative to the mount 320, thereby providing a more secure connection between the housing 310 and the mount 320. It should be understood that the variation of the locking mechanism shown in FIG. 3D is exemplary only, and that other variations of locking mechanisms may include other suitable mechanisms such as sliders, hinged members, etc.

In other variations, the housing 310 may be coupled to the mount 320 via fasteners or other suitable coupling features. The mount engagement feature 312 and/or mount 320 may include one or more detents (e.g., arranged at 45-degree increments, 90-degree increments, etc. around the receiving hole 322) to help orient and lock the housing 310 relative to the mount 320 in any of one or more predetermined relative orientations. Such detents may, for example, help ensure that the housing 310 (and overall device 300) is oriented in an aesthetically pleasing manner (e.g., horizontally level with the mount 320).

In other variations, the environment quality monitoring device 300 may include other kinds of mounts for stabilizing the device at a selected location, such as a rear stand, tripod, base plate, etc. A mount may be collapsible and expandable. In yet other variations, the device may be free-standing without a mount (e.g., rest on a flat face of the housing on a surface).

Figure 4A:
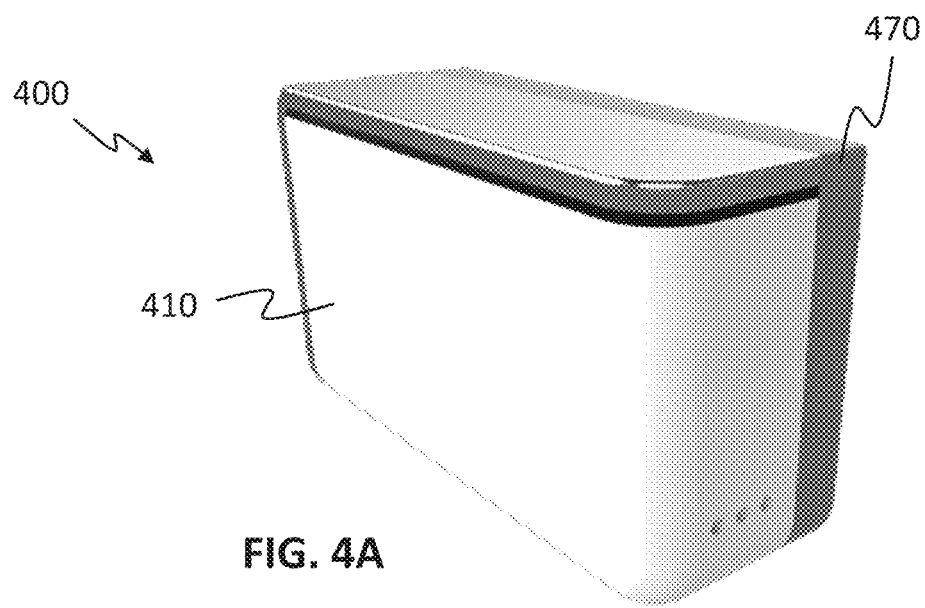
FIG. 4A is a perspective view of a variation of a mount with a power source assembly.
Figure 4B:
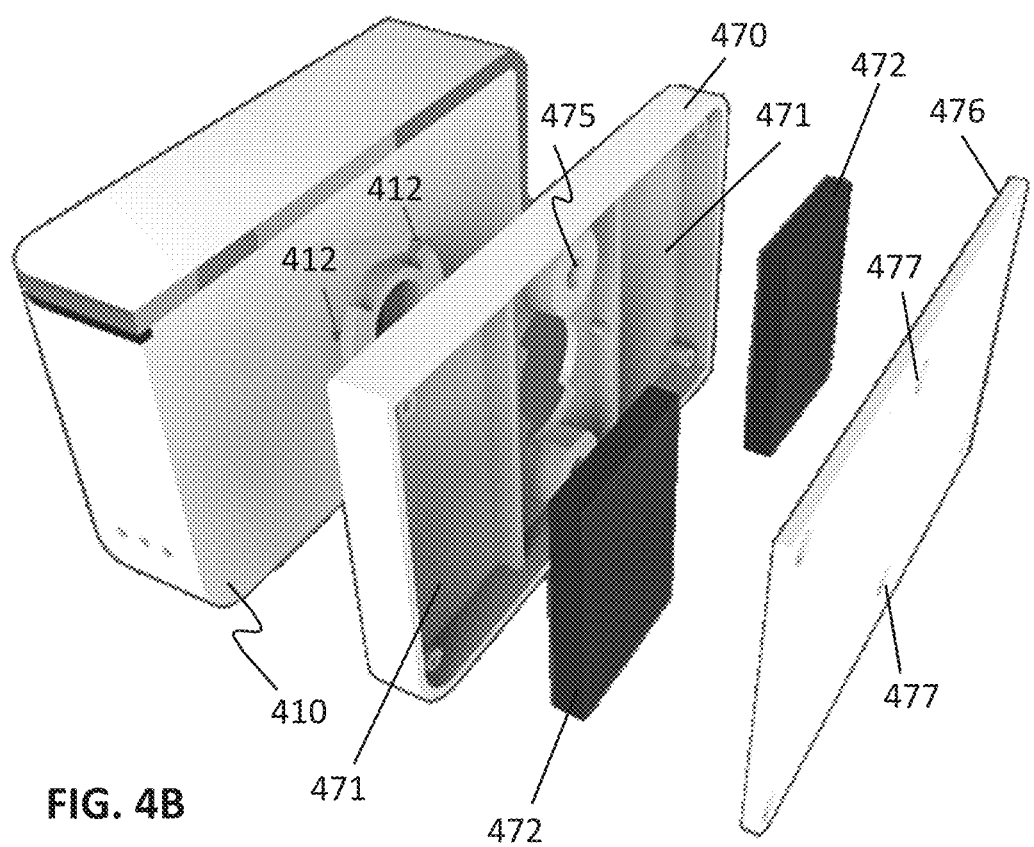
FIG. 4B is an exploded view of the mount depicted in FIG. 4A.

In the exemplary variation as shown in FIGS. 4A and 4B, an environment quality monitoring device 400 may include a mount 470 comprising one or more power sources. The mount 470 may be coupled to a surface (e.g., wall) in a manner similar to the mount 320 described above with respect to FIGS. 3A-3C. For example, the mount 470 may include fastener holes 475 and 477 for receiving fasteners to couple the mount 470 to a surface (e.g., a wall). However, in contrast to the mount in FIGS. 3A-3C, the mount 470 may include at least one compartment 471 for receiving one or more batteries 472, and a back plate 476 for enclosing the batteries within the compartments 471. The back plate 476 may be removable to provide easy access to the compartments 471, such as to facilitate replacement or recharging of the batteries 472. The housing 410 may be coupled to the mount 470, and may include contacts (e.g., incorporated into a mounting feature on the housing 410) that are configured to draw power from the batteries 472 when the housing 410 is coupled to the mount 470, thereby powering the device 400. By placing batteries 472 in the mount 470 instead of within the housing 410, the batteries may advantageously be more easily replaced or recharged without requiring disassembly of the housing 410. Additionally or alternatively, in some variations, the environment quality monitoring device may be coupled to an external power source via a wired connection (e.g., USB connection, etc.).

In some variations, an environment quality monitoring device may be configured for indoor and/or outdoor use. For example, FIGS. 19A-19G illustrate an exemplary variation of an environment quality monitoring device 1900, which may be configured to indoor and/or outdoor use. Similar the environment quality monitoring devices described above, the environment quality monitoring device 1900 may include a housing including a housing body 1914 and a mount 1960 that may enable the device 1900 to be mounted to a suitable structure (e.g., wall, pole, etc.). The housing body 1914 may include at least one cavity or other suitable recess that houses one or more sensors, electronics, and/or other suitable components as described in further detail below.

Figure 19A:
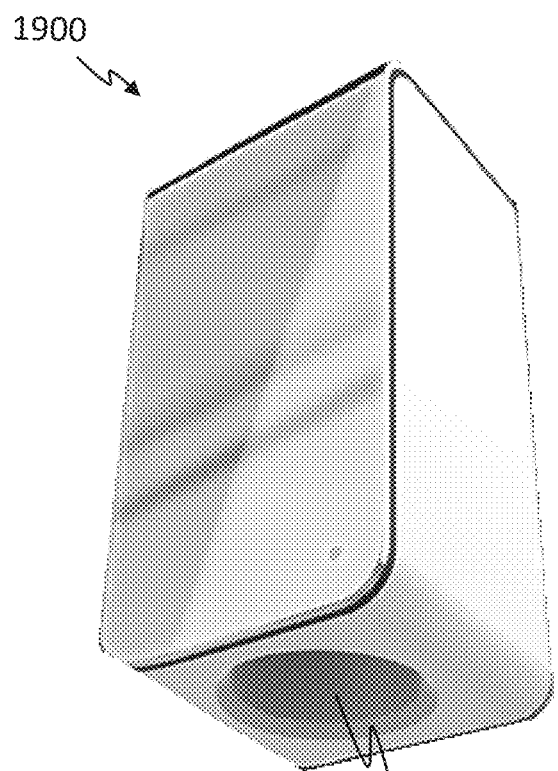
FIGS. 19A and 19B are lower and upper perspective views, respectively, of an exemplary variation of an environment quality monitoring device.
Figure 19B:
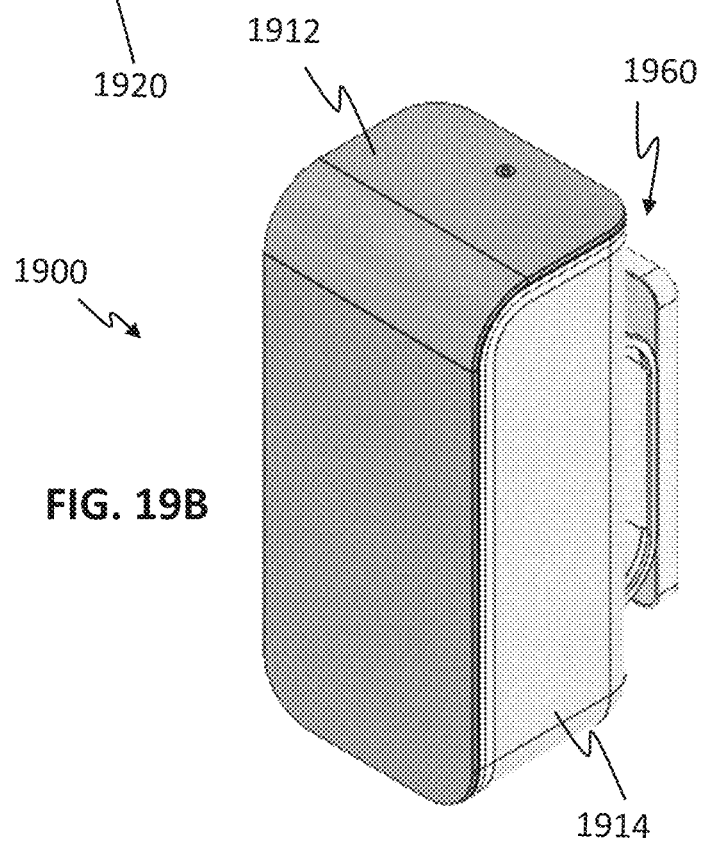
Figure 19C:
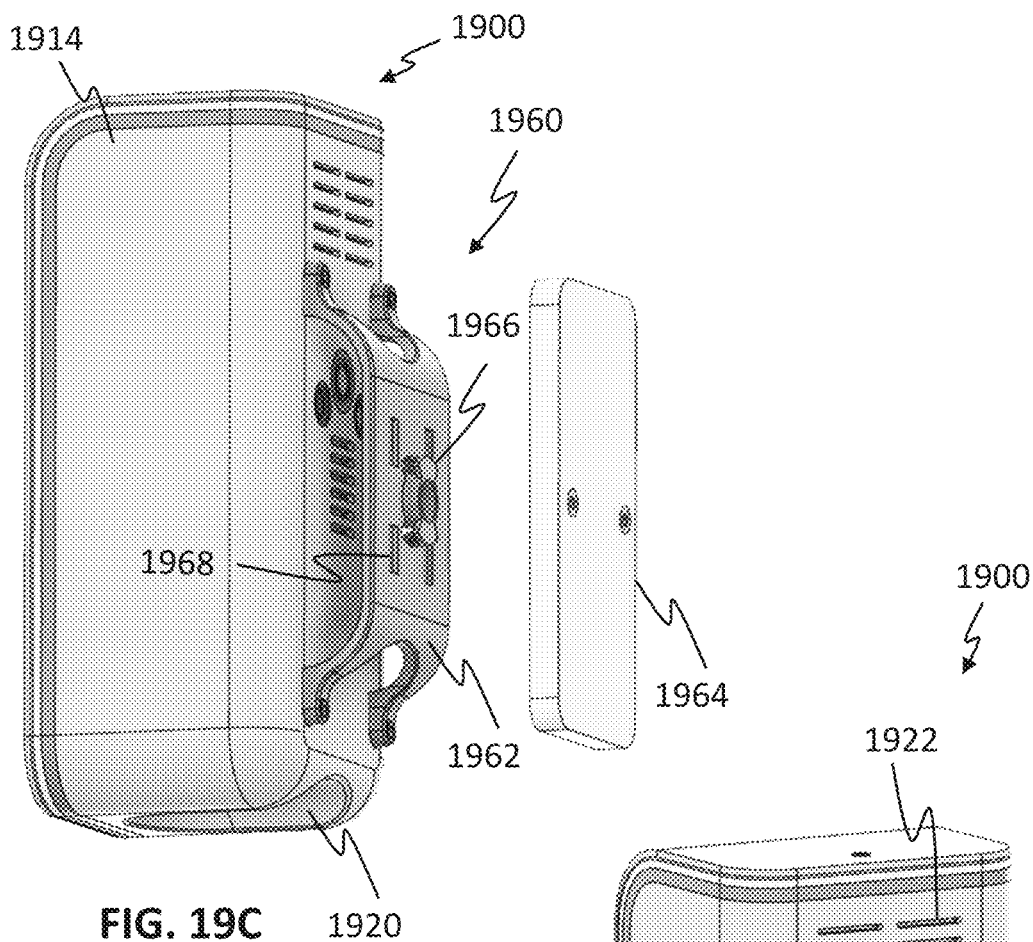
FIGS. 19C and 19D are rear perspective views of an exemplary variation of an environment quality monitoring device.
Figure 19D:
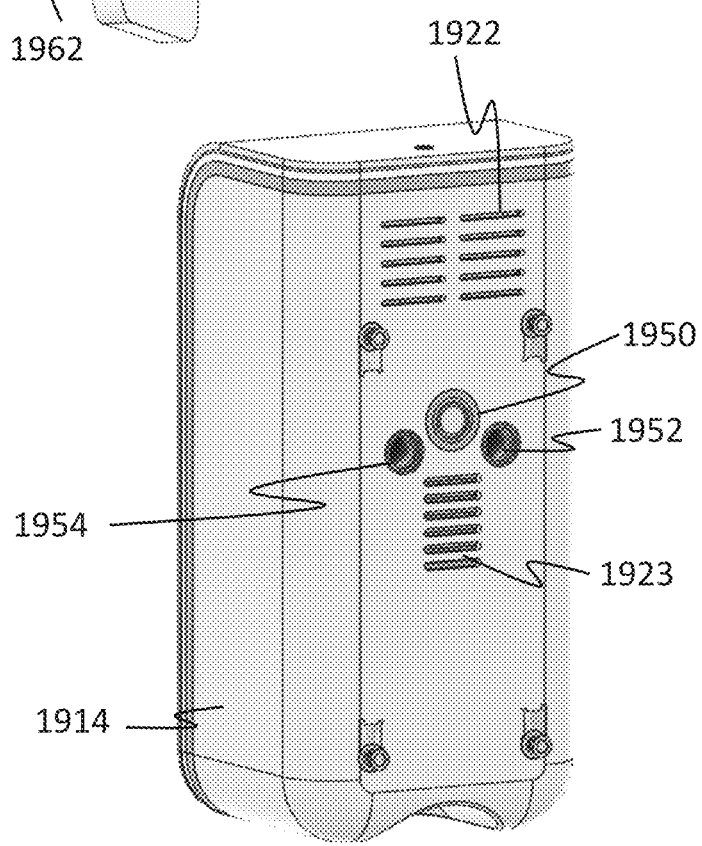

As shown in FIGS. 19C and 19D, the mount 1960 may include one or more suitable mount features to enable placement of the environment quality monitoring device 1900 on a surface. For example, in some variations, the mount 1960 may include a mount bracket 1962 coupled to a rear face of the housing body 1914. The mount bracket 1962 may include one or more mount engagement features 1966 that engage with one or more mating features on a mount plate 1964 (e.g., similar to that described above with respect to FIG. 3C). The mount plate 1964 may be coupled to a suitable mounting surface (e.g., wall), such that when the mount bracket 1962 is coupled to the mount plate 1964 (e.g., via one or more mount engagement features 1966), the environmental quality monitoring device 1900 may be coupled to the mounting surface. The mount bracket 1962 may, in some variations, be coupled to the housing body 1914 as shown in FIG. 19C (e.g., with one or more fasteners, with interlocking mating features, with an engineering fit, etc.) or integrally formed with the housing body 1914. In some variations, the mount bracket 1962 may have an arched or otherwise raised profile, such as to enable airflow or air circulation between the housing body 1914 and the mount bracket 1962 (e.g., to enable airflow in and/or out of circulation vents 1923 as shown in FIG. 19D). Additionally or alternatively, the mount bracket 1962 may include other suitable mount features, such as one or more mounting slits 1968 or other openings which may receive straps (e.g., metal, plastic, or elastic straps) that may be secured around a mounting surface (e.g., pole) to thereby couple the environment quality monitoring device 1900 to the mounting surface. While mount features (e.g., mount engagement features 1966, mounting slits 1968, etc.) may be on a mount bracket 1962 as shown in FIG. 19C, it should be understood that in some variations, one or more mount engagement features 1966 may be on the housing body 1914 (e.g., coupled to the housing body 1914 or integrally formed with the housing body 1914).

Furthermore, in some variations the environment quality monitoring device may be mounted in any suitable manner. In some variations, the environment quality monitoring device 1900 may be hung (e.g., via one or more straps), or configured to rest on a surface. Additionally or alternatively, the environment quality monitoring device 1900 may include or be coupled to a stand (e.g., fold-out stand, legs, etc.). Accordingly, in some variations, one or more mount features may be arranged on any suitable portion of the environment quality monitoring device (e.g., upper, lower, lateral sides, front, etc.).

In some variations, a rear face of the housing may further include one or more connectivity and/or operational interface elements. For example, as shown in FIG. 19D, the environmental quality monitoring device 1900 may include a power on/off button 1950 (or toggle switch, slide switch, etc.) configured to alter the operating state and/or mode of the environmental quality monitoring device 1900. As another example, the environmental quality monitoring device 1900 may include one or more power connectivity ports 1952 (e.g., for supplying direct power to the device 1900 such as from an external power source, or for recharging a battery (described in further detail below), etc.). As another example, the environmental quality monitoring device 1900 may include one or more communication ports 1954, such as for wired data input and/or output for communication with electronics arranged inside the housing (e.g., sensor data transfer, software or firmware updates, calibration, etc.). Although connectivity and operational interface elements are shown in FIG. 19D as on a rear face of the housing, it should be understood that such elements may be arranged on any suitable portion of the housing (e.g., front, top, bottom, sides, etc.).

As shown in FIG. 19B, the environment quality monitoring device 1900 may include a housing cover 1912. The housing cover 1912 may be coupled to the housing body 1914 (e.g., via one or more fasteners, such as one or more mechanical fasteners and/or adhesive, or interlocking features, engineering fit, etc.) or may integrally coupled to the housing body 1914 so as to substantially enclose or surround the internal contents of the housing (e.g., sensors, electronics). In some variations, the housing cover 1912 which may function as a weather shield. For example, the housing cover 1912 may include an upper surface and/or front-facing surface that helps shelter the internal contents of the housing from sunlight. For example, the housing cover 1912 may include a UV-treated surface and/or reflective coating to reduce absorption of heat. Additionally or alternatively, one or more outer portions of the housing (e.g., outer portion of housing body 1914) may include a thermally conductive material (e.g., metal) that functions as a heat sink, and an insulated layer may be arranged between the outer portion of the housing and the inner contents of the housing. The housing cover 1912 may further function to help shelter the internal contents of the housing from other weather elements such as wind, rain, hail, etc. (e.g., hard materials resistant damage by impact). Alternatively, a similar weather shield may be coupled to the housing cover 1912. For example, a weather shield may be a separately formed component that is coupled to the housing cover 1912 (e.g., formed by injection molding, milling, 3D printing, or the like and then coupled to the housing cover 1912 via one or more fasteners, or applied as a protective film or coating to the housing cover 1912). Furthermore, a weather shield may additionally or alternatively be coupled to or integrally formed with other suitable portions of the housing, such as the housing body.

Figure 19E:
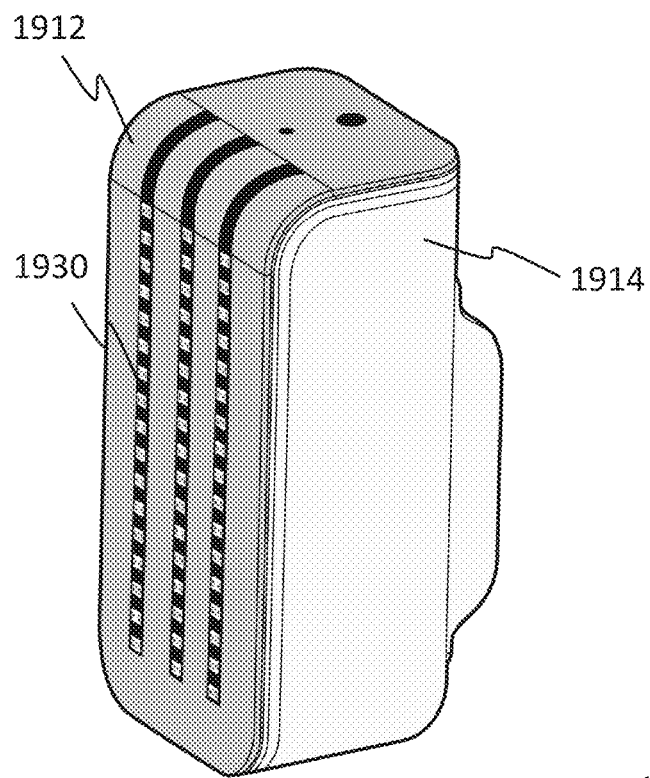
FIGS. 19E and 19F are front perspective views of an exemplary variation of a housing cover with indicators.
Figure 19F:
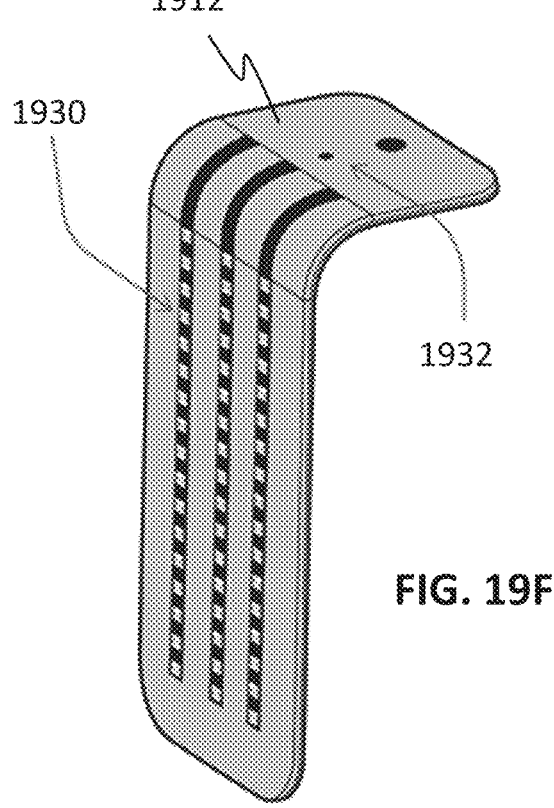

Additionally or alternatively, in some variations, the housing cover 1912 (or other suitable portion of the housing) may include one or more indicators for communicating information about ambient environment and/or device status. For example, as shown in FIGS. 19E and 19F, in some variations the housing cover 1912 (or component coupled thereto) may include one or more visual indicators such as lighted indicators 1930. The lighted indicators 1930 may include LEDs, waveguides, and/or any suitable kind of illumination. In some variations, the lighted indicators 1930 may extend along the front face (or other suitable surface) of the housing cover 1912, such as in shapes with a large surface area (e.g., elongated shape) that may be easily visible from a distance. Such lighted indicators 1930 may, for example, be activated to convey visual alerts based on measurements performed by the device 1900 or other nearby environment quality monitoring devices (e.g., operating collectively as part of an environment quality monitoring system). Similar to the lighted indicator described herein with respect to FIGS. 2A and 2B, the lighted indicators 1930 may be color-coded to indicate various degrees of alerts, programmed to illuminate in various suitable temporal and/or spatial patterns, etc. The nature of such alerts (e.g., thresholds, desired visual patterns, etc.) may, for example, be configured through a web portal, mobile application, API, etc.

As another example, as shown in FIG. 19F, in some variations the housing cover 1912 (or component coupled thereto) may include one or more audible indicators 1932, such as a speaker, buzzer, and/or the like. The audible indicator 1930 may, for example, be activated to convey audible alerts based on measurements performed by the device 1900 or other nearby environment quality monitoring devices (e.g., operating collectively as part of an environment quality monitoring system). Similar to the lighted indicator described herein with respect to FIGS. 2A and 2B, the lighted indicators 1930 may be color-coded to indicate various degrees of alerts, programmed to illuminate in various suitable temporal and/or spatial patterns, etc. The audible indicator 1932 may be configured to emit verbal cues (e.g., words, announcements) and/or non-verbal cues (e.g., tones, buzzers, beeps, music, etc.).

Figure 19G:
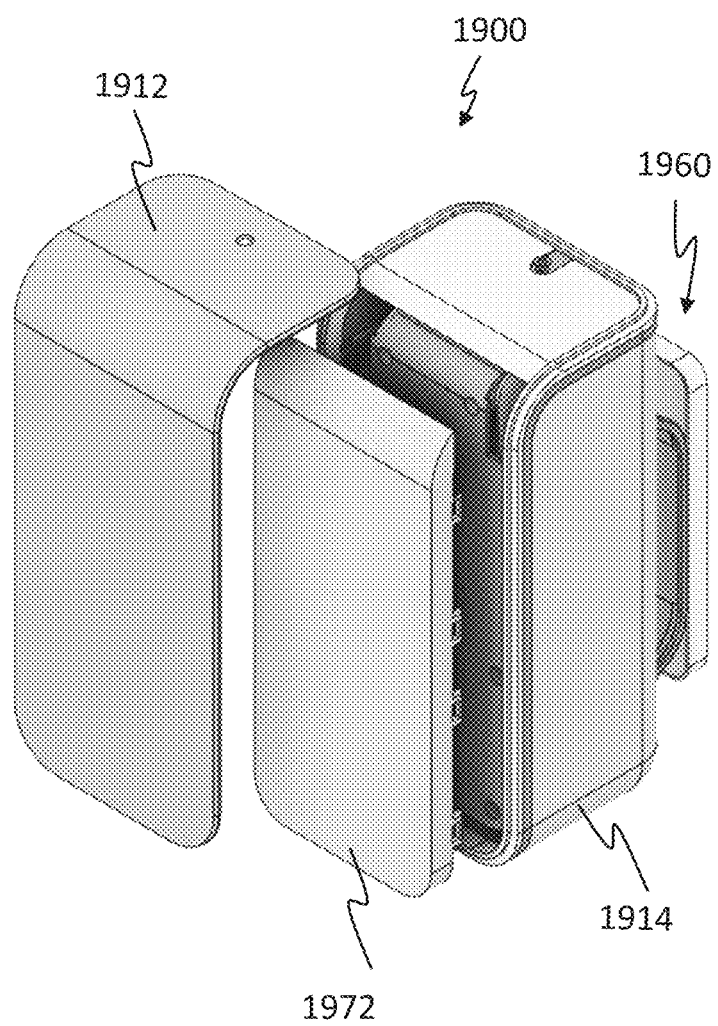
FIG. 19G is a partially exploded view of an exemplary variation of an environment quality monitoring device.

As shown in FIG. 19G, the housing cover 1912 may be removable to permit access to contents of the housing. For example, removal of the housing cover 1912 may enable access to a battery 1972 that functions as a power source for the sensors, electronics and/or other components of the housing requiring power. In some variations, the battery 1972 may be rechargeable (e.g., via power connectivity port 1952), and/or may be replacement (e.g., swapped with a new battery). For example, the battery 1972 may be charged from a suitable external power source (e.g., 12V power source), from a solar panel, etc. The battery 1972 may, in some variations, function as a primary power source (e.g., periodically recharged as appropriate), or may be function as a secondary power source used in combination with another primary power source (e.g., external power source). For example, the battery 1972 as a secondary power source may be continuously maintained at a sufficient charge level so as to help ensure continuous operation of the device 1900 in the event of a power outage or other loss of power from a primary power source. Additionally or alternatively, the environment quality monitoring device 1900 may include multiple batteries (e.g., for redundancy, expanded run time, etc.).

Figure 20:
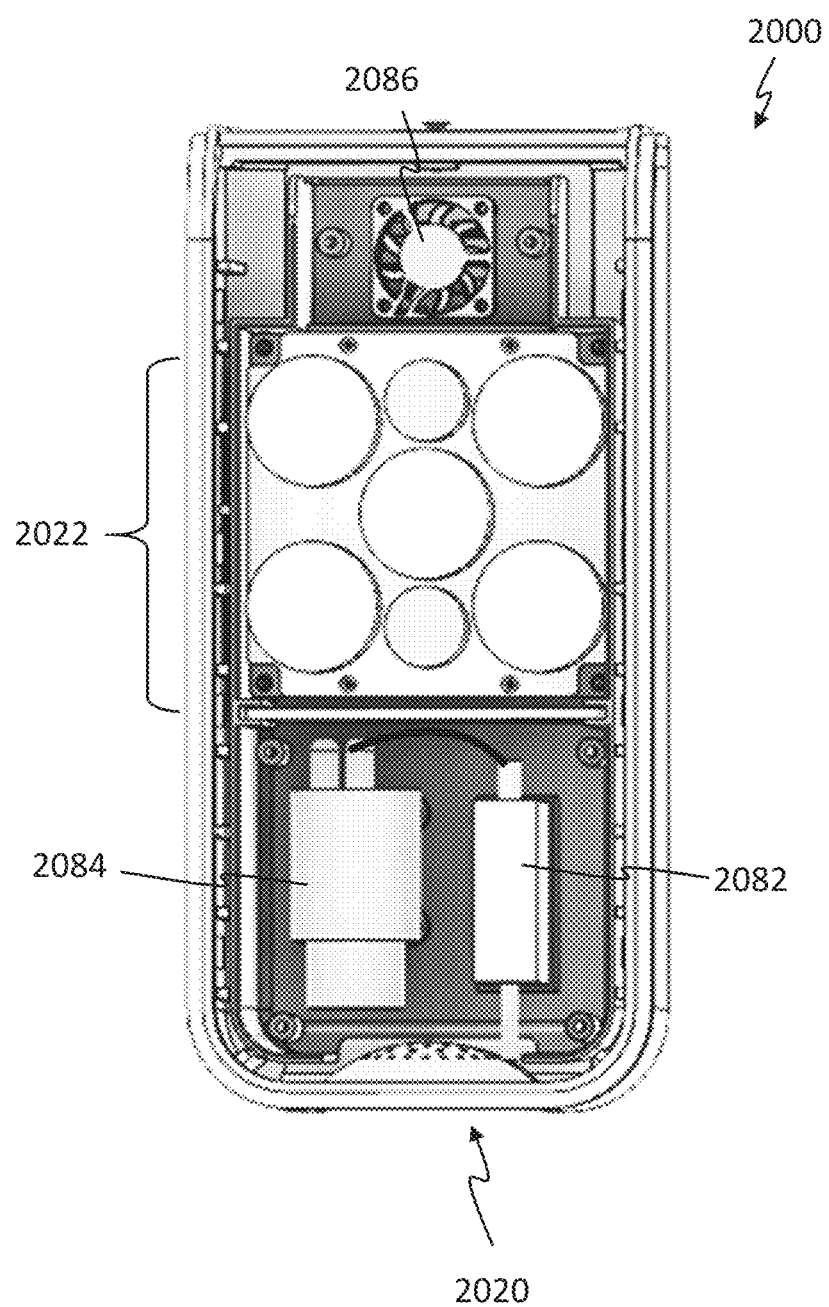
FIG. 20 is an illustrative schematic of an interior of an exemplary variation of an environment quality monitoring device.

As described above, various sensors and/or electronics may be contained within the housing of the environment quality monitoring device 1900. Such sensors may include high precision sensing elements, such as those described in further detail below. The internal components may be arranged within the housing in any suitable manner. By way of illustration, FIG. 20 depicts an exemplary layout of one or more (e.g., seven) gas sensors 2022 and/or one or more particulate sensors 2082 in the housing. In some variations, the housing may additionally or alternatively contain one or more environmental condition sensors (e.g., temperature, humidity, pressure, noise, etc.). Air may enter the housing through one or more circulation vents, such as intake 2020. Air may also exit the housing through one or more circulation vents, such as vents (e.g., similar to vents 1922 and 1923 as shown in FIG. 19D). In some variations, the housing may contain one or more exhaust fans 2086 that may function to draw air over the one or more gas sensors 2022.

Additionally or alternatively, the housing may contain one or more pumps 2084 that may function to direct air over or into one or more particular sensors 2082. In some variations, pump and/or fan speed (or on/off state) may be adaptively controlled on one more measured parameters or environmental conditions (e.g., pollution level, weather such as rain), such as to protect the environment quality monitoring device and/or extend the longevity of the device and/or its sensors.

In some variations, some or all of the sensors within the housing of an environment quality monitoring device may be interchangeable. For example, with reference to FIG. 20, one or more sensors (e.g., gas sensors 2022) may be replaced by another sensor of the same type (e.g., upon saturation or other expiration of use) and/or by a different kind of sensor. Accordingly, the combination of sensors within the environment quality monitoring device may be customized or tailored in a modular manner for a particular application by including a particular suite of sensors. Furthermore, in some variations the environment quality monitoring device may be configured to automatically detect the type and/or setting of sensors that are arranged within the housing, and configure the device accordingly. In an example variation, the environmental quality monitoring device may function as a gas monitor (e.g., up to about 7 slots for gas sensors to be used simultaneously), as a particulate matter monitor (e.g., up to about six channels), and/or as an environmental monitor measuring other environmental conditions such as temperature, humidity, pressure, and/or noise.

Figure 21A:
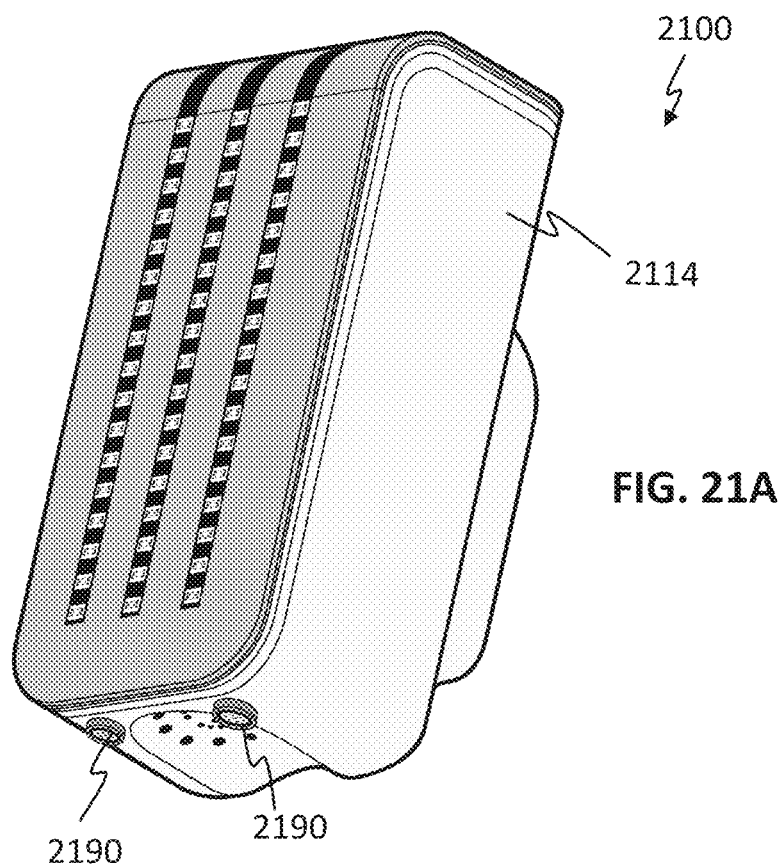
FIGS. 21A and 21B are rear perspective and bottom views, respectively, of an exemplary variation of an environment quality monitoring device with connectors for external sensors.
Figure 21B:
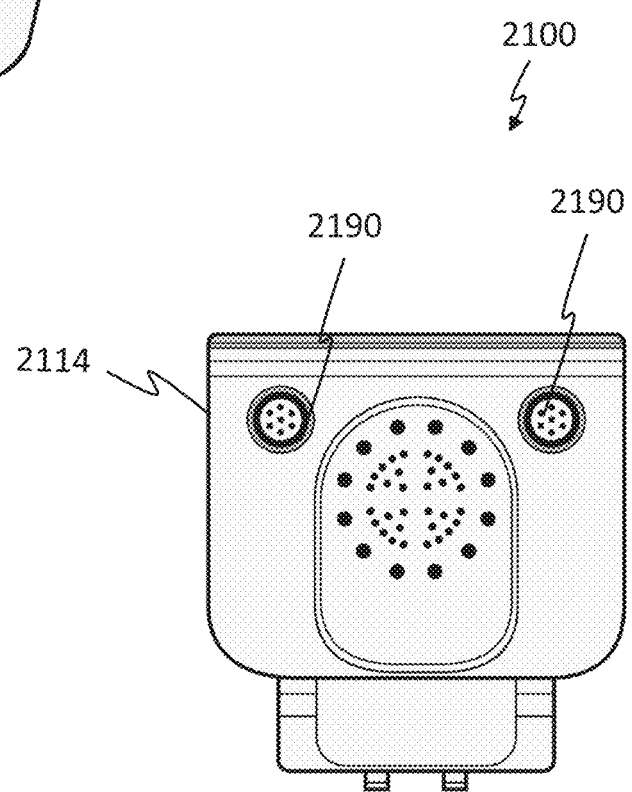

Additionally or alternatively, in some variations an environment quality monitoring device may include one or more sensors mounted to an external portion of the housing. For example, as shown in FIGS. 21A and 21B, an environment monitoring device 2100 may include one or more connectors 2190 for coupling external sensors. External sensors may include, for example, pressure sensors, sound intensity sensors, light intensity sensors, humidity sensors, heat stress monitoring sensors, etc. such as those sensors described in further detail below. The external sensors may be coupled to the housing 2114 via one or more fasteners (e.g., adhesive), engineering fit (e.g., snap fit), or in any suitable manner. Furthermore, although the external sensors 2114 are shown in FIGS. 21A and 21B as located on a bottom surface of the device 2100, it should be understood that one more external sensors may additionally or alternatively be located on any suitable surface of the device 2100 (e.g., front, top, sides, rear, etc.).

Figure 17:
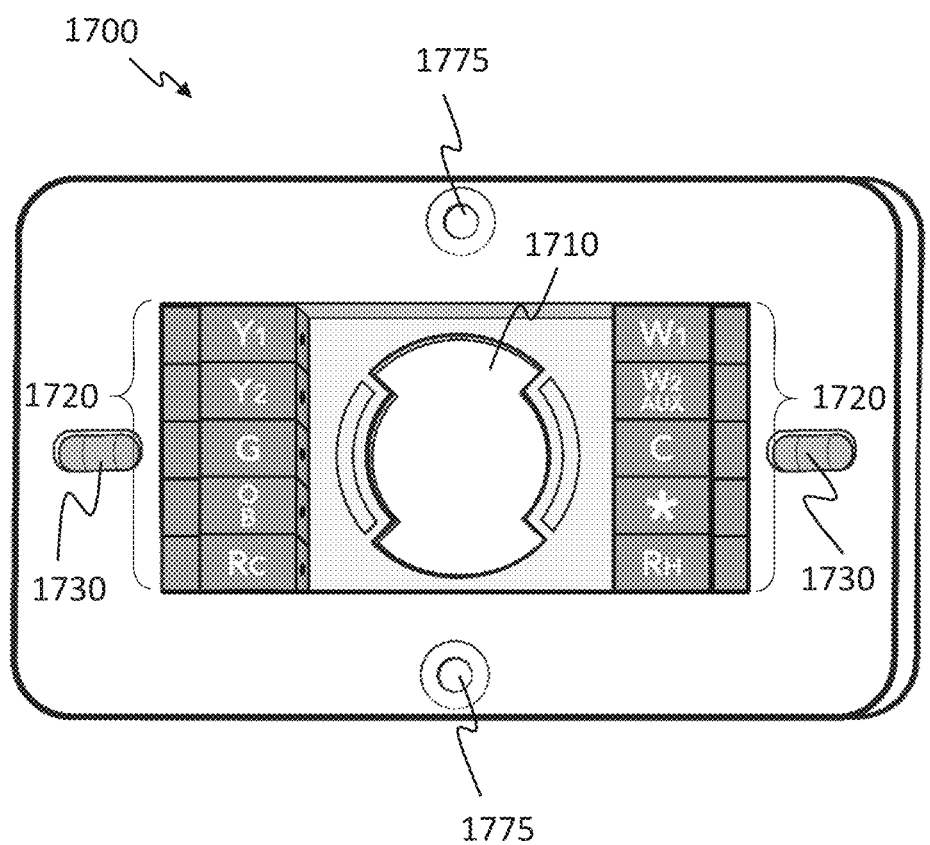
FIG. 17 is an illustrative schematic of a mount configured to interface with an HVAC system.

In some variations, an environment quality monitoring device may include a mount configured to enable the monitoring device to interface with a heating, ventilation and air conditioning (HVAC) system. For example, as shown in FIG. 17, a mount 1700 may include suitable inputs 1720 for receiving and securing wires that control an HVAC system. In such variations, the mount 1700 may enable the environment quality monitoring device to control a connected HVAC system, such as in response to environment parameter measurements and/or environment quality score (as described in further detail below). Inputs 1720 may include, for example, conventional inputs such as control wires ($Y_1$, $Y_2$) for a cooling system, control wires ($W_1$, $W_2$) for a heating system, a control wire (G) for a fan, a control wire (O/B) for a changeover valve for switching between heating and cooling, a common ground wire (C), and/or power wires ($R_C$, $R_H$), etc. to enable the environment quality monitoring device to be retrofit onto existing conventional HVAC systems. The mount 1700 may further include fastener holes 1775 for receiving fasteners to couple the mount 1700 to a mount surface (e.g., a wall), and a device receiving hole 1710 configured to mate with a feature of the environment quality monitoring device (e.g., mount feature 412 as shown in FIG. 4B). Additionally or alternatively, the mount 1700 may include other suitable features to assist mounting, such as bubble levels 1730 to help guide horizontal alignment of the mount.

Accordingly, in some variations the environment quality monitoring system may include a controller configured to apply one or more various algorithms (e.g., artificial intelligence and/or machine learning algorithms) to optimize or otherwise control certain environmental conditions (e.g., those affected by temperature and/or humidity) directly by applying changes to the HVAC system. In these variations, the environment quality monitoring device may eliminate the need for a separate device such as a thermostat for controlling aspects of the environment. Furthermore, in some environments, multiple environment quality monitoring devices may interface with multiple HVAC control units (e.g., in multiple rooms) and allow the HVAC units to be network-connected via the cloud. Multiple environment quality monitoring devices may thus optimize or otherwise control environmental conditions based on various parameters (e.g., event detection such as occupancy, environment quality parameters such as temperature or humidity, user profiles, etc. as described in further detail below), such as via artificial intelligence and/or machine learning techniques.

Sensors

Figure 5A:
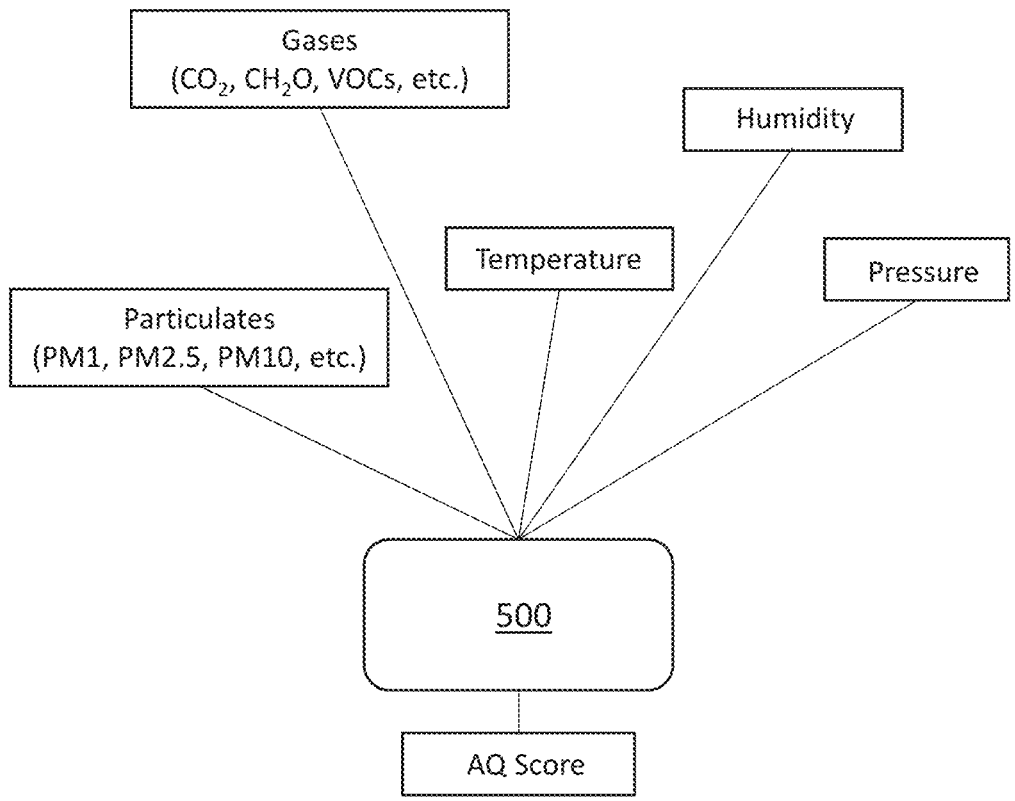
FIG. 5A is an illustrative schematic of information flow for an exemplary variation of an environment quality monitoring device.

As shown in the schematic of FIG. 5A, the environment quality monitoring device 500 may include a plurality of sensors configured to measure a variety of environment quality parameters. The environment quality parameters may be continuously measured so as to provide a real-time or near real-time assessment of ambient environment quality. Sensors may provide sensor data at any suitable sampling frequency. For example, sensor data may be sampled between about 1 and about 20 times per minute, between about 1 and about 10 times per minute, between about 1 and about 5 times per minute, between about 3 and 10 times per minute, between about 3 and about 6 times per minute, or between about 3 and about 5 times per minute.

In some variations, the environment quality monitoring device 500 may sample data from some or all of its sensors multiple times per minute, and may periodically (e.g., once every minute, or more than once every minute) communicate updated sensor data to a cloud network, server, etc. as further described herein. For example, in some variations every parameter may be reported once per minute (or other suitable interval) as an average of several sample measurements performed within that minute. In some variations, the device 500 may continue sampling sensor data and store such data in its local memory, even in the event of a network outage or other communication failure. Once the network connectivity is thereafter reestablished, then all of the sensor data may be uploaded or pushed to the cloud network, server, etc.

For example, in some variations, the environment quality monitoring device 500 may include one or more sensors configured to measure amount of particulate matter (PM), such as dust, fungi, bacteria, viruses, and pollen, and combustion particles. Generally, the smaller these particulates are, the worse they are for health. Furthermore, smaller particulates are harmful because they linger in the atmosphere for longer (e.g., weeks), are freely transported by environment currents. For example, bacteria can cause infection after being released by coughs and/or sneezes. Accordingly, in some variations the environment quality monitoring device can include sensors that distinguish between different sizes of particulate matter. For example, the environment quality monitoring device includes sensors for measuring respective amounts (e.g., concentration, such as $\mu g/m^3$) of various sizes. For example, sensors may measure levels of PM10 (particulate matter that is about 10 $\mu m$ or less in diameter, such as dust, pollen, or mold), PM2.5 (particulate matter that is about 2.5 $\mu m$ or less in diameter, such as combustion particles) and/or PM1 (particulate matter that is about 1 $\mu m$ or less in diameter, such as viruses).

In an exemplary variation, the environment quality monitoring device measures all three categories of PM10, PM2.5, and PM1, thereby providing a highly-precise measurement of particulate matter in the ambient environment. Specifically, the environment quality monitoring device may include a first sensor configured to detect PM10 particulates between about 2.5 $\mu m$ and about 10 $\mu m$ in diameter, a second sensor configured to detect PM2.5 particulates between about 1 $\mu m$ and about 2.5 $\mu m$ in diameter, and PM1 particulates below about 1 $\mu m$ in diameter (e.g., between about 0.3 $\mu m$ and 1 $\mu m$ in diameter). These particulate sensors may, for example, be included in an air quality monitoring module in the environment quality monitoring device. Each particulate matter sensor can have an effective measurement range of, for example, about 0 $\mu g/m^3$ to about 500 $\mu g/m^3$ and a resolution of about 1 $\mu g/m^3$. In some variations, the environment quality monitoring device (e.g., air quality monitoring module) may include sensor technology utilizing laser scattering to measure particulate matter.

Additionally or alternatively, the environment quality monitoring device may include one or more sensors configured to measure an amount of at least one gas in ambient environment. Elevated levels of certain gases can cause negative health effects. For example, elevated levels of carbon dioxide ($CO_2$) increases the likelihood of sleepiness, distraction, and lethargy, which in turn affects productivity, concentration, and work performance. In some variations, the environment quality monitoring device may include one or more sensors using non-dispersive infrared (NDIR) technology to detect $CO_2$. Volatile organic compounds (VOCs) are chemicals released by cleaning agents, burning fuels, and other substances, and can irritate respiratory passages, cause nausea, and increase the likelihood of cancer. In some variations, the environment quality monitoring device may include one or more sensors using metal-oxide-silicon (MOS) technology to measure VOCs. As another example, formaldehyde ($CH_2O$), which is used in building materials and many household products, can cause tissue irritation and may increase the likelihood of cancer. In some variations, the environment quality monitoring device may include one or more sensors using electrochemical methodology to measure $CH_2O$. As yet another example, carbon monoxide (CO) is an odorless, colorless gas that, when breathed by humans and other hemoglobic animals, displaces oxygen in the blood and leads to oxygen deprivation in vital organs and possibly death. In some variations, the environment quality monitoring device may include one or more sensors using electrochemical technology to measure CO. Accordingly, in some variations the environment quality monitoring device can measure amount of one or more of such gases. In an exemplary variation, the environment quality monitoring device includes sensors configured to measure amount of all three of $CO_2$, total VOCs, and $CH_2O$. For example, the environment quality monitoring device can include a $CO_2$ sensor having an effective measurement range of between about 0 ppm and about 3000 ppm and a resolution of about 1 ppm, a total VOC sensor having an effective measurement range of between about 1 ppm and about 30 ppm of ethanol, and a sensitivity of between about 0.15 Rs and about 0.5 Rs (sensor resistance) at (10 ppm of ethanol)/Rs (environment). Additionally or alternatively, in some variations the environment quality monitoring device may include one or more sensors configured to measure one or more nitric oxides ($NO_x$), one or more sulfur oxides ($SO_x$), hydrogen sulfide ($H_2S$), and/or other suitable gases.

Furthermore, the environment quality monitoring device may additionally or alternatively include at least one sensor configured to measure temperature, humidity, and/or other environmental conditions. Aside from discomfort, elevated temperature can, for example result in mental fatigue, which may cause diminished reaction times and delayed information processing. High levels of humidity can result in mold growth on surfaces, which may trigger various health conditions such as asthma, respiratory distress, and/or irritation of the eyes, nose, and mouth. Furthermore, exposure to hazardous conditions resulting from building decay, water damage, poor plumbing, and older pollutants can be exacerbated by high levels of humidity. Accordingly, in some variations the environment quality monitoring device can measure temperature and/or humidity of ambient environment. The environment quality monitoring device may, for example, include one or more sensors using MOS technology for measuring temperature and/or humidity. In an exemplary variation, the environment quality monitoring device includes at least one temperature sensor having a range of between about 0° C. and about 99° C. (or between about 15° C. and about 85° C.) and a resolution of about 0.1° C., and a humidity sensor having a range of between about 0% and 99% (or between about 10% and about 90%) relative humidity (RH) and a resolution of about 0.1% RH.

In some variations, the environment quality monitoring device may additionally or alternatively include at least one sensor configured to measure barometric pressure. Differences in barometric pressure (e.g., between different regions of a room, between an interior and an exterior of a room, etc.) can affect the flow of infectious particles. For example, a positively pressured room can protect occupants and/or materials in the room by tending to exclude infectious particles, while a negatively pressured room tends to contain infectious particles within a room. The magnitude of the pressure difference is correlated to the strength of the tendency to exclude or contain particles. Accordingly, in some variations the environment quality monitoring device can measure barometric pressure, such that multiple environment quality monitoring devices can provide an indication of regional pressure differences. The environment quality monitoring device may, for example, include one or more sensors using MOS technology for measuring barometric pressure. In an exemplary variation, an environment quality monitoring device can include a barometer (pressure sensor) having a range of between about 300 hPa and about 1100 hPa, and a resolution of about 0.12 Pa.

In some variations, the environment quality monitoring device may additionally or alternatively include at least one sensor configured to measure sound intensity. Exposure to noisy environments may result in partial or complete hearing loss. Accordingly, in some variations the environment quality monitoring device may include one or more microphones configured to measure noise in the environment, or Sound Pressure Level (SPL). An exemplary microphone is a MEMS microphone including a piezoelectric sensor and circuitry to buffer and amplify sensor output. Furthermore, in order to distinguish ambient noises from noises generated by the environmental monitoring device (e.g., built-in cooling fan, thermal noise, etc.), signal processing on the signals from the one or more microphones may be performed. For example, signals from the one or more microphones may be filtered (e.g., high pass filter, low pass filter, bandpass filter, etc.). Additionally or alternatively, in some variations at least some noises generated by the environmental monitoring device (e.g., fan, pump, etc.) may be reduced by temporarily turning off the noise-generating component(s) (e.g., pausing operation of the fan or pump) when sound intensity is being measured. In some variations, the noise-generating component(s) may be turned off a predetermined period of time before the sound intensity is being measured, so as to allow a settling period for activity and associated noise to cease (e.g., at least 1 second, at least 2 seconds, at least 3 seconds, at least 5 seconds, etc.). Furthermore, beamforming methods can be used to detect direction of sound.

In some variations, the environment quality monitoring device may additionally or alternatively include at least one sensor configured to measure ambient light intensity. Light intensity in a room may physiologically affect a person, leading to discomfort (e.g., fatigue, headaches) or other challenges (e.g., difficulty in focusing). Accordingly, in some variations the environment quality monitoring device may include one or more sensors configured to measure light intensity, such as a photocell (photoresistor), photodiode, or other suitable light sensor. Such one or more light sensors may be configured to determine the presence and/or intensity of light in ambient environment. In some variations, measured ambient light conditions may provide a basis for adjusting the light intensity of a visual alert associated with the environment monitoring device (as described above).

In some variations, a kit including at least one environment quality monitoring device may include one or more informational references describing the environment quality parameters measured by the environment quality monitoring device. In some variations, the information references may be configured to be displayed in a publicly-accessible space (e.g., wall, refrigerator, etc.). For example, the kit may include magnets, stickers, adhesive clings, flyers or brochures, and/or other informational items describing environment quality parameters. Such items may, for example, define environment quality parameters, describe health risks associated with the environment quality parameters, describe ways to improve environment quality, and/or otherwise mitigate health risks.

Other Electronics

Generally, in addition to sensors described above, various electronics may be enclosed within the housing. For example, as shown in FIG. 1A, one or more controllers 120 including a processor (e.g., CPU) and/or one or more memory devices 130 (which can include one or more computer-readable storage mediums). The processor may incorporate data received from memory and user input. The memory may include stored instructions to cause the processor to execute modules, processes, and/or functions associated with the methods described herein. In some variations, the memory and processor may be implemented on a single chip, while in other variations they can be implemented on separate chips.

The processor may be any suitable processing device configured to run and/or execute a set of instructions or code, and may include one or more data processors, image processors, graphics processing units, physics processing units, digital signal processors, and/or central processing units. The processor may be, for example, a general purpose processor, a Field Programmable Gate Array (FPGA), an Application Specific Integrated Circuit (ASIC), and/or the like. The processor may be configured to run and/or execute application processes and/or other modules, processes and/ or functions associated with the system and/or a network associated therewith. The underlying device technologies may be provided in a variety of component types (e.g., MOSFET technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

In some variations, the memory may include a database and may be, for example, a random access memory (RAM), a memory buffer, a hard drive, an erasable programmable read-only memory (EPROM), an electrically erasable read-only memory (EEPROM), a read-only memory (ROM), Flash memory, and the like. The memory may store instructions to cause the processor to execute modules, processes, and/or functions such as measurement data processing, measurement device control, communication, and/or device settings. Furthermore, the memory may temporarily store measurement data in the form of a buffer (e.g., data for the previous five seconds, ten seconds, thirty seconds, etc.), such that measurement data is less likely to be lost in the event of a disruption or interruption of network connectivity during transmission of measurement data to a remote memory storage device. Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CDROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Furthermore, one or more network communication devices 140 may be configured to connect the environment quality monitoring device to another system (e.g., Internet, remote server, database) by wired or wireless connection. In some variations, the environment quality monitoring device may be in communication with other environment quality monitoring devices via one or more wired or wireless networks. In some variations, the communication device may include a radiofrequency receiver, transmitter, and/or optical (e.g., infrared) receiver and transmitter configured to communicate with one or more device and/or networks. In an exemplary variation, the network communication devices 140 may include a cellular modem (e.g., 3G/4G/5G cellular modem) such that it is advantageously not dependent on internet Wireless Fidelity (WiFi) access for connectivity. For example, in some variations the network communication devices 140 may include a cellular modem for built-in cellular connectivity (e.g., a SIM card may be included) and thus the environment quality monitoring device may be easily installed without the need for a local network infrastructure (e.g., WiFi). Furthermore, in some variations the environment quality monitoring device may include WiFi as a secondary network communication option (e.g., in the event of failure of cellular communication, such as due to a cellular tower failure or other outage).

Alternatively, wireless communication may use any of a plurality of communication standards, protocols, and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, WiFi, or any other suitable communication protocol. In some variations, the devices herein may directly communicate with each other without transmitting data through a network (e.g., through NFC, Bluetooth, WiFi, RFID, and the like). For example, devices (e.g., one or more computing devices and/or health improvement devices) may directly communicate with each other in a 1:1 relationship, or in a hub-spoke or broadcasting connection ("one to many" or 1:m relationship). As another example, the devices (e.g., one or more computing devices and/or one or more environment quality monitoring devices, etc.) may communicate with each other through mesh networking connections (e.g., "many to many", or m:m relationships), such as through Bluetooth mesh networking.

Figure 6:
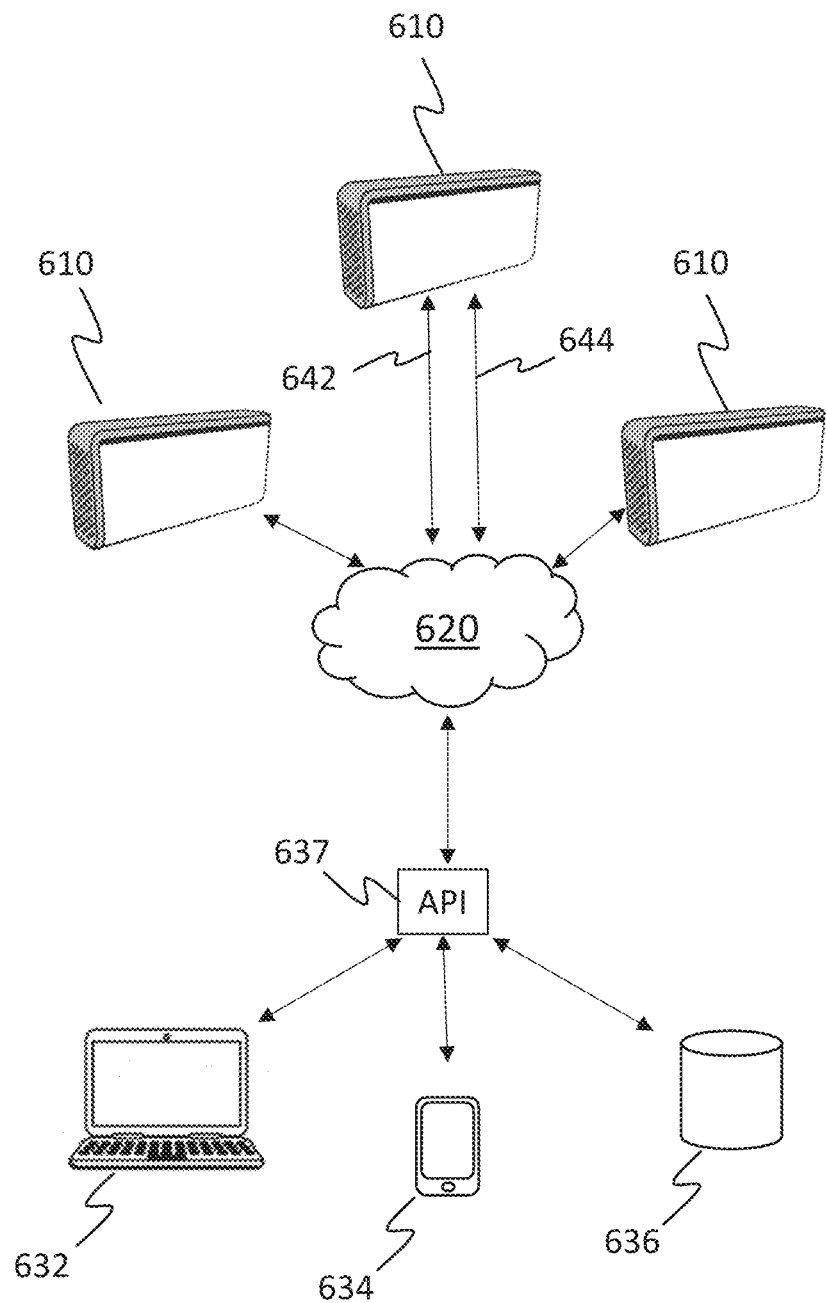
FIG. 6 is an illustrative schematic of an environment quality monitoring system including one or more environment quality monitoring devices in communication with a network.

The environment quality monitoring device may, in some variations, be configured to communicate with a database via multiple channels. For example, as shown in FIG. 6, an environment quality monitoring device may communicate with a server 620 via at least a first channel 642 and a second channel 644. The first channel 642 may, for example, be used for general communication (e.g., pinging to check device status) and/or governing security between the environment quality monitoring device and the server 620. In an exemplary variation, the first channel 642 may require dual-layer security involving confirmation on both the device-side and the server-side. The second channel 644 may, for example, be used to communicate data (e.g., sensor data). In an exemplary variation, data may be communicated over the second channel 644 using EDGE or another suitable mobile data standard or mobile communication methodology. One benefit of utilizing multiple channels in this manner is safeguarding against certain failures. For example, if there is an error or "bug" in the code relating to data communication in the second channel 644, the first channel 642 may still be functional to enable the environment quality monitoring device to communicate with the server 620.

In some variations, the environment quality monitoring device may include at least one global positioning system (GPS) receiver 142 for providing GPS data representative of the location of the environment quality monitoring device. The GPS receiver 142 may, for example, be included in the electronics subsystem housed within the housing of the environment quality monitoring device, similar to the sensors described above. The GPS receiver may be configured to receive positioning signals from GPS satellites through a GPS antenna, such that location of the GPS receiver can be determined based on trilateration. Location of the GPS receiver, which can be correlated to location of the environment quality monitoring device associated with the GPS receiver, may be communicated via the one or more network communication devices 140 to another system for processing (e.g., display on one or more GUIs, such as any of those described below).

Sensor Data Processing

As shown in FIG. 5A and described above, an environment quality monitoring device 500 may include a plurality of sensors configured to measure a plurality of environment quality parameters. Following this measurement, the sensor data including environment quality parameter values may be processed. Sensor data may be processed locally (e.g., by the sensor monitoring device) and/or remotely by one or more suitable processors.

For example, as described above, sensors may be sampled at any suitable frequency (e.g., between about 3 and about 6 times per minute), and any outliers that might be the result of a sensor anomaly or malfunction, and/or system interference, etc. may be eliminated to generate "corrected" sensor data. For example, a sensor sample value may be considered a high value outlier if it exceeds an immediately preceding or following sample value (and/or running average of the immediately preceding or subsequent or surrounding n sample values (e.g., n=2, 3, 4, or 5)) by a predetermined threshold amount. Similarly, a sensor sample value may be considered a low value outlier if it is less than an immediately preceding or following sample value (and/or running average of the immediately preceding or subsequent or surrounding n sample values (e.g., n=2, 3, 4, or 5)) by a predetermined threshold amount. Other suitable signal processing (e.g., noise reduction with filtering, etc.) may additionally and/or alternatively be performed on the sensor data.

After the sensor data is processed, the sample values in the "corrected" sensor data may be timestamped. If processed locally, then the timestamped sensor data may then be communicated to a server (e.g., via cloud network 180 as shown in FIG. 1C and described above). In some variations, the sensor data may be communicated to a server periodically at any suitable frequency (e.g., once per minute, or more than about once per minute)

In some variations, all sample values in the raw or corrected sensor data may be provided and used for further analysis (e.g., calculating an environment quality score, as described below). Alternatively, at least some sample values with a certain monitoring time period (e.g., every minute, every 30 seconds) may be combined, averaged (e.g., mean or median), or otherwise collapsed into a representative sample value for that monitoring time unit, and the representative sample value may be used for further analysis. For example, in some variations, every minute the environment quality monitoring device may gather all corrected sample data and determine a representative sample value for each environment quality parameter. This generation of a representative sample value for a monitoring time unit may be performed by a local processor(s) in the environment quality monitoring device prior to its communication to a server, and/or by one or more remote processor(s) after communication to a server.

Environment Quality Score

Figure 5B:
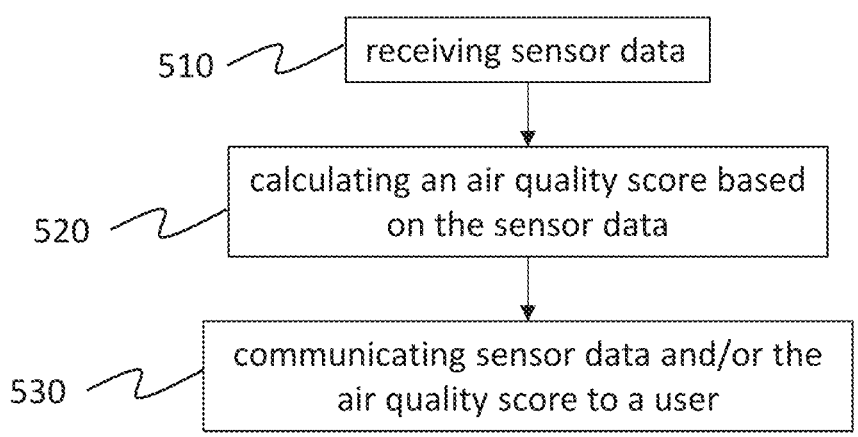
FIG. 5B is a flowchart of an exemplary variation of a method of operation of an environment quality monitoring device.

For example, as shown in FIG. 5B, one method of processing sensor data includes receiving sensor data 510, calculating an environment quality score based on at least a portion of the sensor data 520, and communicating at least one of sensor data and the environment quality score to a user 530. The environment quality score may, for example, be generated by one or more processors within the environment quality monitoring device, or by one or more remote processors receiving sensor data over a network (e.g., wireless network). The environment quality score may take in consideration various health and safety standards (e.g., from OSHA, ASHRAE, EPA, etc.) and/or other information other empirical sources (e.g., industrial hygienists), etc.

In some variations, the environment quality score may be an air quality score primarily focused on air quality. For example, in some variations, the air quality score may be based on weighted values of a plurality of environment quality parameters relating to air quality, with each environment quality parameter weighted with a respective weighting factor. A weighting factor for a particular parameter may be at least partially based on, for example, that parameter's impact on overall air or environment quality. For example, in some variations, weighting factors for gases (e.g., $CO_2$, VOCs, CO, $CH_2O$, etc.) and/or particulate matter in ambient air may generally be greater than others (e.g., temperature). The weighting factors may be the same for all or some environment quality parameters, or each environment quality parameter may have a unique weighting factor. The set of weighting factors for calculation of an air quality score may be adjustable depending on various circumstances.

Multiple environment quality parameters may be combined into an air quality score by summing a measure of the severity of each environment quality parameter, multiplied by its respective weighting factor. For example, an air quality score (AQI) may generally combine multiple environment quality parameters $P_1$-$P_N$ in accordance with Equation 1 below:

$$AQI = \left(\frac{P_1}{P_{1,max}}\right)(WF_1) + \left(\frac{P_2}{P_{2,max}}\right)(WF_2) + \ldots + \left(\frac{P_N}{P_{N,max}}\right)(WF_N) \quad (1)$$

where $P_N$ is the current environment quality parameter value, $P_{N,\,max}$ is the maximum possible value for the environment quality parameter, and $WF_N$ is the weighting factor for the environment quality parameter. An exemplary set of weighting factors includes the weighting factors shown in Table 1 below.

TABLE 1

Example weighting factors for determination of air quality score

| Environment Quality Parameter | Weighting Factor |
|---|---|
| Carbon dioxide ($CO_2$) | 25 |
| Particulate matter (PM1, PM2.5, PM10) | 25 |
| VOCs | 17 |
| Formaldehyde ($CH_2O$) | 15 |
| Humidity | 13 |
| Temperature | 5 |

Although specific weighting factors are shown in Table 1, it should be understood that these values are merely exemplary and other weighting factors may be suitable in other variations. Furthermore, in some variations, the set of weighting factors for calculating air quality score may be adjustable based on profile settings of the environment quality monitoring device, such as type of location or setting of the environment quality monitoring device. Certain environment quality parameters may be more or less important for different environments. For example, because sick individuals may be more vulnerable and susceptible to respiratory irritation than healthy individuals, the parameter(s) of particulate matter levels may be associated with a larger weighting factor when the sensor data measured by a device placed in a healthcare setting (e.g., patient room in a hospital or clinic) than when the sensor data measured by a device placed in an office setting.

As another example, the set of weighting factors for calculating air quality score may vary on user profile information, as different kinds of individuals may have greater sensitivity to certain environment quality parameters. For example, an individual with known reduced lung function may be more sensitive to the effects of elevated levels of carbon dioxide in ambient air, compared to a healthy individual. Accordingly, carbon dioxide level may be associated with a larger weighting factor when the sensor data is measured by a device placed in the bedroom of the individual with reduced lung function, than when the sensor data is measured by a device placed in the bedroom of a healthy individual.

The air quality score may be normalized to any suitable range of numerical values, such as between 0 and 100, between 0 and 10, between 1 and 5, etc. An air quality score may be rounded to the nearest integer, or to any suitable precision level. A numerical value may be represented in other forms, such as number of dots, number of stars, etc.

In some variations, the air quality score may be transformed into a qualitative description of ambient air quality. For example, the air quality score may be transformed into any of one or more descriptive categories by comparing the air quality score to one or more quantitative value ranges. For example, in a variation in which air quality may be categorized as any of three categories, the air quality score may be compared to the bounding thresholds (e.g., upper and lower thresholds) of a first value range corresponding to a first air quality category, the bounding thresholds of a second value range corresponding to a second air quality category, and/or the bounding thresholds of a third value range corresponding to a third air quality category. For example, in some variations, for an air quality score scaled to a 0-100 range, an air quality score between 90 and 100 may correspond to "good" air quality, an air quality score between 80 and 89 may correspond to "moderate" air quality, and an air quality score below 80 may correspond to "poor" air quality. In some variations, such value ranges may be of generally equal size or span. Alternatively, some value ranges may be wider or narrower than others (e.g., a "poor" air quality may mean an air quality score between 0-50, a "moderate" air quality may mean an air quality score between 51 and 80, and a "good" air quality may mean an air quality score between 81 and 100).

Furthermore, in some variations the environmental quality score may holistically characterize multiple aspects of the environment in addition to air quality. For example, the environmental quality score (EQI) may combine air quality score (AQI) described above with sound intensity levels as shown in Equation 2:

$$EQI = \left(\frac{AQI}{AQI_{max}}\right)(WF_{AQI}) + \left(\frac{SL}{SL_{max}}\right)(WF_{SL}) \quad (2)$$

where AQI=current air quality score, $AQI_{max}$ is the maximum value of the air quality score (e.g., 100), $WF_{AQI}$ is a weighting factor for the air quality score, SL=sound level (e.g., in dB), $SL_{max}$ is maximum measurable sound level for the sound sensor in the environmental monitoring device (e.g., between about 120 dB and about 160 dB), and $WF_{SL}$ is a weighting factor for the sound level. In an exemplary variation, the air quality score has a weighting factor of 75 and the sound level has a weighting factor of 25. Furthermore, in some variations, the environmental quality score may additionally or alternatively incorporate light intensity levels in a similar manner as sound intensity levels as shown in Equation 2 (e.g., including a term associating the severity of the light intensity level weighted by a respective weighting factor).

However, it should be understood that these values are merely exemplary and other weighting factors for calculating environmental quality score may be adjustable (e.g., as described above calculating air quality score). Furthermore, the variation of environmental quality score combining air quality score, sound intensity levels, and/or light intensity levels may be normalized and/or transformed into a qualitative description of ambient environment quality in a similar manner as that described above for the air quality score.

Similarly, any of the individual environment quality parameters may be transformed into an environment quality parameter score characterizing severity of risk associated with individual or grouped environment quality parameters. For example, while an air quality score may be generated as described above to holistically describe air quality based on multiple different kinds of parameters, an environment quality parameter score may be based on a single parameter or multiple closely related parameters. For example, a measured humidity level may be transformed into a numerical score scale or categorized into a descriptive category (e.g., "low", "medium", "high"). As an example of generating an environment quality parameter score based on multiple closely related parameters, all measured amounts of particulate matter (e.g., PM10, PM2.5, PM1) can be combined and collectively transformed into a numerical score scale or descriptive category.

The environment quality score and/or sensor data (or corresponding air quality parameter scores) may be communicated to a user such as in the form of an alert. For example, the air quality score may be communicated to a user on the air quality monitoring device itself, such as a light waveguide described above with respect to FIGS. 2A and 2B or FIGS. 19E and 19F. For example, the air quality score may be communicated by illuminating the waveguide to a particular color that corresponds to the air quality score (numerical value or its equivalent descriptive category). In the exemplary variation of FIGS. 2A and 2B, the lighted indicator 230 may be illuminated in any of multiple colors to indicate air quality (e.g., red for "poor" environment quality, yellow or orange for "moderate" environment quality, and blue for "good" air quality). A visual alert may additionally or alternatively include temporally varying illumination patterns, such as blinking or flashing of the waveguide.

Additionally or alternatively, as described in further detail below, the air quality score and/or sensor data (or corresponding air quality parameter scores) may be communicated through one or more user interfaces on a computing device, and may be communicated as a numerical value or its equivalent descriptive category. Descriptive categories may be text-based (e.g., "poor", "moderate" or "fair", "good", "excellent", etc.). Other descriptive categories may include a graphical indication of ambient air quality, such as emoticons (e.g., sad face, neutral face, happy face) or other representative icons.

Event Identification/Classification

Figure 5C:
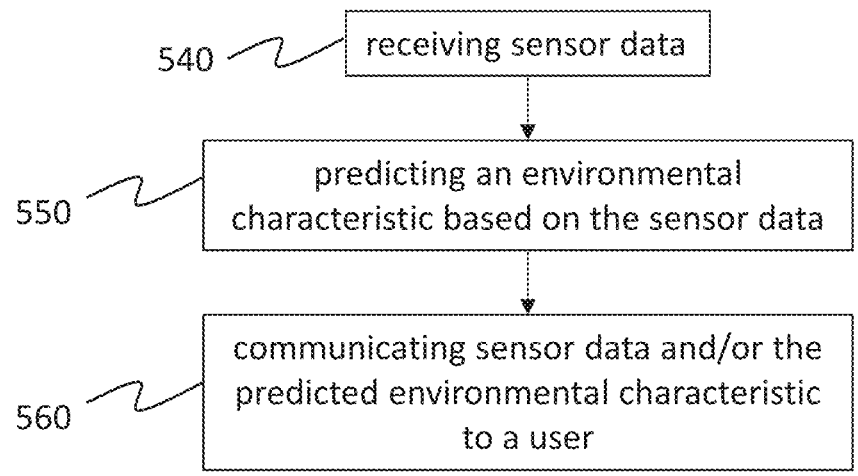
FIG. 5C is a flowchart of an exemplary variation of a method of operation of an environment quality monitoring device.

As shown in FIG. 5C, another exemplary method of processing sensor data includes receiving sensor data 540, predicting an environmental characteristic based on the sensor data 550, and communicating sensor data and/or the predicted environmental characteristic to a user 560. In this example, one or more various features of an environment can be predicted based on a pattern of sensor data from an environment quality monitoring device located in the environment. A predicted environmental characteristic may include, for example, an event and/or a condition of the environment near an environment quality monitoring device providing sensor data for the prediction.

In some variations, the environmental characteristic may be predicted by analyzing the overall pattern, or "signature" of multiple environment quality parameter values with artificial intelligence and/or machine learning techniques. For example, a machine learning model may be trained using sensor data obtained under known environmental conditions, such that the model may output a determination of a known environmental condition based on an input of similar sensor data. In some examples, feature vectors may be extracted from the training sensor data and fed into a suitable machine learning algorithm. Various machine learning algorithms may be implemented, such as neural network algorithms, classification algorithms, regression algorithms, etc.

Accordingly, various environment quality parameters may be analyzed (e.g., with a trained model as described above) to predict a variety of environmental characteristics, as a respective signature or pattern of environment quality parameters may be identified (e.g., based on a training data set) and associated with a respective environmental characteristic. In other words, a combination of artificial intelligence and/or machine learning can be used to automatically detect states or events based on the sensor data from an environment quality monitoring device such as that described herein and/or other known information (e.g., time of day as reflected in timestamp of sensor data, contemporaneous HVAC cycles, etc.).

For example, sensor data such as $CO_2$, PM, and/or VOCs may be analyzed to predict whether certain activities are being performed in the environment (e.g., smoking, drug-taking, cooking, firearm use, etc.). For example, smoking may be predicted if levels of PM increase by a threshold amount (e.g., at least 30 mg/m$^3$) abruptly relative to a baseline, and the decay to the baseline lasts more than a predetermined period of time (e.g., 15 minutes). Additionally or alternatively, sensor data may be analyzed to detect HVAC equipment activity, issues or failures. In yet other examples, sensor data (e.g., humidity and/or other data) may be analyzed to predict the existence of certain hazardous conditions in the environment (e.g., fire, mold, etc.).

Furthermore, in some examples, a number of persons in a room may be predicted based at least in part on $CO_2$, temperature, and/or other suitable sensor data. There are various applications of this information, such as identifying the location of the persons in a building outfitted with one or more environment quality monitoring devices (e.g., children and staff in a school during a lockdown event or other emergency, for rescue purposes).

Figure 16:
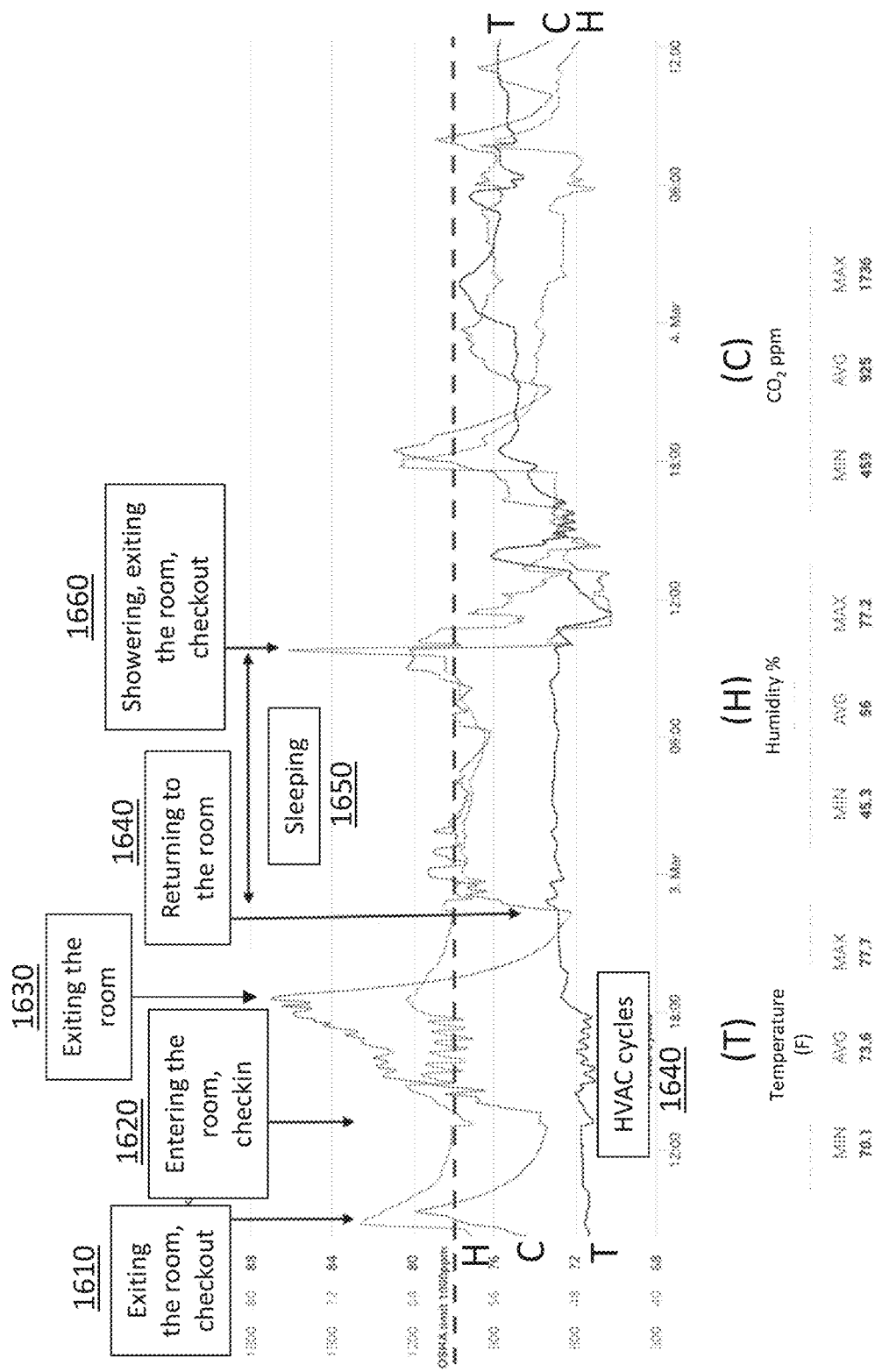
FIG. 16 is a plot including exemplary data illustrating exemplary methods of event detection based on information from an environment quality monitoring device.

An illustrative example of environmental predictions based on sensor data is shown in the plot of FIG. 16. FIG. 16 depicts sensor data of multiple environment quality parameters over time, as measured by an environment quality monitoring device placed in a hotel room. Specifically, FIG. 16 depicts trends of temperature ("T"), humidity ("H"), and carbon dioxide ("C") over time. Based at least in part on this sensor data and/or other predictive factors, multiple discrete events may be predicted.

For example, an event of a person entering the hotel room (1620, 1640) may be predicted based on an abrupt increase in $CO_2$ levels. Furthermore, variations of this event may be distinguished based on additional information. As an illustration, an event of a person entering and checking into the hotel room (1620) may be distinguished from an event of an existing room occupant returning to the hotel room (1640) based on time of day. For example, a person may be predicted as checking into the room if the increase in $CO_2$ levels occurs during a typical check=in period (e.g., between 1 pm and 5 pm). Furthermore, an event of cleaning staff entering the hotel room (not shown) may be distinguished from events of other people entering the room, based on additional information in combination with increased $CO_2$ levels, such as increased VOCs (e.g., from cleaning supplies) and/or increased temperature (e.g., from multiple cleaning staff being active in the room).

As another example, an event of a room occupant exiting the hotel room (1610, 1630, 1660) may be predicted based on an abrupt decrease in $CO_2$ levels. Furthermore, variations of this event may be distinguished based on additional information. As an illustration, an event of a room occupant checking out of the hotel room (1610, 1660) may be distinguished from an event of a room occupant temporarily exiting the room (1630) based on time of day and/or humidity levels. For example, a room occupant may be predicted as checking out of the hotel room if the decrease in $CO_2$ levels occurs during a typical check-out period in the morning (e.g., between 7 am and 12 pm, or other suitable window of time) and/or is preceded by an increased temperature and/or increased room humidity level which may be associated with the room occupant taking a shower prior to leaving.

Other activities by a person in the hotel room may also be predicted. For example, an event of a sleeping room occupant may be predicted based on substantially constant levels of humidity and $CO_2$, after a person has been predicted to enter the hotel room (but not yet exit the hotel room), which may be associated with a person present but being relatively inactive. Other factors, such as HVAC activity, may be identified (e.g., based on controlled temperature, humidity, etc.) and may further inform whether a person is sleeping, exercising, etc.

Although specific examples of environmental characteristics are discussed above, it should be understood that it is possible to train a machine learning model using any suitable training data for any suitable environmental characteristic. Accordingly, it is possible to predict other suitable environmental characteristics by identifying respective (and distinctive) environment quality parameter signatures associated with such other environmental characteristics.

Environment Remedial Activity

In some variations, measurements obtained from one or more environment quality monitoring devices may be analyzed as described herein to predict or otherwise assess characteristics or events relating to the environment. Based on such evaluation, one or more devices (e.g., devices in communication with a cloud network or other suitable network or server, such as with the environment quality monitoring device(s) as shown in FIG. 1C) may be operated to remedy or otherwise alter one or more characteristics of the ambient environment. The cloud network may function as a central intelligence system that may incorporate AI and/or ML to provide continuous environment monitoring (e.g., indoors and/or outdoors) and/or provide the ability to continuously assess the situation and adapt accordingly to control other remedial or environment-modulating devices such as air purifiers, humidifiers, HVAC, etc. In other words, the environment quality monitoring system may further function as an environment management system (e.g., cloud-based building or neighborhood management system). In some variations, the environment quality monitoring system may interface with (e.g., connect or co-exist) with existing building management systems such as BACnet.

Figure 5D:
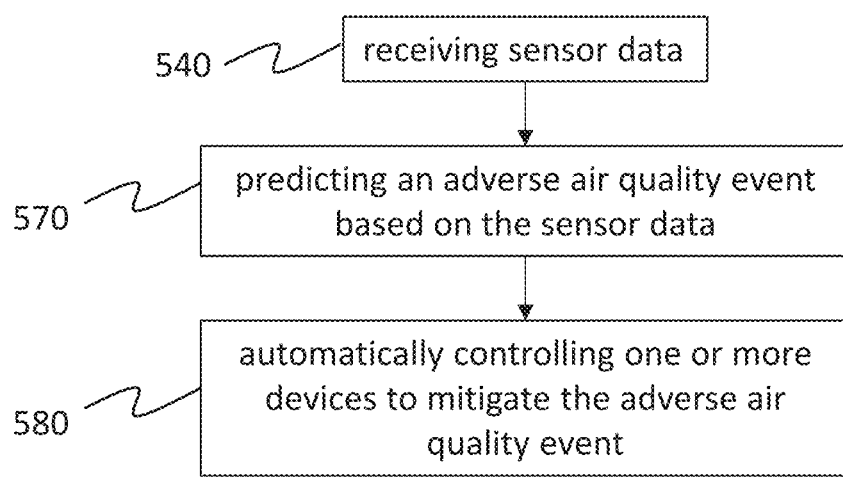
FIG. 5D is a flowchart of an exemplary variation of a method of operation of an environment quality monitoring device.

Accordingly, in some variations, as shown in FIG. 5D, a method for managing environmental quality (e.g., air quality) may include receiving sensor data 540 comprising a plurality of air quality parameters for an environment, wherein the sensor data is generated by one or more environment quality monitoring devices located in the environment, predicting an adverse air quality event based on the sensor data 570; and automatically controlling one or more devices to mitigate the adverse air quality event 580.

For example, in some variations the environment management system may be used to manage environmental conditions indoors and/or outdoors simultaneously for conditions conducive to transmission of infectious disease such as COVID-19 (or other diseases communicable through air or droplets, such as influenza). For example, the environment quality monitoring system may be used to monitor particulate levels (e.g., indoors). High particulate levels may be correlated to high probability of virus propagation due to viral particles traveling on dust particles, especially indoors. Upon detection of a predetermined threshold or severity of particle presence in the environment, appropriate remedial devices may be activated (e.g., one or more air purifiers connected to the environment management system may be engaged at a suitable speed or level to reduce particulate level in the environment). In some variations, in the absence of a detected severity of particle presence, the remedial devices may be turned off or operated at a lower speed, so as to increase the lifetime of the device (e.g., filters), reduce noise levels, save energy, etc.

As another example, the environment quality monitoring system may be used to monitor $CO_2$ levels. As described above, $CO_2$ levels may be used to indicate the density or concentration of people within a certain square footage, which may suggest the likelihood that exhaled air (which may include virus particles) is subsequently breathed in by another person. In some variations, upon detection of a predetermined threshold level of $CO_2$ in the environment, appropriate remedial devices may be activated to circulate fresh air, thereby diluting the $CO_2$. For example, the system may activate a connected HVAC or thermostat to initiate an air exchange process.

The characteristics of the air exchange process may be based on other parameters, such as outdoor conditions. For example, if an environment quality monitoring device is used outdoors and the particulate levels outdoors are measured as high, then the system may determine it is appropriate to not allow air exchange between outdoors and indoors, because doing so may instead increase the risk of virus propagation via outdoor particle transfer. However, in some variations the system may permit air exchange provided that any connected air purifier(s) are able to perform sufficient filtering to remove such outdoor particles. The ability of such filtering may be monitored by one or more other environmental quality monitoring devices measuring indoor particulate levels, for example. Additionally or alternatively, the air exchange rate and when it occurs may be based on measured $CO_2$ levels and a cost analysis function. In some variations, the system may determine when to activate air exchange based at least in part on outdoors temperature (e.g., measured by an outdoors environmental quality monitoring device) and $CO_2$ levels (e.g., measured by an indoors environmental quality monitoring device). When an air exchange happens, the HVAC system typically conditions the fresh outdoors air to a desired temperature, which can consume a significant amount of energy. Accordingly, a cost analysis function may be utilized to determine whether it is appropriate (and what rate) to execute such an air exchange.

Additionally or alternatively, in some variations the environment management system may be used to monitor and/or other environmental conditions such as temperature and humidity. For example, temperature and/or humidity may be controlled to maintain comfortable conditions for occupants (e.g., of an indoors space) while reducing lifetime of potential viral particles in the air. For example, the environment management system may be used to maintain a reduced humidity environment, which may reduce the lifetime of a virus. Furthermore, in some variations the environment management system may be used to manage the environment in response to toxic substances (e.g., VOCs), which may have an increased presence in the environment due to hand hygiene (e.g., use of hand sanitizer) and/or sanitization of surfaces in an indoors environment. Accordingly, in some variations, upon detection of a predetermined threshold level of VOCs in the environment, appropriate remedial devices may be activated to circulate fresh air (e.g., increasing air exchange flow rate, activating air purifiers, etc.), similar to that described above.

Additionally or alternatively, this metric of predicted density of people may be used to generate alerts that may help enforce social distancing or limitations of gatherings (e.g., certain permissible number of people in a room), so as to further reduce transmission of infectious disease.

As another example, the environment management system may be similarly used to automatically control one or more devices (e.g., HVAC, humidifier, dehumidifier, filter or purifier, etc.) in order to maintain other ideal or goal environmental conditions (e.g., in response to an air quality score and/or environmental quality score falling before a predetermined threshold, or any other suitable environment quality parameter failing meet a predetermined threshold or range).

User Interface

Figure 7:
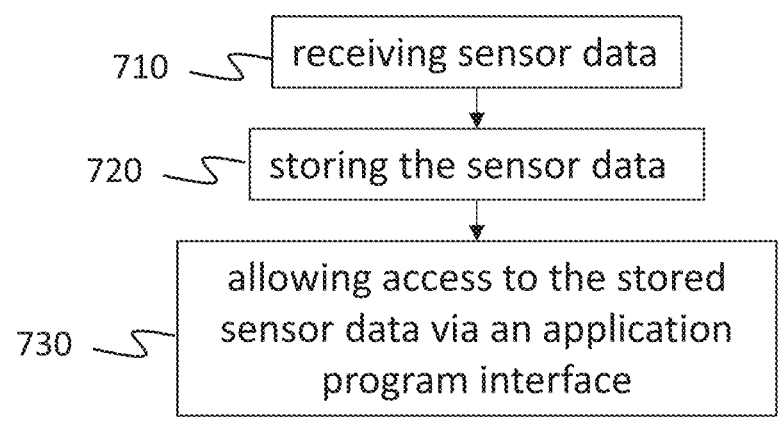
FIG. 7 is a flowchart of an exemplary variation of a method of operation of an environment quality monitoring system.

As shown in FIG. 6, one or more environment quality monitoring devices 610 may be configured to communicate with a cloud network or other suitable network or server 620, such as for communicating sensor data, sensor data results, and/or device information (e.g., sensor status, overall device status, serial number, etc.). One or more computing devices, such as desktop or laptop computers 632, or mobile computing devices (e.g., mobile cellular devices 634, tablet or other portable computing devices, etc.) may also be configured to communicate with the network 620. Additionally or alternatively, one or more storage devices 636 may be configured to communicate with the network 620. Furthermore, other third party devices (e.g. environmental management systems, virtual assistant devices such as Amazon Echo® or Google Home™ devices, etc.) may communicate with the network 620. Additionally, similar to that described above with respect to FIG. 1C, one or more remedial devices (e.g., air purifiers, humidifiers, HVAC, etc.) may be configured to communicate with the network 620. Accordingly, generally, the network 620 may provide a platform for such devices to access sensor data for analytics, such as via an application program interface 637 (API). For example, as shown in FIG. 7, a networking platform of environment quality monitoring system may be configured to receive sensor data 710, store the sensor data 720, and allow access to the stored sensor data via an API 730. The API may enable software application developers to consistently access and manipulate sensor data, sensor data analysis results, and/or manage environment quality monitoring device via other applications.

FIGS. 8-15 and 22-27 depict variations of graphical user interfaces (GUI) as examples of such applications. Users (e.g., owner-users, or users with a registered account with the system) may operate a user interface for viewing and/or manipulating sensor data or analysis results thereof, and/or for controlling the environment quality monitoring devices. For example, the environment quality monitoring devices 610 may be configured to communicate sensor data and/or results of sensor data analysis (as performed by processors on the devices, for example) over the network. Furthermore, user interfaces accessible on the computing devices in communication with the network may be configured to display the sensor data and/or analysis results to a user. Such user interfaces may further enable a user to control environment quality monitoring devices 610, such to enable or disable the devices 610, monitor power levels, etc. Graphical user interfaces can be displayed in a web portal application or mobile application on a remote computing device (e.g., desktop or laptop computer, mobile computing device, etc.).

Figure 8:
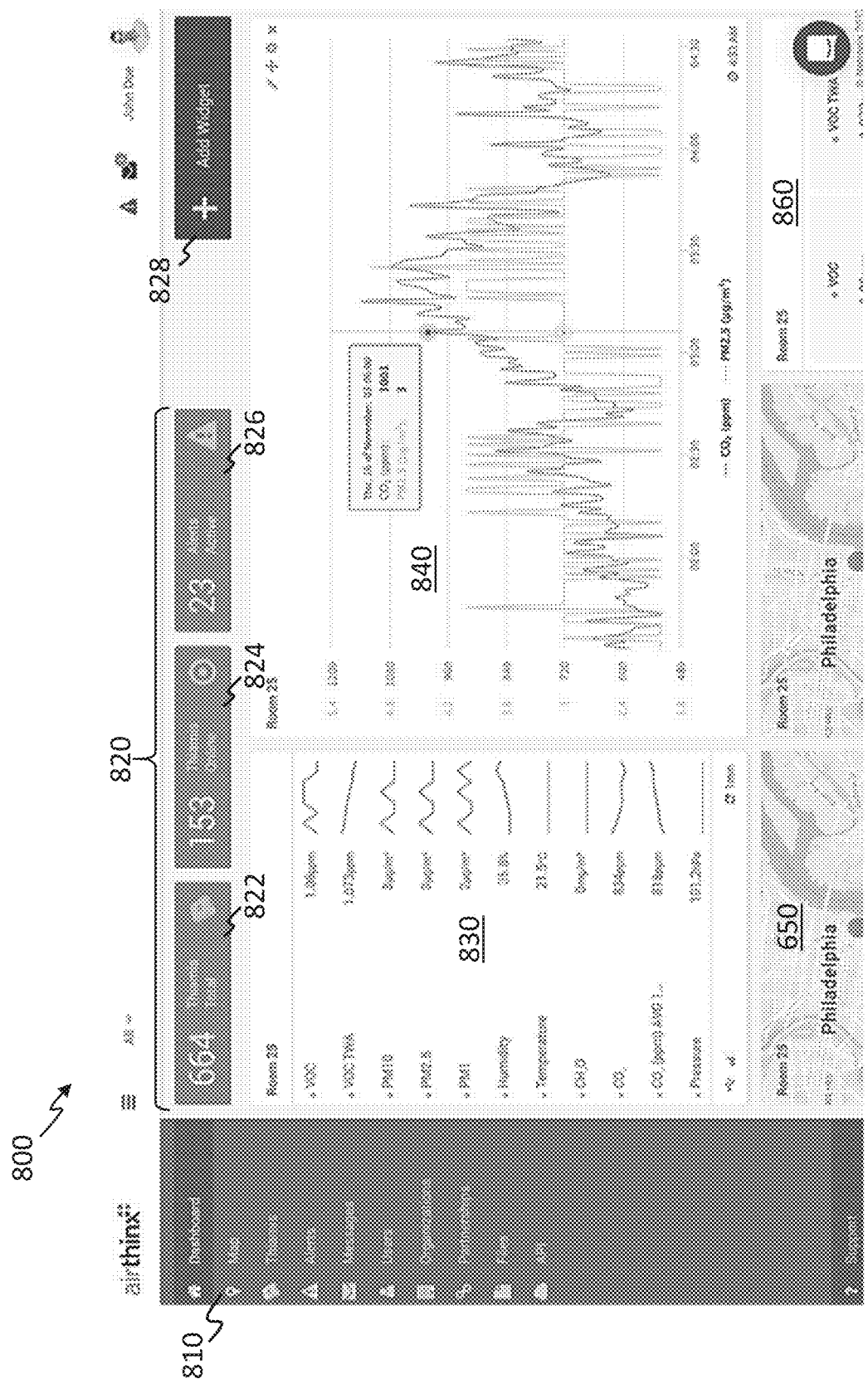
FIG. 8 is an exemplary variation of a web portal-based graphical user interface for use in the environment quality monitoring system.

FIG. 8 is an exemplary GUI 800 of a web portal application for use in conjunction with an environment quality monitoring system. Generally, GUI 800 displays a "dashboard" overview of the environment quality monitoring system, including one or more modular widgets displaying selected information. For example, a system overview bar 820 displays high-level system information. Such high-level system information can include an indicator 822 displaying total number of environment quality monitoring devices in the system, including active (e.g., "online" or powered) devices and inactive (e.g., "offline" or unpowered) devices. An indicator 824 can display number of active environment quality monitoring devices (e.g., devices currently providing continuous streams of sensor data). Furthermore, an alerts summary 826 can display a total number of alerts (or other suitable summary info) that have been triggered by environment quality monitoring devices in the system. Such alerts can be defined and set up by a user, as further described below. GUI 800 also may include a navigation menu 810 include links to other GUIs.

Additionally, GUI 800 may allow various modular widgets to be selected and arranged on the dashboard. Any suitable number of widgets (including multiple widgets of a particular type of widget) may be displayed. For example, a "add widget" button 828 can be selected, and GUI 800 can display a menu of selectable widgets to be placed on the dashboard. One example of a widget is a node widget 830, which provides a list summary of current sensor data from a selected environment monitoring device (node) in the system. The summary can include current values of environment quality parameters and/or a summary trend line of historical values of environment quality parameters. Another example of a widget is a chart widget 840 which displays, in greater detail, trend lines of historical values of one or more environment quality parameters over time. The time window displayed in the chart widget 840 may be adjusted by a user (e.g., with cursor grab points on the chart axes) or may be predetermined (e.g., preceding 24 hours, preceding 3 days, etc.). Detailed parameter value information can be viewed by selecting a particular point in time (e.g., with a scrolling timebar), which may prompt a popup information box to display selected environment quality parameter information for that point in time. In some variations, the chart widget 840 may be linked to a node widget 830, in that the chart widget 840 may display historical values of environment quality parameters that are selected through the node widget 830. In some variations, for clarity and ease of viewing, up to a predetermined number of environment quality parameter trends may be selected for display on the chart widget 840 (e.g., up to three parameters). However, multiple chart widgets 840 may be linked to the node widget 830 for displaying additional environment quality parameter trends.

Another example of a widget for display in GUI 800 is a map widget 850, which may display the geographical location of one or more environment quality monitoring devices. Location may be indicated with a device marker such as a representative dot or other icon. Closely-grouped devices may be collectively indicated with a group device marker such as a dot with a number indicating the number of member devices in that group (e.g., if distinct device markers are impractical to display separately). A popup display with device information (e.g., device name or ID code, location description, etc.) and/or sensor data may be displayed upon selection of a device marker on the map. Yet another example of a widget is a "block" widget 860, which may be similar to a node widget except that the environment quality parameters may be arranged by subject matter in categories and displayed in an array (e.g., PM10, PM2.5, and PM1 arranged together).

Figure 9:
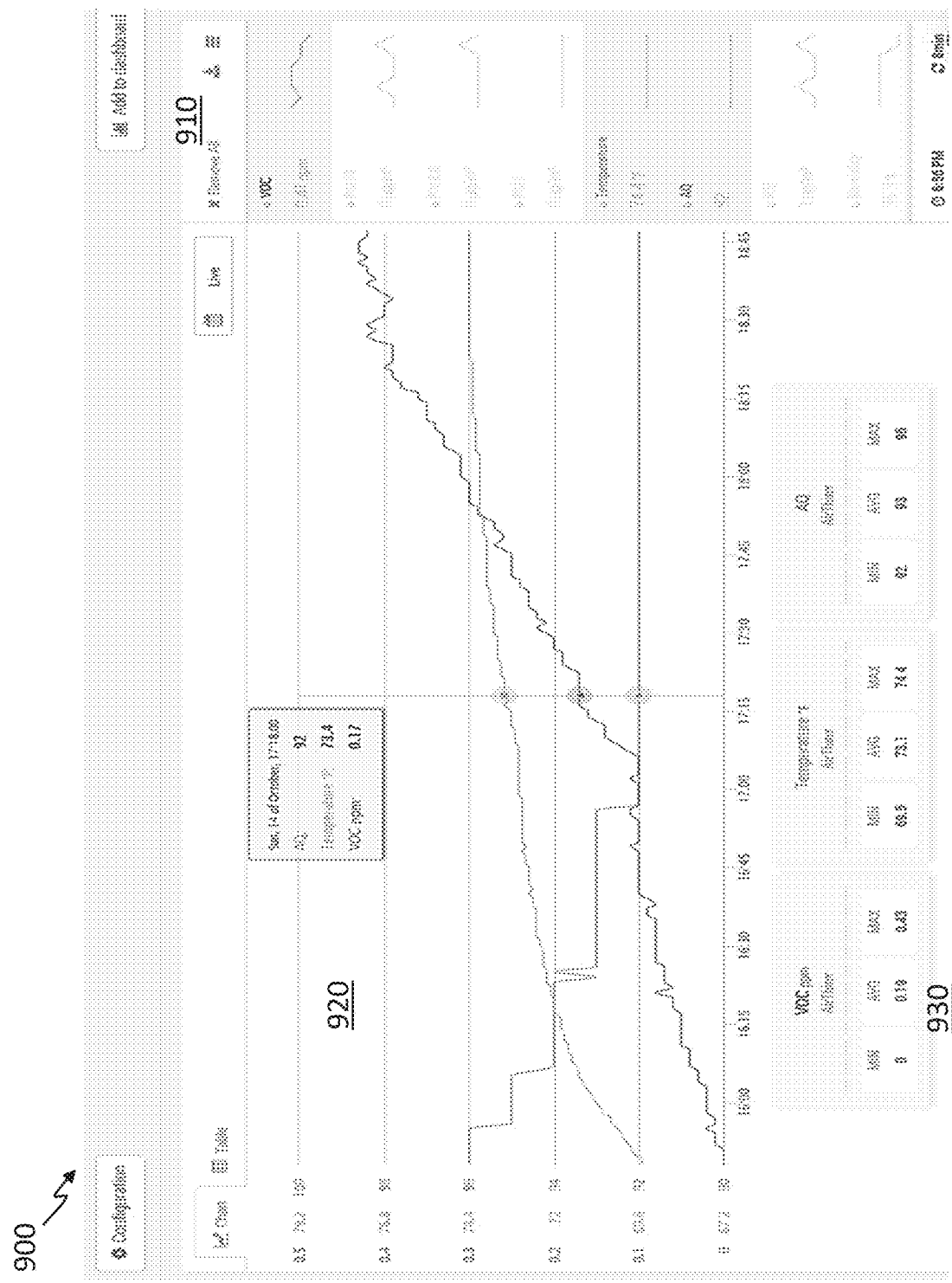
FIG. 9 is an exemplary variation of a web portal-based graphical user interface for use in the environment quality monitoring system.

FIG. 9 is an exemplary GUI 900 of a web portal application for use in conjunction with an environment quality monitoring system. Generally, GUI 900 may display a detailed chart 920 of one or more environment quality parameters measured by a selected environment quality monitoring device (similar to the chart widget 840 described above). Environment quality parameters may be selected from a list 910 of parameters (similar to the node widget 830 described above). Furthermore, a summary box 930 may provide summary information for the selected and displayed environment quality parameter values, including, for example, current value, minimum value, average value, and/or maximum value of each parameter as measured over the displayed time period. Accordingly, GUI 900 may be provide detailed current and/or historical data for one or more environment quality parameters.

Figure 10:
FIG. 10 is an exemplary variation of a web portal-based graphical user interface for use in the environment quality monitoring system.

FIG. 10 is an exemplary GUI 1000 of a web portal application for use in conjunction with an environment quality monitoring system. Generally, GUI 1000 may display a detailed map of geographical locations and/or status of one or more environment quality monitoring devices. Like the map widget 850, the GUI 1000 may indicate locations of devices with geographical markers, such as device markers 1010 and/or group device markers 1012. The location of a device may, for example, be derived based on signals received by a GPS receiver in the device as described above, and/or user entry of a device location (e.g., address). Upon selection of a particular device, a popup display with device information and/or sensor data may be displayed upon selection of a device marker on the map, similar to map widget 850. In GUI 1000, additional device information such as active status (e.g., whether powered, whether connected to the network, etc.) may be displayed according to a key 1030.

Figure 11:
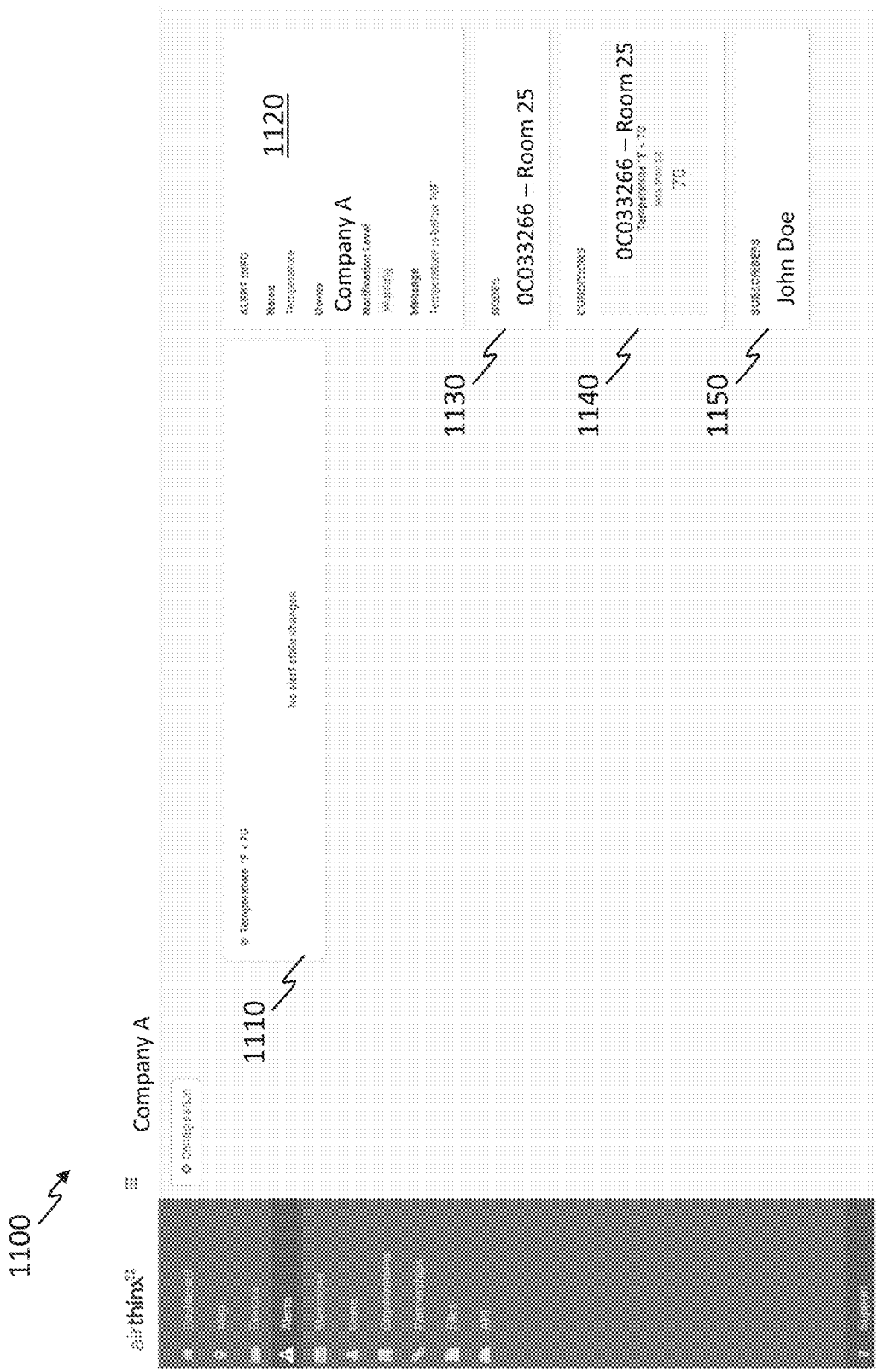
FIG. 11 is an exemplary variation of a web portal-based graphical user interface for use in the environment quality monitoring system.

FIG. 11 is an exemplary GUI 1100 of a web portal application for use in conjunction with an environment quality monitoring system. GUI 1100 allows a user to define and set up one or more alerts, to be triggered when an environment quality parameter value satisfies a defined threshold. In the example of FIG. 11, alert information box 1120 summarizes alert identification information, such as an alert name, a manager or owner controlling the alert, and the type of notification provided to one or more designated users when the alert is triggered. For example, a notification may be delivered in any one or more of multiple manners, such as SMS text, email, or notification popup in the user interface. A user may elect certain notification modes for different alert risk levels (e.g., only notification popup in the user interface for a low risk alert, an SMS text for a medium risk alert, or multiple modes for a high risk alert, etc.). Additionally, another information box 1130 may identify which nodes (which environment quality monitoring devices) to which the alert applies. Alert summary box 1140 may summarize the defined conditions of the alert that, if satisfied, will trigger the alert. For example, a user may define an upper threshold value, a lower threshold value, an upper or lower threshold rate of change in a value, an upper or lower threshold standard deviation or variance of a value over a predetermined period of time (e.g., day, week, month, etc.). As another example, a user may select (e.g., toggle on or off) one or more predefined alert conditions, such as governmental environment quality standards (e.g., U.S. Environmental Protection Agency (EPA) standards or other regional standards) relating to parameter limits and/or overall environment quality index scores. Some or all of these alert conditions (e.g., those expressed relative to upper and/or lower threshold values) may be displayed on the GUI (e.g., chart widget 840 as described above with respect to FIG. 8). Furthermore, subscriber information box 1150 may list users designated to receive alert notifications when the alert is triggered. Any of the above-described boxes may be selected to allow a user to edit the information and settings contained therein. Furthermore, it should be understood that the information in the various displayed boxes shown in GUI 1100 may, in other variations, be displayed in fewer or more boxes, or in any suitable manner.

Figure 12:
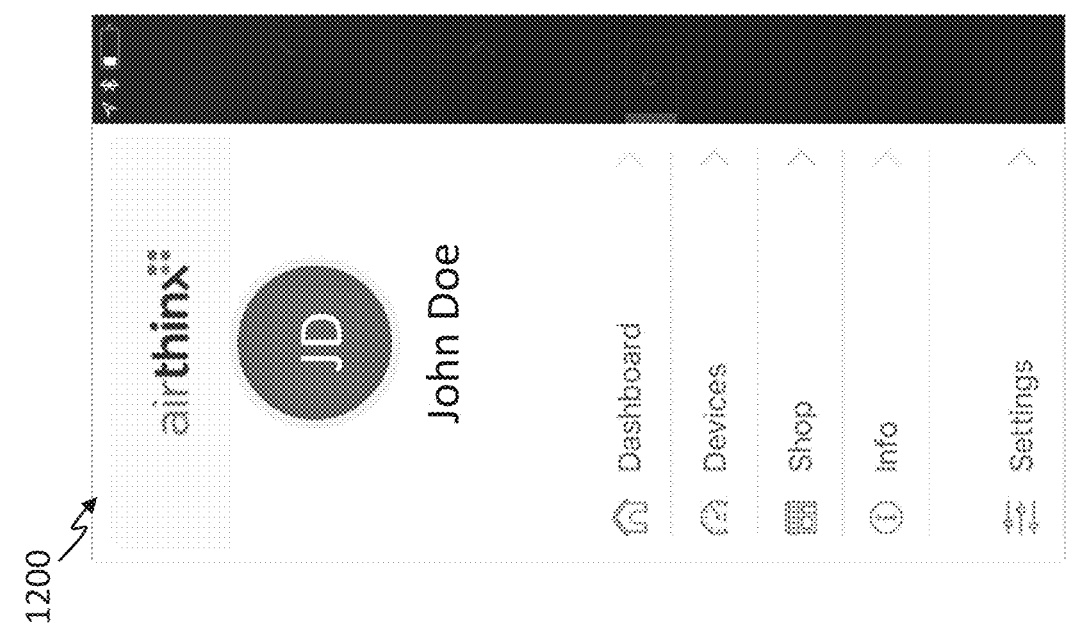
FIG. 12 is an exemplary variation of a mobile application-based graphical user interface for use in the environment quality monitoring system.

FIG. 12 is an exemplary GUI 1200 of a mobile application for use in conjunction with an environment quality monitoring system. GUI 1200 includes a navigation menu allowing access to other user interfaces. For example, the navigation menu may provide access to a dashboard (e.g., described below with respect to FIG. 13), a list of environment quality monitoring devices connected as part of the system (and selectable for display on the dashboard, for example), a link to an online storefront where additional devices and other components may be purchased, a link to information such as general environment quality educational information, and a link to settings.

Figure 13:
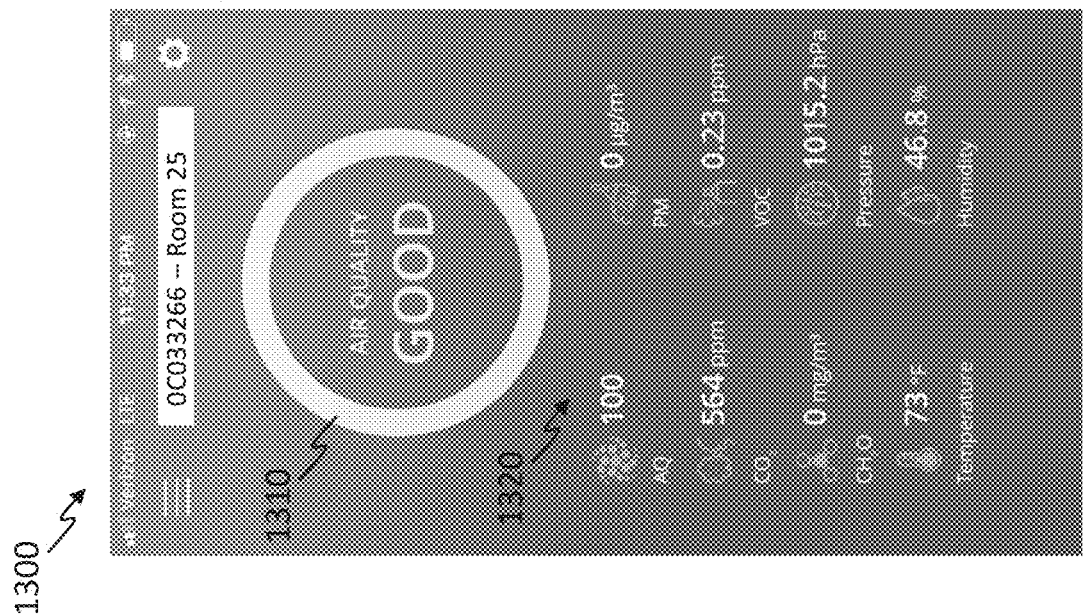
FIG. 13 is an exemplary variation of a mobile application-based graphical user interface for use in the environment quality monitoring system.

FIG. 13 is an exemplary GUI 1300 of a mobile application for use in conjunction with an environment quality monitoring system. Generally, GUI 1300 is a condensed dashboard providing environment quality information as measured by a selected environment quality monitoring device. For example, an environment quality score 1310 (value and/or qualitative description) may be displayed, as well as environment quality parameter values or scores 1320. The environment quality score 1310 and/or any of the environment quality parameter values 132 may be selectable by user to view additional detail about the selected item, such as historical trend info.

Figures 14, 15:
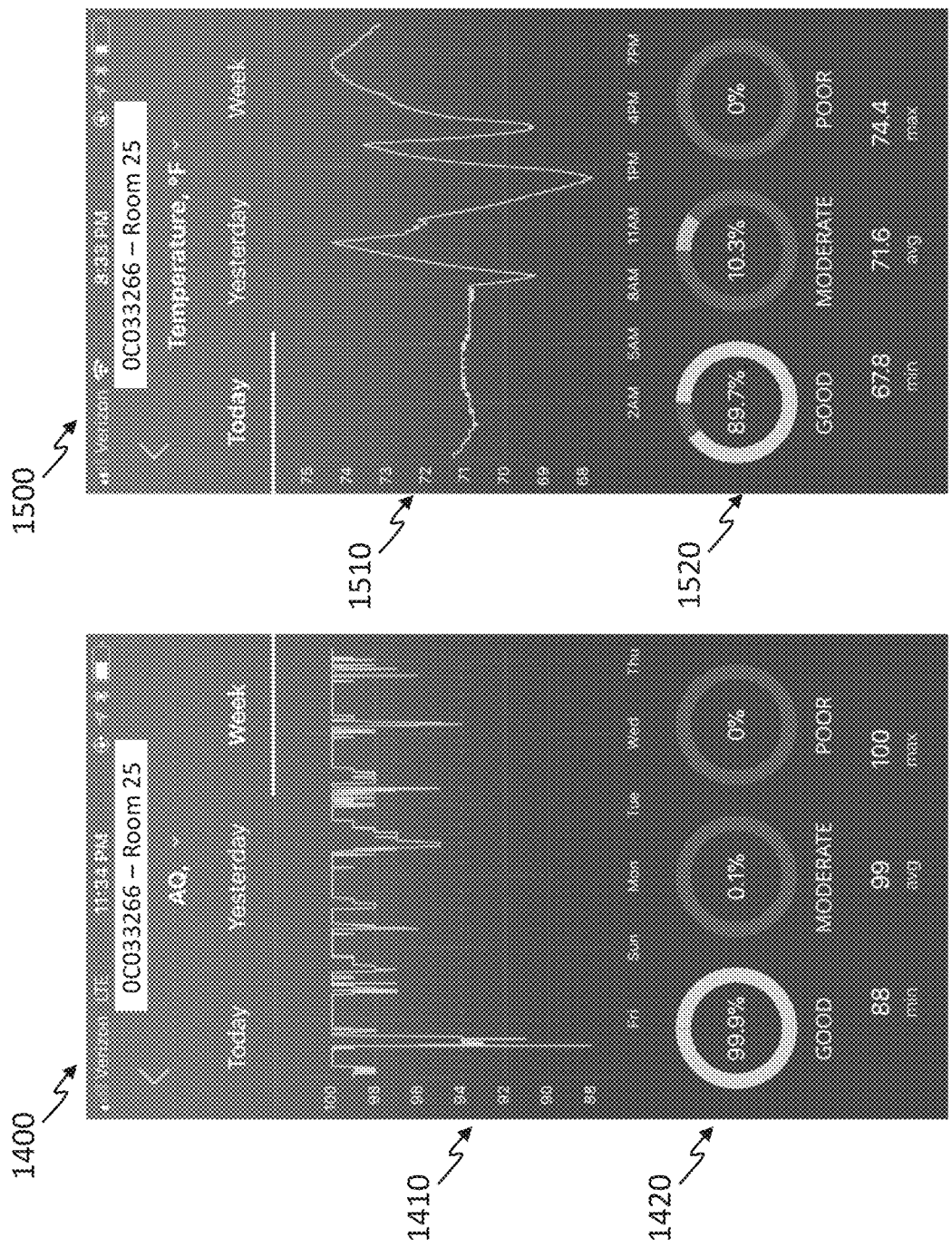
FIG. 14 is an exemplary variation of a mobile application-based graphical user interface for use in the environment quality monitoring system.
FIG. 15 is an exemplary variation of a mobile application-based graphical user interface for use in the environment quality monitoring system.

FIG. 14 is an exemplary GUI 1400 of a mobile application for use in conjunction with an environment quality monitoring system. GUI 1400 may be similar to GUI 900 described above with reference to FIG. 9, in that GUI 1400 displays a detailed view including historical trend information in a chart 1410 relating to a selected environment quality parameter as measured by a selected environment quality monitoring device. Information for predetermined time periods, such as current day, preceding day, and preceding week, may be displayed. In the example of FIG. 14, historical trend of environment quality score over the preceding week is displayed. Furthermore, statistical information regarding historical environment quality information may be displayed. For example, minimum value, average value, and/or maximum value of the environment quality score (or other selected parameter) for the selected time period may be displayed. As another example, icons 1420 may summarize how often the environment quality score (or other selected parameter) is considered to fall into certain descriptive categories. In the example of FIG. 14, the GUI 1400 displays relative occurrences of the environment quality score being categorized as "good", "moderate", and "poor" in terms of numerical percentages of durations and a pie chart to graphically indicate the same.

FIG. 15 is an exemplary GUI 1500 of a mobile application for use in conjunction with an environment quality monitoring system. The GUI 1500 is similar to GUI 1400 described above with reference to FIG. 14, except that the example of FIG. 15 specifically displays information relating to temperature. For example, historical trend temperature over the current day (e.g., preceding 24 hours, or time period beginning at midnight of the current day) are displayed in chart 1510. Relative occurrences of the temperature being categorized as "good", "moderate", and "poor" are displayed in terms of numerical percentages of durations and a pie chart to graphically indicate the same.

Figure 22:
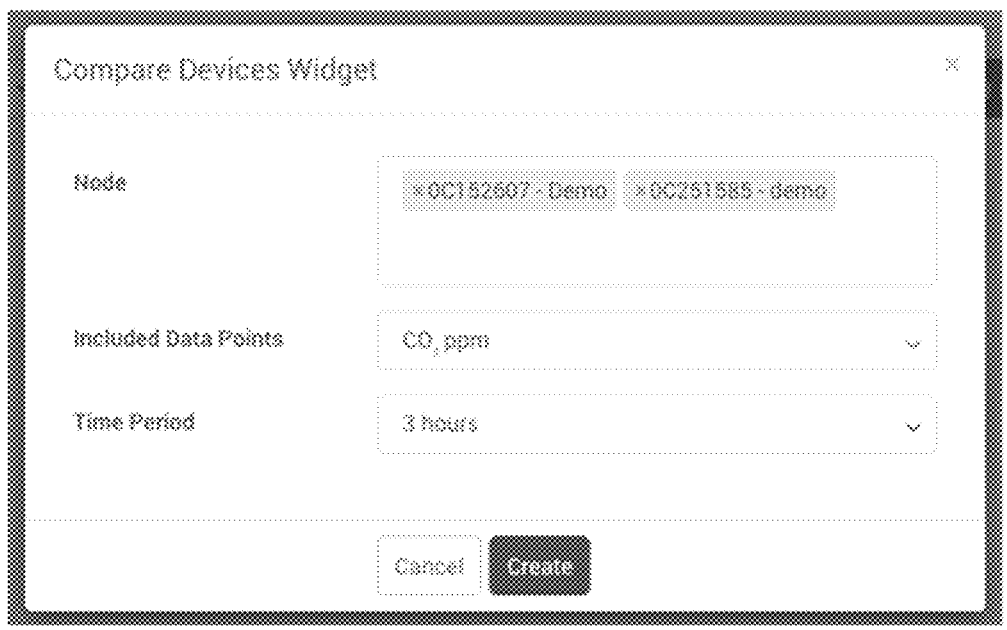
FIG. 22 is an exemplary variation of a graphical user interface for use in the environment quality monitoring system.

FIG. 22 is an exemplary GUI 2200 of a web portal or mobile application for use in conjunction with an environment quality monitoring system. GUI 2200 enables a comparison of one or more environment quality parameters (e.g., $CO_2$ level) as measured across any selected duration of time, by any one or more selected environment quality monitoring devices ("nodes"). Accordingly, the GUI 2200 may be used to perform a comparison of at least one environmental quality parameter throughout any time of the day, week, month, etc., which may provide an understanding of micro-environments. A micro-environment may, for example, be a defined space indoors (e.g., due to walls, rooms, etc.), such as a floor in a building, a region of a floor, a room, etc. This understanding may provide an opportunity to take actions to eliminate hazardous or otherwise undesirable conditions in the micro-environment.

Figure 23:
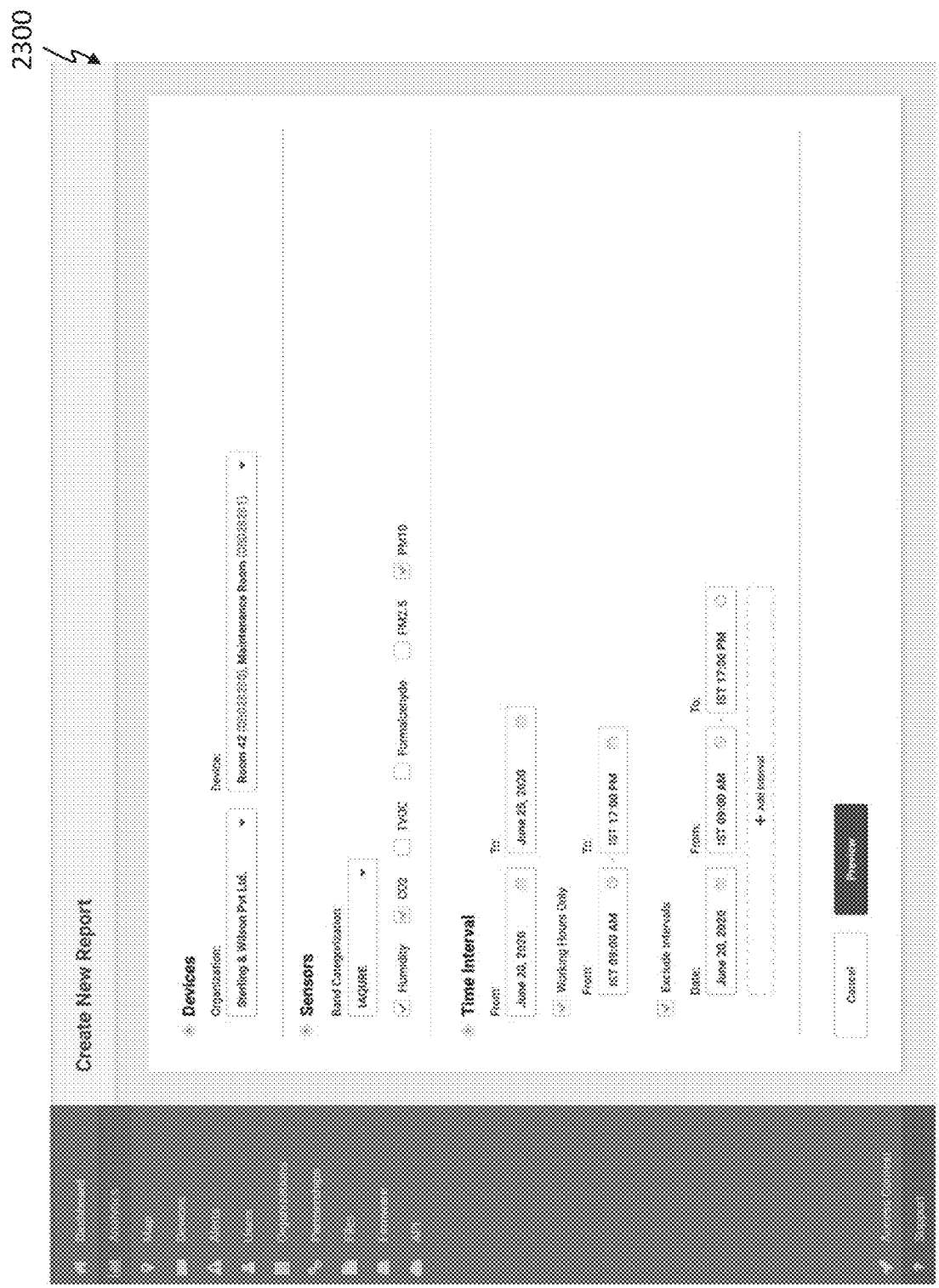
FIG. 23 is an exemplary variation of a graphical user interface for use in the environment quality monitoring system.

FIG. 23 is an exemplary GUI 2300 of a web portal or mobile application for use in conjunction with an environment quality monitoring system. Often, it may be desirable to evaluate environment (e.g., air) quality performance in a building with respect to government or other standards (e.g., EPA, OSHA, etc., which may vary among jurisdictions). Accordingly, in some variations the environment quality monitoring system may incorporate a variety of such government standards and allow comparison of a selected environment (e.g., indoor region such as a building, floor, or room) against such standards. Such a comparison may be performed across any time(s) of day and/or time period of the year. Similarly, historical summaries of one or more environment quality parameters over time may be provided in a report independent of a comparison against one or more specified standards. For example, GUI 2300 may permit user selection of appropriate environment quality monitoring device(s) (e.g., associated with an organization), appropriate sensor(s) or environment quality parameters, and/or one or more time intervals for evaluation. A report such as report 2400 shown in FIG. 24 may be generated summarizing the environment quality assessment for the selected characteristics. For example, the report 2400 may include color-coded timelines indicating the portion (e.g., percentage) of time that any one or more selected environment quality parameters has been characterized as at certain levels of severity (e.g., "very poor", "poor", "moderate", "satisfactory", "good", "excellent"). Temporal data may additionally or alternatively be presented to indicate trends in one or more environment quality parameters over time.

Figure 24:
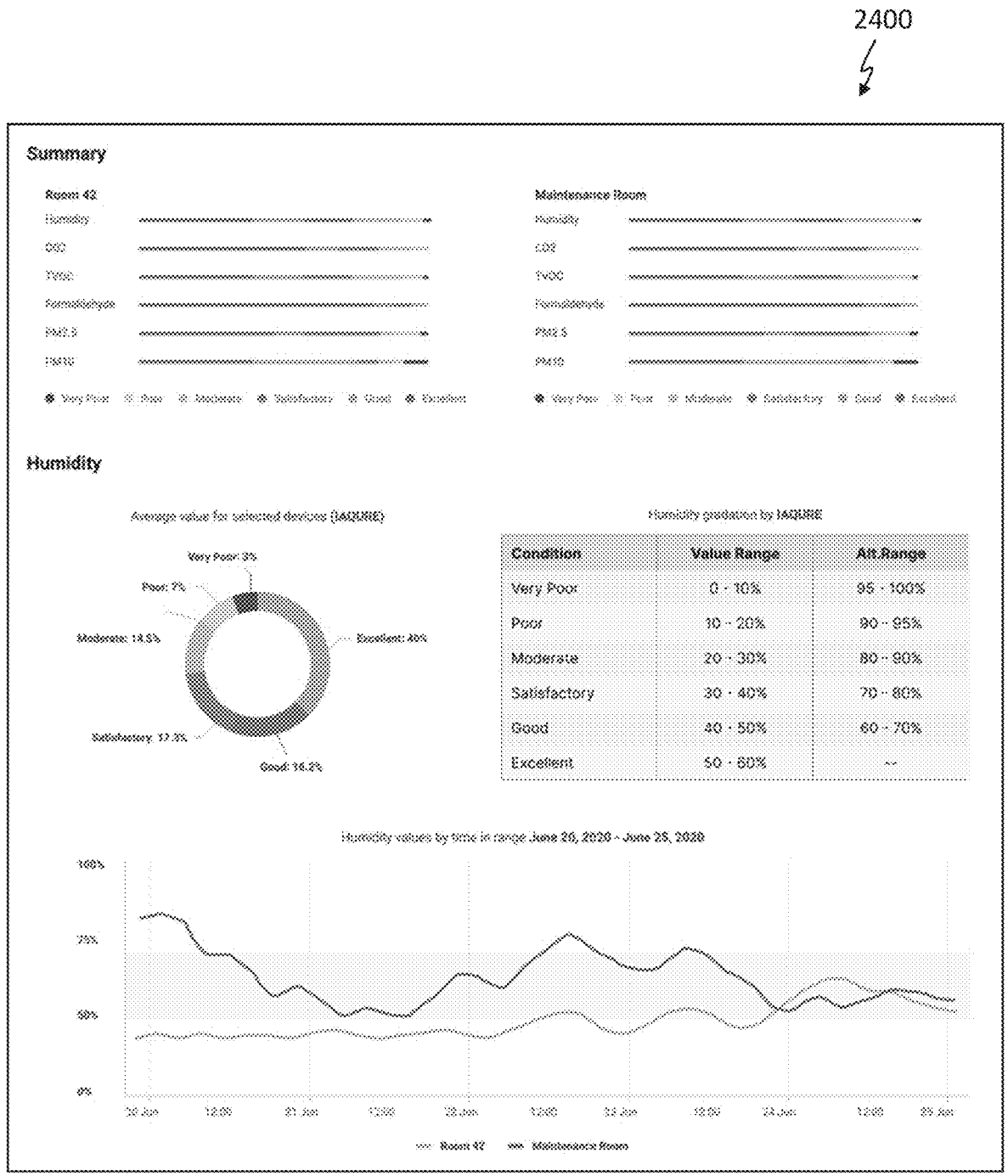
FIG. 24 is an exemplary variation of a report of environment quality data generated by an environment quality monitoring system.
Figure 25:
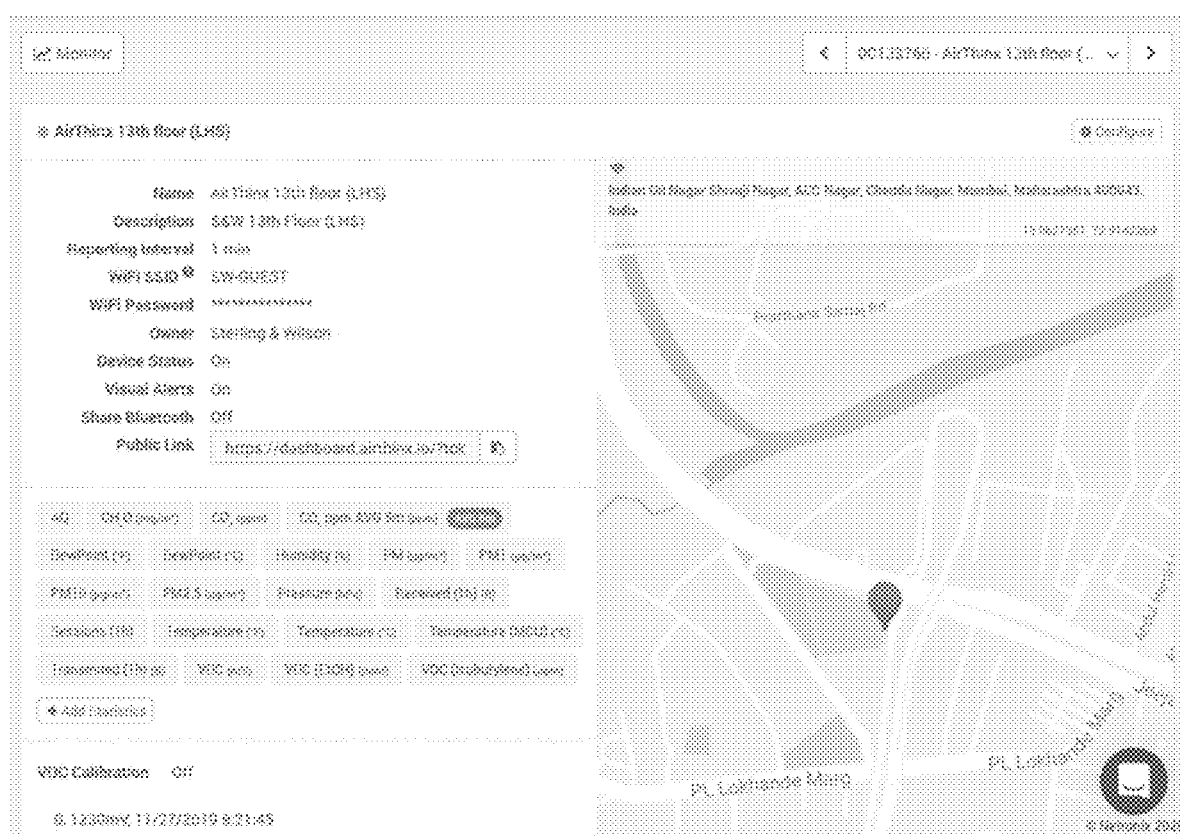
FIG. 25 is an exemplary variation of a graphical user interface for use in the environment quality monitoring system.

FIG. 24 is an exemplary GUI 2500 of a web portal or mobile application for use in conjunction with an environment quality monitoring system. GUI 2500 may enable an owner-user to generate a public access link associated with a particular environment quality monitoring device. For example, a user may select an environment quality monitoring device, and one or more environmental quality parameters for which sensor data will be accessible to the public. GUI 2500 may generate and provide a unique access weblink that may be publicly used by any suitable web-enabled device (e.g., viewable by anyone with the link, even if that person is not registered specifically to control that environmental quality monitoring device through the monitoring platform). The weblink may include a HTTP address or a machine-readable code (e.g., QR code), for example. In some variations, the resulting viewed dashboard with sensor data may automatically adjust to the web-enabled device based on screen size. In some variations, the accessibility via the link may be toggled on and off, as an owner-user of the environment quality monitoring device may enable or disable the weblink as desired. Accordingly GUI 2500 may enable a highly customizable way for an owner-user of an environment quality monitoring device to communicate environment (e.g., air) quality to the general public if desired.

Figure 26A:
FIGS. 26A and 26B depict a marketing display including an exemplary variation of a graphical user interface for use in the environment quality monitoring system.
Figure 26B:
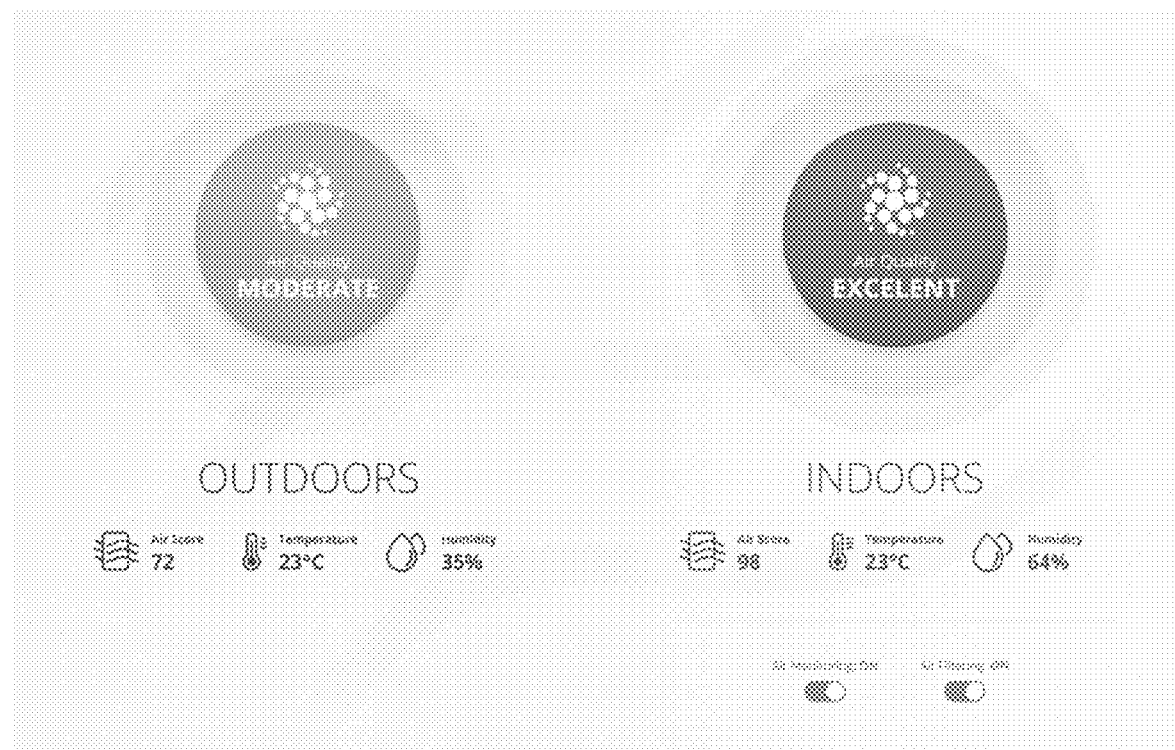

FIGS. 26A and 26B depict an exemplary GUI 2600 that may be presented for public viewing in the monitored environment, such as for marketing purposes (e.g., in a lobby, in an office, etc.) as occupants of an environment may wish to be informed of environment (e.g., air) quality around them. For example, as shown in FIG. 26A, a marketing GUI 2600 may be displayed on a monitor or other suitable display. As shown in FIG. 26B, the GUI 2600 may include a high-level summary of environment quality score and/or air quality score, and/or one or more environment quality parameters (e.g., temperature, humidity). Any suitable combination of environmental quality assessments (e.g., score, parameters, etc.) may be displayed in the marketing GUI 2600. In some variations, both indoors and outdoors environment may be summarized in the GUI 2600, for a more comprehensive summary of current conditions. The GUI 2600 may include color-coded information, such as to provide an alert to adverse environmental conditions, reassure the public of favorable conditions, etc. Measurements from one or more environment quality monitoring devices located indoors and/or outdoors may be used to generate the information displayed on GUI 2600. For example, in some variations, the summary indicated in GUI 2600 may be based on measurements (e.g., averaged measurements) from a predetermined number of environment quality monitoring devices (e.g., five devices located closest to the location of the display of GUI 2600), from all active environment quality monitoring devices within a certain distance (e.g., within 500 feet) of the location of the display of GUI 2600.

Figure 27:
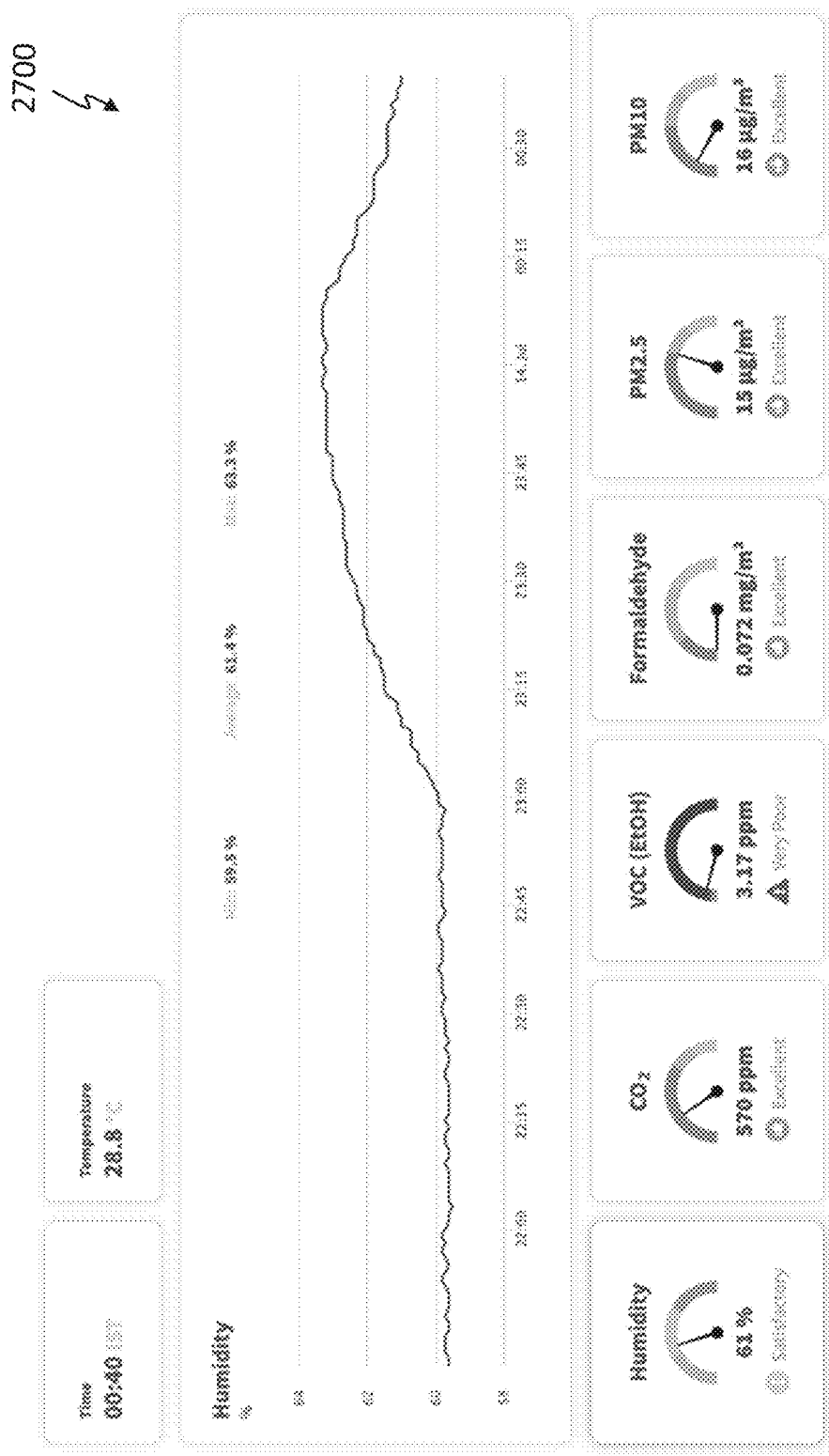
FIG. 27 is an exemplary variation of a graphical user interface for use in the environment quality monitoring system.

FIG. 27 depicts another exemplary GUI 2700 that may be presented for public viewing similar to FIGS. 26A and 26B. While GUI 2600 depicts a higher-level summary of environmental conditions, GUI 2700 depicts a more detailed summary including temporal trends and/or more environmental quality parameters. For example, GUI 2600 depicts a temporal trend of humidity, as well as current values of humidity, $CO_2$, VOCs, formaldehyde, and particulate matter levels on a gauge schematic to help illustrate severity of these parameters. Any suitable combination of environmental quality assessments (e.g., score, parameters, etc.) may be displayed in the marketing GUI 2700.

Beacon

Figure 28:
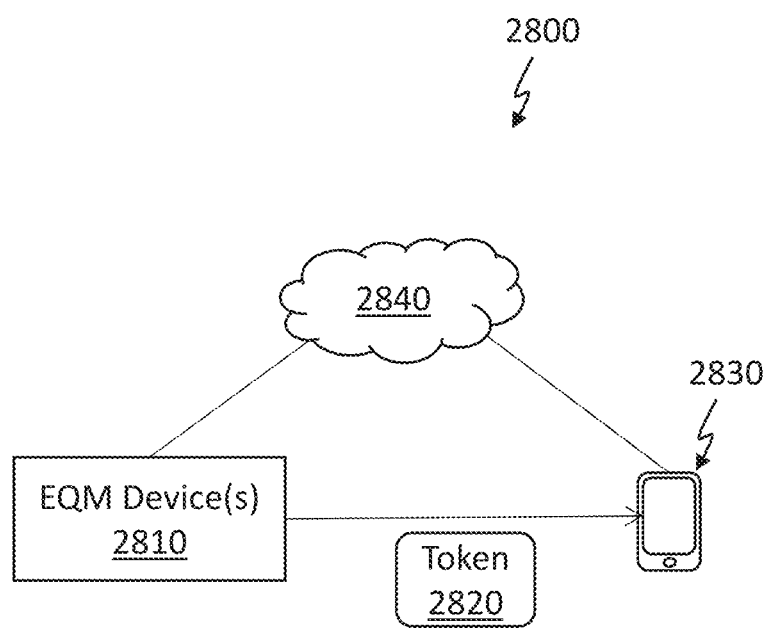
FIG. 28 is an illustrative schematic of a portion of an environment monitoring system providing a beacon function enabling a user to view environment quality information from nearby environment quality monitoring device(s).

In some instances, may be desirable to enable a person to view environmental quality data measured by a particular environmental quality monitoring device, even when that person is not a registered owner-user of that monitoring device. Accordingly, in some variations, an environment quality monitoring device may include a beacon function, whereby the environment quality monitoring device may advertise its ability to have its sensor data viewed to an authorized user. For example, with reference to FIG. 28, a beacon function may be enabled on an environment quality monitoring device 2810 (e.g., by enabling Bluetooth functionality or other network communication device or module) such that the environment quality monitoring device 2810 may start broadcasting a token 2820. This token may be received by any nearby computing device (e.g., mobile phone) that may be executing a mobile application that recognizes the token. Once this token is received, the computing device may transmit the token to a cloud network 2840 or other suitable server, which may authenticate the computing device for receiving data obtained by the environment quality monitoring device. For example, environment quality parameters and/or analysis obtained by the environment quality monitoring device may be communicated to a cloud network as described above, then communicated to the authenticated computing device. In other words, once this token authentication of a suitable computing device is complete, a user operating the authenticated computing device may be able to view environment quality data while he or she is in close proximity to the environment quality monitoring device. Once the authenticated computing device strays beyond a certain distance from the environmental quality monitoring device, the authentication may be ceased and the computing device may no longer be able to display sensor data from the environmental quality monitoring device.

Perceptual Comfort Map

The way people perceive comfort is often subject to personal preferences and/or genetics, and furthermore may be affected by other factors such as the time of the day, activity level, and/or outdoor conditions. For instance, an individual with hypercapnia (retention of $CO_2$) may feel warmer than another individual without hypercapnia, even though environmental temperature and humidity may be within normal ranges. As another example, between two environments of equal temperature but unequal humidity, the environment with higher humidity will generally feel warmer than the environment with lower humidity. As another example, an indoor room with windows and having certain indoor ambient conditions typically feels different during daytime on a sunny day compared to at night with the same indoor ambient conditions. Accordingly, individuals may desire to compensate for their individual preferences by controlling an HVAC system (e.g., cooling or warming the environment).

Figure 18:
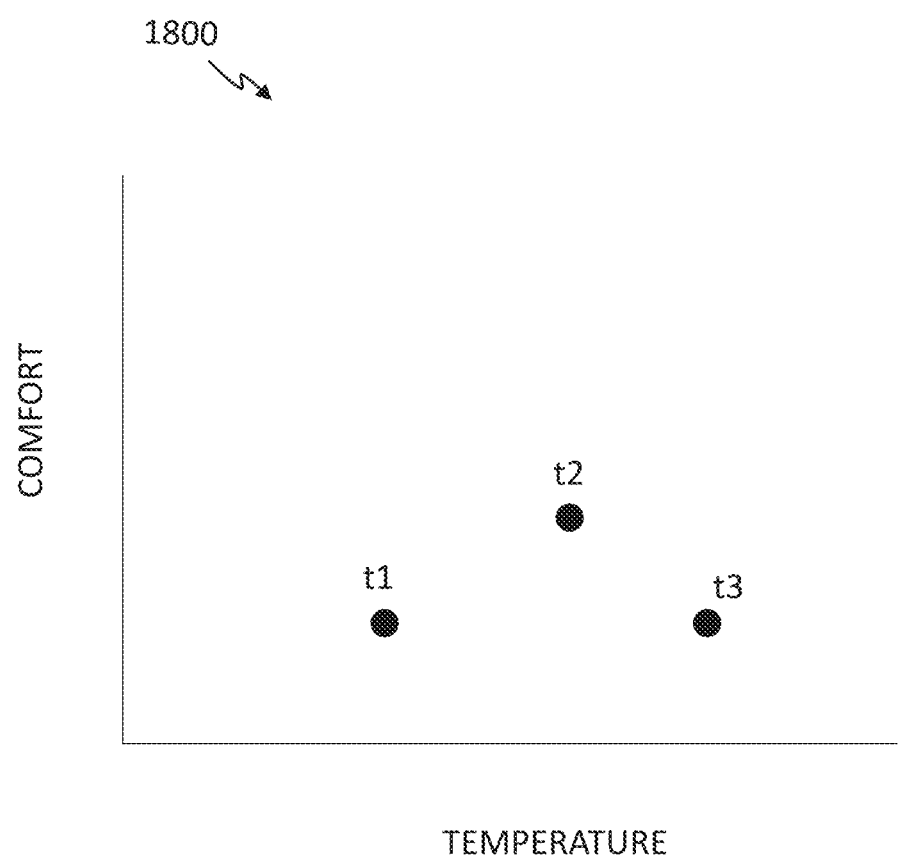
FIG. 18 is an illustrative schematic of a perceptual map displaying the relationship between user comfort and an environmental quality parameter.

In some variations, a user interface may receive one or more user inputs characterizing user comfort during different times of the day. Environmental conditions in the given space for these times of the day may also be recorded, such that a perceptual map may be created. For example, as shown in FIG. 18, a perceptual map 1800 may include a coordinate system with x-axis being temperature (and/or one or more other suitable environmental quality parameters) and y-axis being a measure of comfort (e.g., on a numerical scale). The perceptual map may characterize how an individual (or group of individuals, on average) feels during different times of the day based on the conditions in the space around the environmental monitoring device. In some variations, the perceptual map may include a plot, list, and/or other suitable data structure for storing environmental information associated with current comfort levels. For example, indoor conditions may be measured and provided by the environmental monitoring device(s) in the space, while outdoor conditions may be provided by another environmental monitoring device(s) and/or weather databases with location-specific information. Furthermore, in some variations, multiple contemporaneous environmental quality parameters may be recorded along with the user input of current comfort.

This information of each individual may feedback into the cloud network and allow creation of a profile for each individual based on the given indoor and/or outdoor conditions, and/or control of one or more devices for controlling environmental conditions. For example, artificial intelligence and/or machine learning techniques may be applied to the input information and locally and/or via the cloud network create a closed loop system with other wired and/or wireless cloud-enabled environment modulating devices such as thermostats, humidifiers, dehumidifiers, HVAC systems, air purifier, other air exchanging units, etc. Accordingly, an environmental quality monitoring system may further control such environment modulating devices in order to satisfy the comfort level of the individual based on the individual's profile (or average comfort level of all local individuals combined). In some variations, the environmental monitoring device may be integrated directly with one or more environment modulating devices instead of being communicatively connected via a wired or wireless network. In other words, an environmental quality monitoring system may provide remediation for perceived discomfort for one or more individuals in the space(s).

Although exemplary variations of web portal application GUIs and mobile application GUIs are described above as having certain features, it should be understood that features of the exemplary web portal application GUIs and the exemplary mobile application GUIs described herein may be combined in any suitable manner.

EXAMPLE EMBODIMENTS

Embodiment A1. A method for managing air quality, comprising:
at one or more processors:
receiving sensor data comprising a plurality of air quality parameters for an environment, wherein the sensor data is generated by one or more environment quality monitoring devices located in the environment;
predicting an adverse air quality event based on the sensor data; and
automatically controlling one or more devices to mitigate the adverse air quality event.

Embodiment A2. The method of embodiment A1, wherein the plurality of air quality parameters comprises an amount of particulate matter in the environment.

Embodiment A3. The method of embodiment A2, wherein the adverse air quality event comprises an amount of particulate matter above a predetermined threshold level, and wherein automatically controlling one or more devices to mitigate the adverse air quality event comprises automatically activating one or more air filtering devices.

Embodiment A4. The method of embodiment A1, wherein the plurality of air quality parameters comprises an amount of a gas in the environment.

Embodiment A5. The method of embodiment A4, wherein the gas comprises at least one of carbon dioxide, carbon monoxide, formaldehyde, and a volatile organic compound (VOC).

Embodiment A6. The method of embodiment A4, wherein the adverse air quality event comprises an amount of the gas above a predetermined threshold level, and wherein automatically controlling one or more devices to mitigate the adverse air quality event comprises automatically activating one or more air purification devices.

Embodiment A7. The method of embodiment A1, wherein the plurality of air quality parameters comprises one or more of temperature, humidity, and pressure in the environment.

Embodiment A8. The method of embodiment A7, wherein the adverse air quality event comprises at least one of temperature, humidity, and pressure outside a predetermined range, and wherein automatically controlling one or more devices to mitigate the adverse air quality event comprises automatically activating at least one of an HVAC system, a humidifier, and a dehumidifier.

Embodiment A9. The method of embodiment A1, further comprising generating an air quality score based on at least a portion of the air quality parameters.

Embodiment A10. The method of embodiment A9, wherein generating the air quality score is based on a plurality of weighted factors applied to at least a portion of the air quality parameters.

Embodiment A11. The method of embodiment A9, wherein the adverse air quality event is based at least in part on the air quality score.

Embodiment A12. The method of embodiment A1, wherein receiving sensor data comprises receiving sensor data from the one or more environment quality monitoring devices over a wireless communication network.

Embodiment A13. The method of embodiment A12, wherein the wireless communication network is a cellular network.

Embodiment A14. The method of embodiment A1, wherein the one or more environment quality monitoring devices and the one or more devices to mitigate the adverse air quality event are communicatively coupled to a common cloud network.

Embodiment A15. The method of embodiment A14, wherein the one or more devices to mitigate the adverse air quality event is configured to communicate to the cloud network via an application programming interface (API).

Embodiment A16. The method of embodiment A1, further comprising providing an alert regarding the predicted adverse air quality event.

Embodiment A17. The method of embodiment A16, wherein the alert comprises a visual or audible alert on the one or more environment quality monitoring devices.

Embodiment A18. The method of embodiment A16, wherein the alert comprises a notification on a remote computing device.

Embodiment A19. The method of embodiment A1, wherein at least one of the environment quality monitoring devices is located indoors.

Embodiment A20. The method of embodiment A1, wherein at least one of the environment quality monitoring devices is located outdoors.

Embodiment B1. An environment quality monitoring system, comprising:
a housing;
a plurality of sensors in the housing and configured to generate sensor data comprising a plurality of environment quality parameters characterizing ambient environment, wherein the plurality of environment quality parameters comprise two or more of an amount of particulate matter, an amount of a gas, temperature, humidity, pressure, sound intensity, and light intensity in ambient environment;
a network communication device configured to communicate the sensor data over a network; and an alert configured to indicate an environment quality score of ambient environment, wherein the environment quality score is based on at least a portion of the sensor data.

Embodiment B2. The system of embodiment B1, wherein the housing comprises a mount.

Embodiment B3. The system of embodiment B1, wherein the plurality of sensors comprises a first particulate sensor configured to measure an amount of particulate matter below about 10 µm in diameter.

Embodiment B4. The system of embodiment B3, wherein the plurality of sensors comprises a second particulate sensor configured to measure an amount of particulate matter below about 2.5 µm in diameter.

Embodiment B5. The system of embodiment B4, wherein the plurality of sensors comprises a third particulate sensor configured to measure an amount of particulate matter below about 1 µm in diameter.

Embodiment B6. The system of embodiment B1, wherein the gas comprises at least one of carbon dioxide, carbon monoxide, formaldehyde, and a volatile organic compound (VOC).

Embodiment B7. The system of embodiment B1, wherein the plurality of sensors comprises a sound sensor configured to measure sound intensity.

Embodiment B8. The system of embodiment B1, wherein the plurality of sensors comprises a photodiode configured to measure light intensity.

Embodiment B9. The system of embodiment B1, wherein one or more of the sensors are replaceable.

Embodiment B10. The system of embodiment B1, wherein the alert comprises a visual alert on the housing.

Embodiment B11. The system of embodiment B10, wherein the housing comprises a light waveguide configured to display the visual alert.

Embodiment B12. The system of embodiment B10, wherein the visual alert is color-coded based on a comparison between the environment quality score and one or more predetermined thresholds.

Embodiment B13. The system of embodiment B1, wherein the network communication device is configured to communicate the sensor data over a wireless network.

Embodiment B14. The system of embodiment B13, wherein the network communication device comprises a cellular modem.

Embodiment B15. The system of embodiment B1, further comprising a processor configured to generate the environment quality score based on at least a portion of the plurality of environment quality parameters.

Embodiment B16. The system of embodiment B15, wherein the processor is configured to generate the environment quality score based on a plurality of weighted factors applied to a least a portion of the environment quality parameters.

Embodiment B17. The system of embodiment B1, wherein the environment quality score comprises an air quality score.

Embodiment B18. The system of embodiment B1, further comprising a user interface configured to display at least one of the sensor data and the environment quality score.

Embodiment B19. The system of embodiment B18, wherein the user interface is displayable in a web portal or mobile application on a remote computing device.

Embodiment B20. The system of embodiment B18, wherein the user interface is configured to communicate to the network via an application programming interface (API).

Embodiment B21. The system of embodiment B1, further comprising a processor configured to generate an environment quality parameter score characterizing a severity of risk associated with at least one environment quality parameter value.

Embodiment B22. The system of embodiment B21, further comprising a user interface configured to display the environment quality parameter score.

Embodiment B23. The system of embodiment B1, further comprising a power source.

Embodiment B24. The system of embodiment B23, wherein the power source is a rechargeable battery coupled to the housing.

Embodiment B25. The system of embodiment B1, further comprising a mount configured to couple the housing to a surface.

Embodiment B26. The system of embodiment B25, wherein the mount is configured to interface with an HVAC unit.

Embodiment B27. The system of embodiment B25, further comprising a locking mechanism releasably coupling the housing to the mount.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A method for managing air quality, comprising:
at one or more processors:
receiving sensor data remotely via a cloud network directly from one or more environment quality monitoring devices located in an environment, wherein the sensor data is generated by the one or more environment quality monitoring devices and comprises a plurality of air quality parameters, wherein each air quality parameter of the plurality of air quality parameters is representative of a different respective environmental characteristic of the environment;
generating an air quality score based on at least a portion of the air quality parameters, wherein each air quality parameter is associated with a respective weighting factor, and wherein generating the air quality score comprises summing a measure of a severity of each air quality parameter multiplied by its respective associated weighting factor, wherein the measure of severity of each air quality parameter is expressed as a ratio of current parameter value to maximum possible parameter value;

predicting an adverse air quality event based on the air quality score; and automatically controlling, remotely via the cloud network, one or more devices to mitigate the adverse air quality event.

2. The method of claim 1, wherein the plurality of air quality parameters comprises an amount of particulate matter in the environment.

3. The method of claim 2, wherein the adverse air quality event comprises an amount of particulate matter above a predetermined threshold level, and wherein automatically controlling one or more devices to mitigate the adverse air quality event comprises automatically activating one or more air filtering devices.

4. The method of claim 1, wherein the plurality of air quality parameters comprises an amount of a gas in the environment.

5. The method of claim 4, wherein the gas comprises at least one of carbon dioxide, carbon monoxide, formaldehyde, and a volatile organic compound (VOC).

6. The method of claim 4, wherein the adverse air quality event comprises an amount of the gas above a predetermined threshold level, and wherein automatically controlling one or more devices to mitigate the adverse air quality event comprises automatically activating one or more air purification devices.

7. The method of claim 1, wherein the plurality of air quality parameters comprises one or more of temperature, humidity, and pressure in the environment.

8. The method of claim 7, wherein the adverse air quality event comprises at least one of temperature, humidity, and pressure outside a predetermined range, and wherein automatically controlling one or more devices to mitigate the adverse air quality event comprises automatically activating at least one of an HVAC system, a humidifier, and a dehumidifier.

9. The method of claim 1, wherein receiving sensor data comprises receiving sensor data from the one or more environment quality monitoring devices over a wireless communication network.

10. The method of claim 9, wherein the wireless communication network is a cellular network.

11. The method of claim 1, wherein the one or more devices to mitigate the adverse air quality event is configured to communicate to the cloud network via an application programming interface (API).

12. The method of claim 1, further comprising providing an alert regarding the predicted adverse air quality event.

13. The method of claim 12, wherein the alert comprises a visual or audible alert on the one or more environment quality monitoring devices.

14. The method of claim 12, wherein the alert comprises a notification on a remote computing device.

15. The method of claim 1, wherein at least one of the environment quality monitoring devices is located indoors.

16. The method of claim 1, wherein at least one of the environment quality monitoring devices is located outdoors.

* * * * *